United States Patent
Lai et al.

(10) Patent No.: US 11,980,670 B2
(45) Date of Patent: May 14, 2024

(54) USE OF PCBP1 TO TREAT HYPERPROLIFERATIVE DISEASE

(71) Applicant: Ibex Biosciences, Inc., Cumberland, MD (US)

(72) Inventors: Norman Zhennan Lai, N. Potomac, MD (US); Michael Joseph Karlin, Bethesda, MD (US); Alberto Murat Croci, Washington, DC (US); Vidal Felix de la Cruz, Jr., Phoenixville, PA (US); Yuebin Tan, Cumberland, MD (US)

(73) Assignee: Ibex Biosciences, Inc., Cumberland, MD (US)

( * ) Notice: Subject to any disclaimer, the term of this patent is extended or adjusted under 35 U.S.C. 154(b) by 648 days.

(21) Appl. No.: 16/967,507

(22) PCT Filed: Feb. 5, 2019

(86) PCT No.: PCT/US2019/016688
§ 371 (c)(1),
(2) Date: Aug. 5, 2020

(87) PCT Pub. No.: WO2019/153008
PCT Pub. Date: Aug. 8, 2019

(65) Prior Publication Data
US 2021/0113714 A1    Apr. 22, 2021

Related U.S. Application Data

(60) Provisional application No. 62/626,424, filed on Feb. 5, 2018.

(51) Int. Cl.
*A61K 48/00*    (2006.01)
*A61P 35/04*    (2006.01)
*C12N 15/86*    (2006.01)

(52) U.S. Cl.
CPC ............ *A61K 48/005* (2013.01); *A61P 35/04* (2018.01); *C12N 15/86* (2013.01)

(58) Field of Classification Search
None
See application file for complete search history.

(56) References Cited

U.S. PATENT DOCUMENTS

| | | |
|---|---|---|
| 2003/0138954 A1 | 7/2003 | Trono et al. |
| 2004/0067535 A1 | 4/2004 | Kim et al. |
| 2004/0241797 A1 | 12/2004 | Guy |
| 2010/0093090 A1 | 4/2010 | Deng et al. |
| 2013/0149284 A1 | 6/2013 | Malcuit et al. |
| 2013/0280806 A1 | 10/2013 | Rubin et al. |
| 2016/0168594 A1 | 6/2016 | Zhang et al. |
| 2017/0029486 A1 | 2/2017 | Mahr et al. |
| 2018/0010134 A1 | 1/2018 | Sharp et al. |
| 2022/0228126 A1 | 7/2022 | Lai et al. |

FOREIGN PATENT DOCUMENTS

| | | |
|---|---|---|
| CN | 1606456 A | 4/2005 |
| CN | 101550406 A | 10/2009 |
| CN | 104338150 A | 2/2015 |
| WO | WO 2019/153008 A1 | 8/2019 |
| WO | WO 2021/026488 A2 | 2/2021 |

OTHER PUBLICATIONS

Du, et al. (2008) "Structure of a Construct of a Human Poly(c)-binding Protein Containing the First and Second KH Domains Reveals Insights into Its regulatory Mechanisms", The Journal of Biological Chemistry, 283(42): 28757-66. (Year: 2008).*
Meng, et al. (2007) "Signaling-dependent and coordinated regulation of transcription, splicing, and translation resides in a single coregulator, PCBP1", Proceedings of the National Academy of Sciences, USA, 104(14): 5866-71. (Year: 2007).*
Chaudhury, et al., "TGF-β-mediated phosphorylation of hnRNP E1 induces EMT via transcript-selective translational induction of Dab2 and ILEI". Nature Cell Biology. (Mar. 2010); 12(3): 286-293. Epub Feb. 14, 2010.
Chen, et al., "Inefficient reprogramming of fibroblasts into cardiomyocytes using Gata4, Mef2c, and Tbx5". Circulation Research (Jun. 22, 2012); 111(1): 50-55.
Ghanem, et al., "The poly (C) binding protein Pcbp2 and its retrotransposed derivative Pcbp1 are independently essential to mouse development". Molecular and cellular biology. Nov. 2, 2015;36(2):304-19. Published online Jan. 4, 2016. Prepublished online Nov. 2, 2015.
Ma, et al., "Direct cardiac reprogramming as a novel therapeutic strategy for treatment of myocardial infarction". Kiyotake Ishikawa (ed.), in Cardiac Gene Therapy: Methods and Protocols, Methods in Molecular Biology (2017); vol. 1521, Ch. 5, pp. 69-88). Humana Press, New York, NY.
NCBI reference sequence NP 006187; poly(rC)-binding protein 1 [*Homo sapiens*], Publication (online]. Nov. 1, 2017 [retrieved Apr. 4, 2019). Retrieved from the Internet: <URL:https://www.ncbi.nlm.nih.gov/protein/NP006187.2>; pp. 1-4.
PCT/US2019/016688, International Preliminary Report on Patentability dated Aug. 11, 2020, 11 pages.
PCT/US2019/016688, International Search Report and Written Opinion dated Jun. 11, 2019, 16 pages.
PCT/US2019/016688, Invitation to Pay Additional Search Fees dated Apr. 9, 2019, 3 pages.
PCT/US2020/045477, International Search Report and Written Opinion dated Feb. 16, 2021, 9 pages.

(Continued)

*Primary Examiner* — Robert M Kelly
(74) *Attorney, Agent, or Firm* — COOLEY LLP

(57) ABSTRACT

The present disclosure provides compositions and methods of using gene therapy to decrease cell migration and metastasis and reduce tumor mass or burden. The methods disclosed herein employ plasmids, vectors, and non-viral vectors that contain PCBP1 and/or PCBP1 mutants which inhibit the expression of cancer biomarkers and decrease cell migration or tumor size.

24 Claims, 44 Drawing Sheets
Specification includes a Sequence Listing.

(56) References Cited

OTHER PUBLICATIONS

Takahashi, et al., "Induction of pluripotent stem cells from adult human fibroblasts by defined factors". Cell (Nov. 30, 2007); 131(5): 861-872.
Wang, et al., "PCBP1 suppresses the translation of metastasis-associated PRL-3 phosphatase". Cancer Cell (Jul. 13, 2010); 18(1): 52-62.
Extended European Search Report for European Application No. 19747924.9, dated Oct. 14, 2021, 6 pages.
Meng et al., "Signaling-dependent and coordinated regulation of transcription, splicing, and translation resides in a single coregulator, PCBP1," Proceedings of the National Academy of Sciences, vol. 104, No. 14, Apr. 3, 2007, pp. 5866-5871.
Wenliang et al., "Poly C binding protein 1 represses autophagy through downregulation of LC3B to promote tumor cell apoptosis in starvation," Int. J. Biochem. Cell Biol., Apr. 2016, vol. 73, pp. 127-136. Epub Feb. 12, 2016.
PCT/US2020/045477, International Preliminary Report on Patentability dated Feb. 17, 2022, 8 pages.
Al-Aidaroos, A.Q.O., "PRL-3 phosphatase and cancer metastasis," Journal of Cellular Biochemistry, Nov. 4, 2010, pp. 1087-1098, https://doi.org/10.1002/jcb.22913.
Evans, J.R., et al., "Members of the poly (rC) binding protein family stimulate the activity of the c-myc internal ribosome entry segment in vitro and in vivo", Oncogene, Nature Publishing Group UK, London, vol. 22, No. 39, Sep. 11, 2003, pp. 8012-8020.
Extended European Search Report for European Application No. EP20849515 dated Jul. 24, 2023, 12 pages.
Huo, L.R., et al., "Identification of transcripts and translatants targeted by overexpressed PCBP1", Biochimica Et Biophysica Acta (BBA) Proteins & Proteomics, Elsevier, Netherlands, vol. 1784, No. 11, Nov. 1, 2008, pp. 1524-1533.
Ko, J.L., et al., "Poly C binding protein, a single-stranded DNA binding protein, regulates mouse—opioid receptor gene expression", Journal of Neurochemistry, vol. 93, No. 3, May 7, 2005, pp. 749-761.
Moon-Suhn, "PCBP1 and NCOA4 regulate erythroid iron storage and heme biosynthesis," The Journal of Clinical Investigation, vol. 127, No. 5, May 31, 2017, pp. 1786-1797.
Wang, X., et al., "PCBP1 inhibits the expression of oncogenic STAT3 isoform by targeting alternative splicing of STAT3 exon 23", International Journal of Biological Sciences, vol. 15, No. 6, Jan. 1, 2019, pp. 1177-1186.
Zhou, "Poly(C)-binding protein 1 (PCBP1) mediates housekeeping degradation of mitochondrial antiviral signaling (MAVS)," Cell Research, Nov. 22, 2011, pp. 717-727.

* cited by examiner

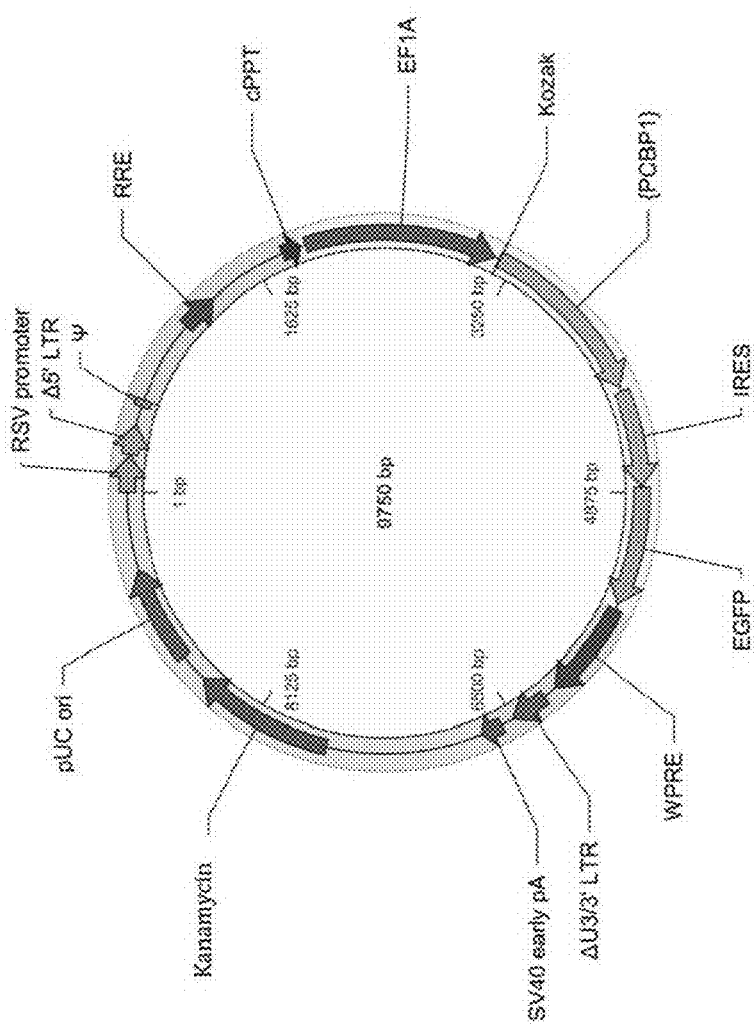
Figure 1A: Ibex therapeutic gene vector-1

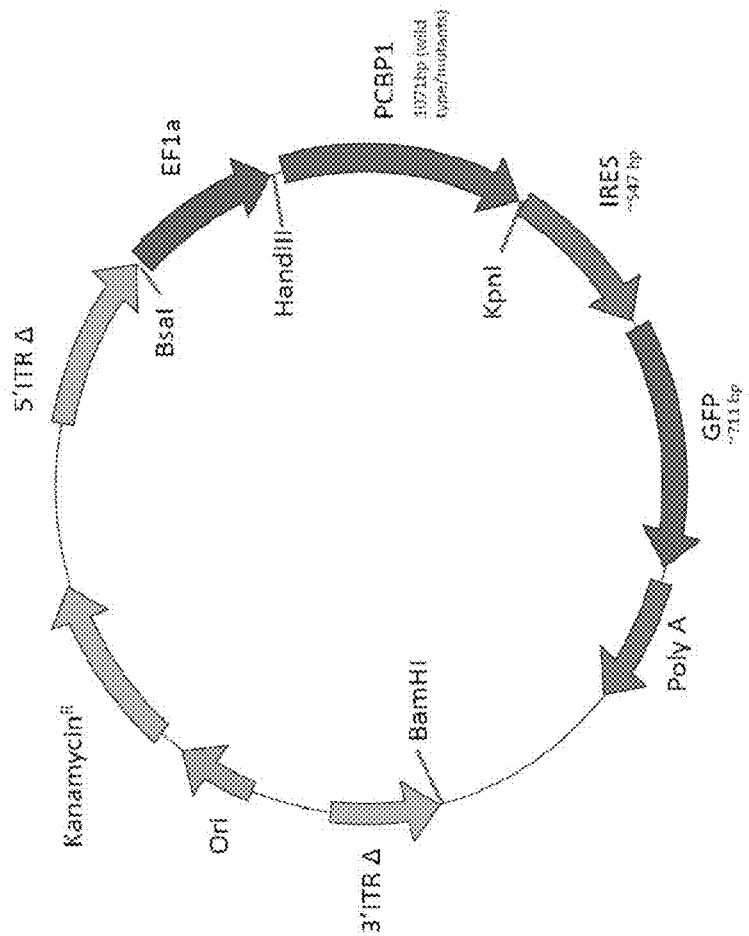
Figure 1B: Ibex therapeutic gene vector-2

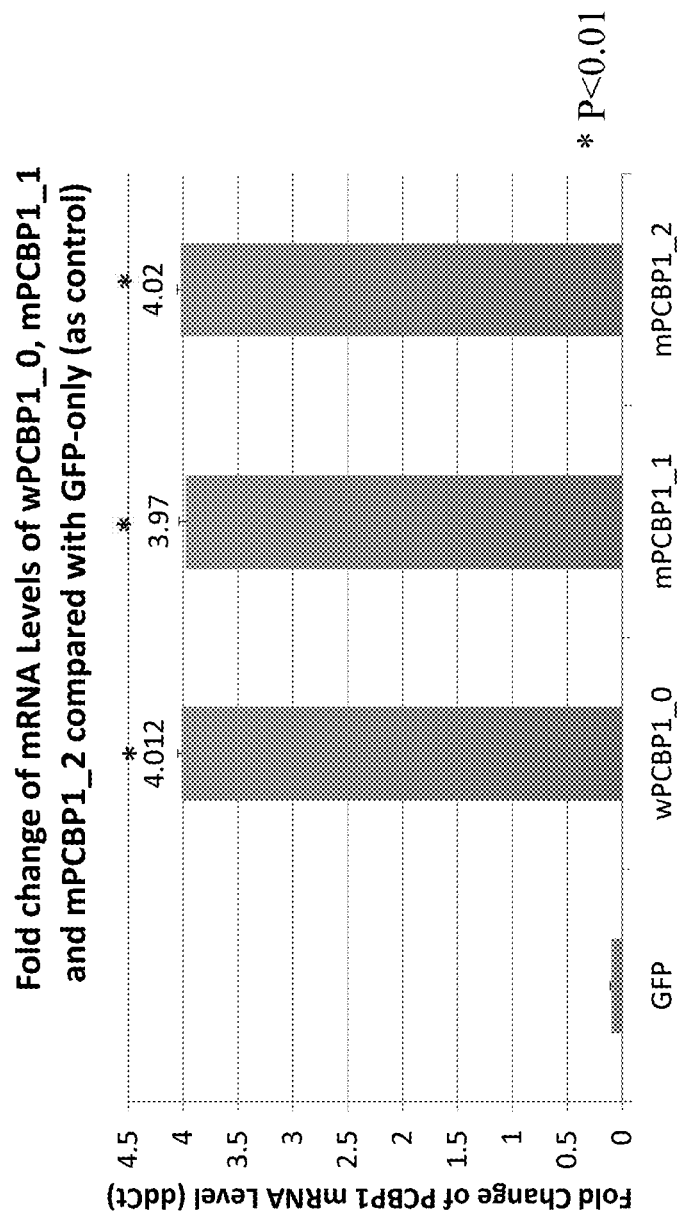
Figure 2A: Fold Change of PCBP1 mRNA Level in Melanoma Cell Line

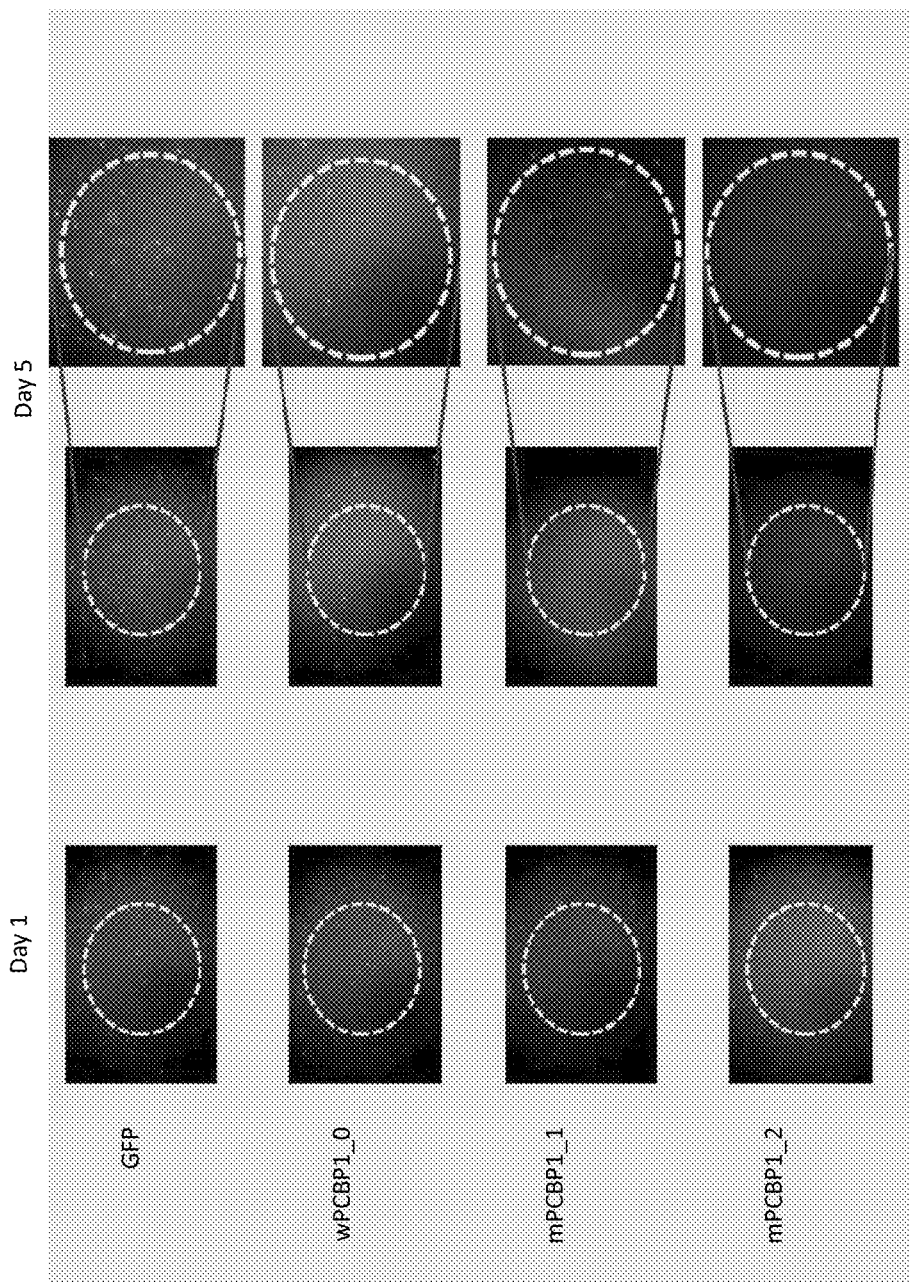
Figure 7B – Cell Migration Assay of breast cancer (MCF-7) cells

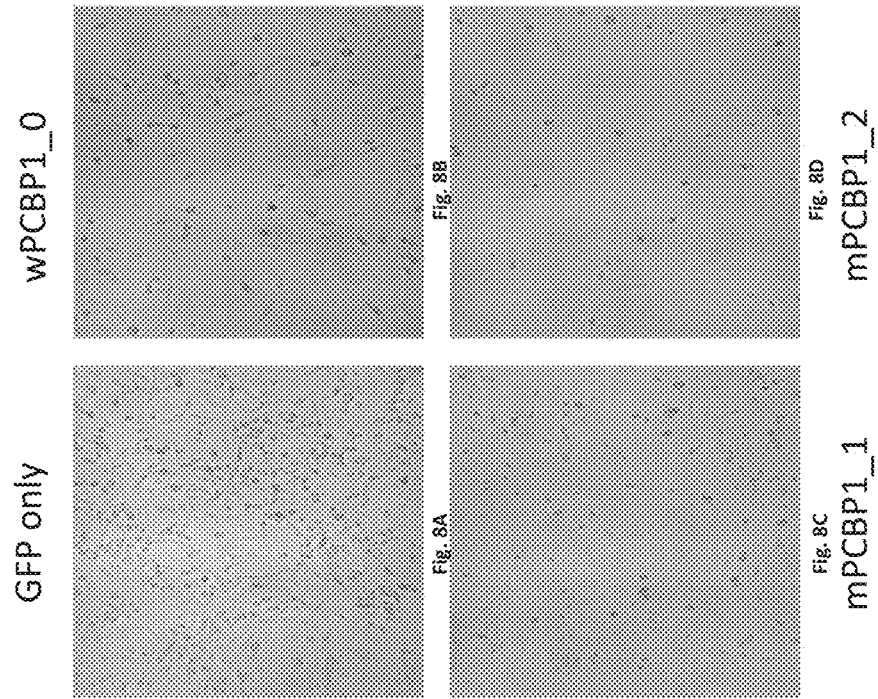
Figure 8A-D

PRL3 expression

PCBP1 expression

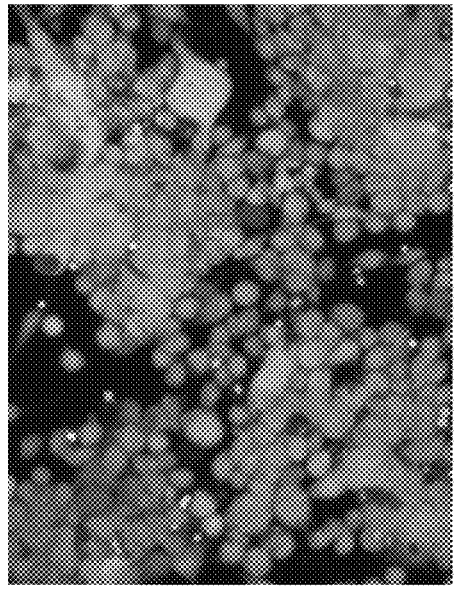
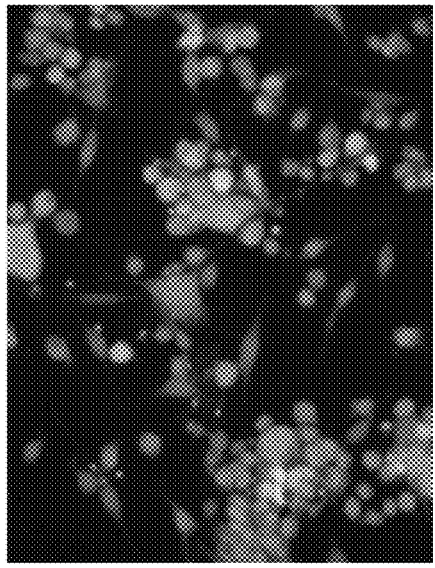
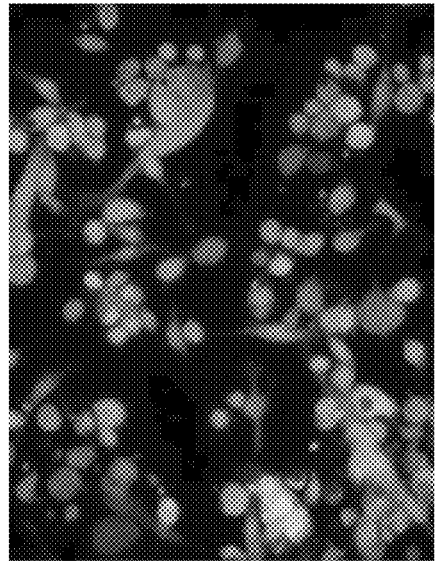
Figure. 20A (GFP)
Figure. 20B (wP)
Figure. 20C (Mu1)
Figure. 20D (Mu2)

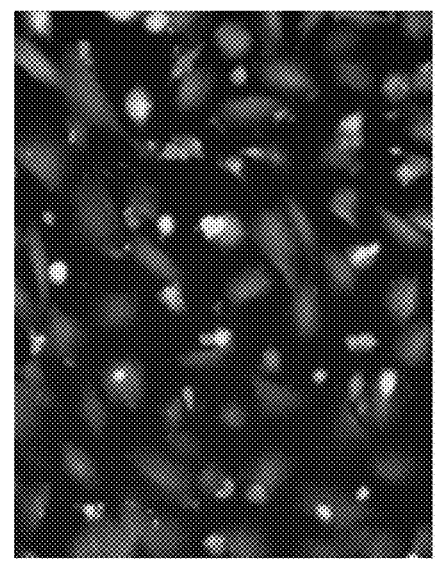
Figure. 23D (Mu2)
Figure. 23A (GFP)
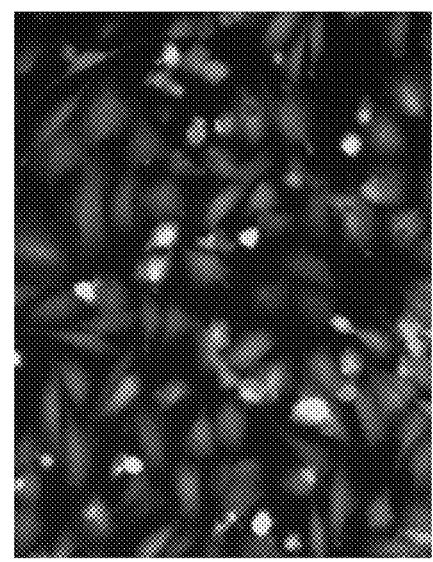
Figure. 23C (Mu1)
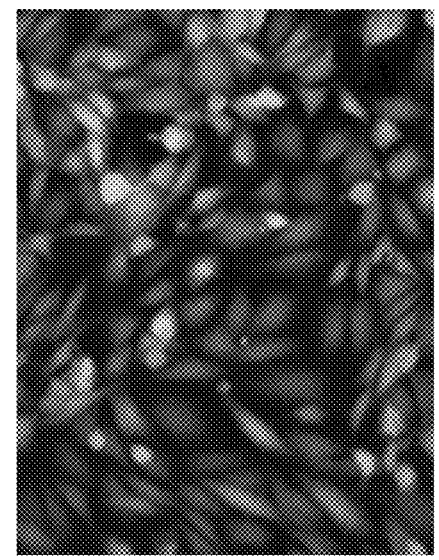
Figure. 23B (wP)

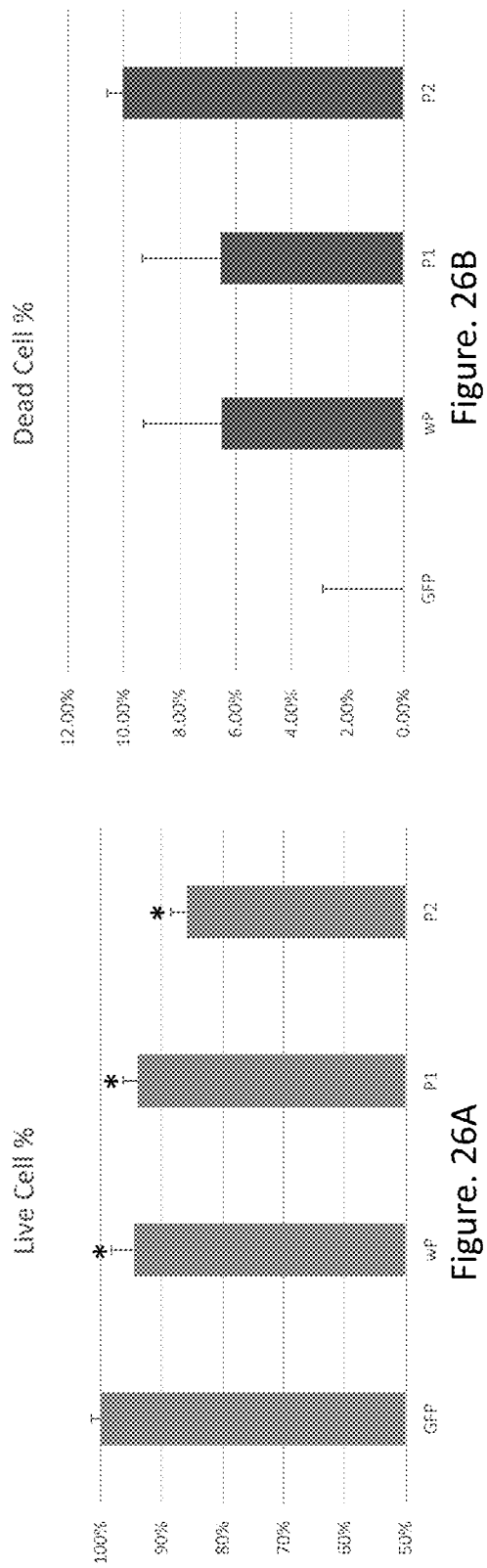

Figure 30
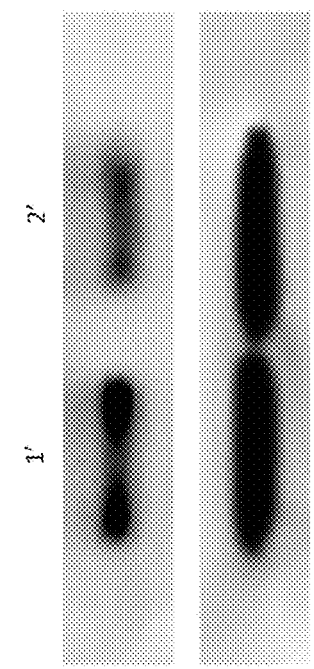
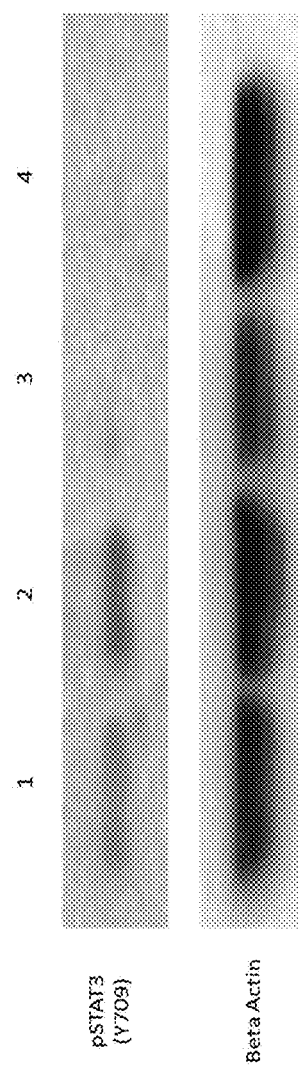

SEQUENCE LISTING

```
<160> NUMBER OF SEQ ID NOS: 13

<210> SEQ ID NO 1
<211> LENGTH: 1071
<212> TYPE: DNA
<213> ORGANISM: Homo sapiens

<400> SEQUENCE: 1
atggatgccg gtgtgactga aagtggacta aatgtgactc tcaccattcg gcttcttatg      60
cacggaaagg aagtaggaag catcattggg aagaaagggg agtcggttaa gaggatccgc     120
gaggagagtg gcgcgcggat caacatctcg gaggggaatt gtccggagag aatcatcact    180
```

```
ctgaccggcc ccaccaatgc catctttaag gctttcgcta tgatcatcga caagctggag    240
gaagatatca acagctccat gaccaacagt accgcggcca gcaggccccc ggtcaccctg    300
aggctggtgg tgccggccac ccagtgcggc tccctgattg ggaaaggcgg tgtaagatc     360 aaagagatcc gcgagagtac gggggcgcag gtccaggtgg cgggggatat gctgcccaac    420
tccaccgagc gggccatcac catcgctggc gtgccgcagt ctgtcaccga gtgtgtcaag    480
cagatttgcc tggtcatgct ggagacgctc tcccagtctc gcaagggag agtcatgacc     540 attccgtacc agcccatgcc ggccagctcc ccagtcatct gcgcgggcgg ccaagatcgg    600
tgcagcgacg ctgcgggcta cccccatgcc acccatgacc tggagggacc acctctagat    660
gcctactcga ttcaaggaca acacaccatt tctccgctcg atctggccaa gctgaaccag    720
gtggcaagac aacagtctca ctttgccatg atgcacggcg ggaccggatt cgccggaatt    780
gactccagct ctccagaggt gaaaggctat tgggcaagtt tggatgcatc tactcaaacc    840
acccatgaac tcaccattcc aaataactta attggctgca taatcgggcg ccaaggcgcc    900
aacattaatg agatccgcca gatgtccggg gcccagatca aaattgccaa cccagtggaa    960
ggctcctctg gtaggcaggt tactatcact ggctctgctg ccagtattag tctggcccag   1020
tatctaatca atgccaggct ttcctctgag aagggcatgg ggtgcagcta g            1071
```

<210> SEQ ID NO 2
<211> LENGTH: 356
<212> TYPE: PRT
<213> ORGANISM: Homo sapiens

<400> SEQUENCE: 2

```
Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
            20                  25                  30

Gly Glu Ser Val Lys Arg Ile Arg Glu Glu Ser Gly Ala Arg Ile Asn
        35                  40                  45

Ile Ser Glu Gly Asn Cys Pro Glu Arg Ile Ile Thr Leu Thr Gly Pro
    50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
        115                 120                 125

Ala Gln Val Gln Val Ala Gly Asp Met Leu Pro Asn Ser Thr Glu Arg
    130                 135                 140

Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175

Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Ala Gly Tyr Pro
        195                 200                 205

His Ala Thr His Asp Leu Glu Gly Pro Pro Leu Asp Ala Tyr Ser Ile
```

```
                 210                 215                 220
Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Gly Thr Gly
                245                 250                 255

Phe Ala Gly Ile Asp Ser Ser Pro Glu Val Lys Gly Tyr Trp Ala
            260                 265                 270

Ser Leu Asp Ala Ser Thr Gln Thr Thr His Glu Leu Thr Ile Pro Asn
        275                 280                 285

Asn Leu Ile Gly Cys Ile Ile Gly Arg Gln Gly Ala Asn Ile Asn Glu
    290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
                325                 330                 335

Ser Leu Ala Gln Tyr Leu Ile Asn Ala Arg Leu Ser Ser Glu Lys Gly
            340                 345                 350

Met Gly Cys Ser
            355

<210> SEQ ID NO 3
<211> LENGTH: 1071
<212> TYPE: DNA
<213> ORGANISM: Artificial Sequence
<220> FEATURE:
<223> OTHER INFORMATION: mPCBP1_1 (c668t)

<400> SEQUENCE: 3
atggatgccg gtgtgactga aagtggacta aatgtgactc tcaccattcg gcttcttatg      60
cacggaaagg aagtaggaag catcattggg aagaaagggg agtcggttaa gaggatccgc     120
gaggagagtg gcgcgcggat caacatctcg gaggggaatt gtccggagag aatcatcact     180
ctgaccggcc ccaccaatgc catctttaag gctttcgcta tgatcatcga caagctggag     240
gaagatatca cagctccat gaccaacagt accgcggcca gcaggccccc ggtcaccctg     300
aggctggtgg tgccggccac ccagtgcggc tccctgattg ggaaaggcgg tgtaagatc     360 aaagagatcc gcgagagtac gggggcgcag gtccaggtgg cggggggatat gctgcccaac     420 tccaccgagc gggccatcac catcgctggc gtgccgcagt ctgtcaccga gtgtgtcaag     480
cagatttgcc tggtcatgct ggagacgctc tcccagtctc gcaagggag agtcatgacc     540 attccgtacc agcccatgcc ggccagctcc cagtcatct gcgcgggcgg ccaagatcgg     600
tgcagcgacg ctgcgggcta ccccatgcc acccatgacc tggagggacc acctctagat     660
gcctacttga ttcaaggaca acacaccatt tctccgctcg atctggccaa gctgaaccag     720
gtggcaagac aacagtctca ctttgccatg atgcacggcg ggaccggatt cgccggaatt     780
gactccagct ctcagaggt gaaaggctat tgggcaagtt tggatgcatc tactcaaacc     840
acccatgaac tcaccattcc aaataactta attggctgca taatcgggcg ccaaggcgcc     900
aacattaatg agatccgcca gatgtccggg gcccagatca aaattgccaa cccagtggaa     960
ggctcctctg gtaggcaggt tactatcact ggctctgctg ccagtattag tctggcccag    1020
tatctaatca atgccaggct ttcctctgag aagggcatgg ggtgcagcta g             1071

<210> SEQ ID NO 4
<211> LENGTH: 356
<212> TYPE: PRT
```

<213> ORGANISM: Artificial Sequence
<220> FEATURE:
<223> OTHER INFORMATION: mPCBP1_1 (S223L)

<400> SEQUENCE: 4

```
Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
            20                  25                  30

Gly Glu Ser Val Lys Arg Ile Arg Glu Ser Gly Ala Arg Ile Asn
        35                  40                  45

Ile Ser Glu Gly Asn Cys Pro Glu Arg Ile Ile Thr Leu Thr Gly Pro
50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
        115                 120                 125

Ala Gln Val Gln Val Ala Gly Asp Met Leu Pro Asn Ser Thr Glu Arg
130                 135                 140

Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175

Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Ala Gly Tyr Pro
        195                 200                 205

His Ala Thr His Asp Leu Glu Gly Pro Pro Leu Asp Ala Tyr Leu Ile
210                 215                 220

Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Thr Gly
                245                 250                 255

Phe Ala Gly Ile Asp Ser Ser Pro Glu Val Lys Gly Tyr Trp Ala
            260                 265                 270

Ser Leu Asp Ala Ser Thr Gln Thr Thr His Glu Leu Thr Ile Pro Asn
        275                 280                 285

Asn Leu Ile Gly Cys Ile Ile Gly Arg Gln Gly Ala Asn Ile Asn Glu
290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
                325                 330                 335

Ser Leu Ala Gln Tyr Leu Ile Asn Ala Arg Leu Ser Ser Glu Lys Gly
            340                 345                 350

Met Gly Cys Ser
        355
```

<210> SEQ ID NO 5
<211> LENGTH: 1071
<212> TYPE: DNA

<213> ORGANISM: Artificial Sequence
<220> FEATURE:
<223> OTHER INFORMATION: mPCBP1_2 cDNA (a178g and a379g)

<400> SEQUENCE: 5

| | | |
|---|---|---|
| atggatgccg gtgtgactga aagtggacta aatgtgactc tcaccattcg gcttcttatg | 60 |
| cacggaaagg aagtaggaag catcattggg aagaaagggg agtcggttaa gaggatccgc | 120 |
| gaggagagtg gcgcgcggat caacatctcg gaggggaatt gtccggagag aatcatcgct | 180 |
| ctgaccggcc ccaccaatgc catctttaag gctttcgcta tgatcatcga caagctggag | 240 |
| gaagatatca acagctccat gaccaacagt accgcggcca gcaggccccc ggtcaccctg | 300 |
| aggctggtgg tgccggccac ccagtgcggc tccctgattg ggaaaggcgg tgtaagatc | 360 |
| aaagagatcc gcgagagtgc gggggcgcag gtccaggtgg cggggggatat gctgcccaac | 420 |
| tccaccgagc gggccatcac catcgctggc gtgccgcagt ctgtcaccga gtgtgtcaag | 480 |
| cagatttgcc tggtcatgct ggagacgctc tcccagtctc cgcaagggag agtcatgacc | 540 |
| attccgtacc agcccatgcc ggccagctcc ccagtcatct cgcgcgggcgg ccaagatcgg | 600 |
| tgcagcgacg ctgcgggcta ccccccatgcc acccatgacc tggagggacc acctctagat | 660 |
| gcctactcga ttcaaggaca acacaccatt tctccgctcg atctggccaa gctgaaccag | 720 |
| gtggcaagac aacagtctca ctttgccatg atgcacggcg ggaccggatt cgccggaatt | 780 |
| gactccagct ctccagaggt gaaaggctat tgggcaagtt tggatgcatc tactcaaacc | 840 |
| acccatgaac tcaccattcc aaataactta attggctgca taatcgggcg ccaaggcgcc | 900 |
| aacattaatg agatccgcca gatgtccggg gcccagatca aaattgccaa cccagtggaa | 960 |
| ggctcctctg gtaggcaggt tactatcact ggctctgctg ccagtattag tctggcccag | 1020 |
| tatctaatca atgccaggct ttcctctgag aagggcatgg ggtgcagcta g | 1071 |

<210> SEQ ID NO 6
<211> LENGTH: 356
<212> TYPE: PRT
<213> ORGANISM: Artificial Sequence
<220> FEATURE:
<223> OTHER INFORMATION: mPCBP1_2 (T60A and T127A)

<400> SEQUENCE: 6

Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
            20                  25                  30

Gly Glu Ser Val Lys Arg Ile Arg Glu Glu Ser Gly Ala Arg Ile Asn
        35                  40                  45

Ile Ser Glu Gly Asn Cys Pro Glu Arg Ile Ile Ala Leu Thr Gly Pro
    50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Ala Gly
        115                 120                 125

Ala Gln Val Gln Val Ala Gly Asp Met Leu Pro Asn Ser Thr Glu Arg
    130                 135                 140

```
Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175

Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Ala Gly Tyr Pro
        195                 200                 205

His Ala Thr His Asp Leu Gly Pro Pro Leu Asp Ala Tyr Leu Ile
    210                 215                 220

Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Gly Thr Gly
                245                 250                 255

Phe Ala Gly Ile Asp Ser Ser Pro Glu Val Lys Gly Tyr Trp Ala
            260                 265                 270

Ser Leu Asp Ala Ser Thr Gln Thr Thr His Glu Leu Thr Ile Pro Asn
275                 280                 285

Asn Leu Ile Gly Cys Ile Ile Gly Arg Gln Gly Ala Asn Ile Asn Glu
290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
                325                 330                 335

Ser Leu Ala Gln Tyr Leu Ile Asn Ala Arg Leu Ser Ser Glu Lys Gly
                340                 345                 350

Met Gly Cys Ser
        355

<210> SEQ ID NO 7
<211> LENGTH: 63
<212> TYPE: DNA
<213> ORGANISM: Unknown
<220> FEATURE:
<223> OTHER INFORMATION: T2A sequence in AAV vector

<400> SEQUENCE: 7
ggaagcggag agggcagggg aagtcttcta acatgcgggg acgtggagga aaatcccggc    60
ccc                                                                 63

<210> SEQ ID NO 8
<211> LENGTH: 15
<212> TYPE: DNA
<213> ORGANISM: Artificial Sequence
<220> FEATURE:
<223> OTHER INFORMATION: mutant PCBP1 mutation region sequence

<400> SEQUENCE: 8
gcctacttga ttcaa                                                    15

<210> SEQ ID NO 9
<211> LENGTH: 12
<212> TYPE: DNA
<213> ORGANISM: Artificial Sequence
<220> FEATURE:
<223> OTHER INFORMATION: mutant PCBP1 mutation region sequence

<400> SEQUENCE: 9
atcatcgctc tg                                                       12
```

```
<210> SEQ ID NO 10
<211> LENGTH: 15
<212> TYPE: DNA
<213> ORGANISM: Artificial Sequence
<220> FEATURE:
<223> OTHER INFORMATION: mutant PCBP1 mutation region sequence

<400> SEQUENCE: 10
gagagtgcgg gggcg                                                    15

<210> SEQ ID NO 11
<211> LENGTH: 5
<212> TYPE: PRT
<213> ORGANISM: Artificial Sequence
<220> FEATURE:
<223> OTHER INFORMATION: mutant PCBP1 mutation region sequence

<400> SEQUENCE: 11

Ala Tyr Leu Ile Gln
1               5

<210> SEQ ID NO 12
<211> LENGTH: 5
<212> TYPE: PRT
<213> ORGANISM: Artificial Sequence
<220> FEATURE:
<223> OTHER INFORMATION: mutant PCBP1 mutation region sequence

<400> SEQUENCE: 12

Ile Ile Ala Leu Thr
1               5

<210> SEQ ID NO 13
<211> LENGTH: 5
<212> TYPE: PRT
<213> ORGANISM: Artificial Sequence
<220> FEATURE:
<223> OTHER INFORMATION: mutant PCBP1 mutation region sequence

<400> SEQUENCE: 13

Glu Ser Ala Gly Ala
1               5
```

USE OF PCBP1 TO TREAT HYPERPROLIFERATIVE DISEASE

CROSS REFERENCE TO RELATED APPLICATIONS

This application is the National Stage of International Application No. PCT/US2019/016688, filed Feb. 5, 2019, which claims benefit of Provisional U.S. Application No. 62/626,424, filed Feb. 5, 2018, the contents of which are incorporated by reference in their entirety for all purposes.

FIELD

The present disclosure relates to compositions and methods to inhibit cell migration and cancer metastasis, and to decrease tumor burden. Specifically, the present disclosure provides methods and compositions for the transduction of cancer cells to inhibit cancer cell migration and cancer development and/or metastasis. The compositions may be administered in vitro, in vivo, ex vivo, or in situ.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: IBEX-003/01WO_SeqList_ST25.txt, date recorded: Feb. 5, 2019, file size 15 kilobytes).

BACKGROUND

Phosphatase of Regenerating Liver 3 (PRL-3) is an oncogenic factor, the activation of which is often associated with tumorigenesis and metastasis. Previous studies have shown poly(rC) binding protein (PCBP1) decreases the expression of PRL-3, and may be able to inhibit the development of oncogenesis.

To realize the promise of novel gene therapies for cancer, the cancer cells must be manipulated so that cancer development and expression of biomarkers associated with tumorigenesis and metastasis are decreased or prevented. This will prevent development of cancer cells and/or keep them from becoming metastatic, and minimize the invasion of tissues and organs throughout the body.

SUMMARY OF THE INVENTION

The present disclosure provides methods of inhibiting tumor development, growth, cell migration, and/or metastasis by using gene therapy to transfect or/and transduce a cancer cell with a composition encoding a PCBP1 polypeptide, mutants, and/or variants thereof.

In some aspects the present disclosure provides methods of inhibiting, preventing, or decreasing cell migration comprising introducing a vector comprising a PCBP1 or a mutant PCBP1 nucleic acid sequence into a cell. In some embodiments, the cell migration is metastasis.

In some aspects, the present disclosure provides methods of treating cancer comprising introducing a vector comprising a PCBP1 or a mutant PCBP1 nucleic acid sequence into a cancer cell.

In some embodiments, the method is performed in vitro. In some embodiments, the method is performed ex vivo. In some embodiments, the method is performed in vivo.

In some embodiments, the cells are mammalian. In some embodiments, the mammalian cells are human. In some embodiments, the mammalian cells are organ cells, tissue cells, or blood cells.

In some embodiments, the mammalian cells are cancer cells. In some embodiments, the cancer cells are cells from melanoma, prostate, pancreatic, glioblastoma, retinoblastoma or a breast cancer.

In some embodiments, the mutant PCBP1 nucleic acid sequence encodes a polypeptide that cannot be phosphorylated or not fully phosphorylated compared to wild type PCBP1. In some embodiments, the mutant PCBP1 is not phosphorylated or not fully phosphorylated by p21-activating kinases (PAK).

In some embodiments, the mutant PCBP1 nucleic acid comprises one, two, three, four, or five or more mutations compared to wild type PCBP1 (SEQ ID NO: 1). In some embodiments, the mutant PCBP1 nucleic acid has at least 75% percent identity with wild type PCBP1 (SEQ ID NO: 1). In some embodiments, the mutant PCPB1 nucleic acid comprises the sequence of SEQ ID NO: 3. In some embodiments, the mutant PCBP1 nucleic acid comprises the sequence of SEQ ID NO: 5.

In some embodiments, the vector comprises a mutant PCBP1 nucleic acid sequence that encodes a mutant PCBP1 polypeptide. In some embodiments, the mutant PCBP1 polypeptide is not phosphorylated or not fully phosphorylated compared to wild type PCBP1. In some embodiments, the mutant PCBP1 polypeptide is not phosphorylated or is not fully phosphorylated by the P21-activated kinase-1 (PAK1). In some embodiments, the mutant PCBP1 inhibits or prevents phosphorylated PCBP1 production.

In some embodiments, the mutant PCBP1 polypeptide comprises one, two, three, four, five or more mutations compared to wild type PCBP1 (SEQ ID NO: 2). In some embodiments, the mutant PCBP1 polypeptide has at least 75% percent identity with wild type PCBP1 (SEQ ID NO: 2). In some embodiments, the mutant PCPB1 polypeptide comprises the sequence of SEQ ID NO: 4. In some embodiments, the mutant PCBP1 polypeptide comprises the sequence of SEQ ID NO: 6.

In some embodiments, the cell expresses multiple copies of a wild type or mutant PCBP1 nucleic acid sequence. In some embodiments, the cell expresses multiple copies of a wild type or mutant PCBP1 polypeptide.

BRIEF DESCRIPTION OF THE FIGURES

FIG. 1A shows a representative lentiviral vector containing wild type or mutant PCBP1 sequences. In this vector, PCBP1 is driven by an EF1a promoter and followed by a secondary expression cassette containing an IRES-GFP reporter gene cassette.

FIG. 1B shows a representative AAV vector containing wild type or mutant PCBP1 sequences. In this vector, expression of the PCBP1 sequence is driven by an EF1a promoter and followed by a secondary expression cassette containing an IRES-GFP reporter gene cassette. This vector can contain a WPRE fragment inserted after the GFP sequence to enhance the expression of the transgene(s).

FIG. 2A shows qRT-PCR analysis of gene expression in melanoma cells transfected with the compositions of the instant disclosure which measures the fold change between groups (ddct): GFP-only vs GFP plus wild type PCBP1 (wPCBP1_0) shows upregulation of PCBP1 with expression 4.012 fold higher GFP-only vs GFP plus PCBP1 S223L (mPCBP1_1) shows PCBP1 expression 3.97 higher and GFP-only vs GFP plus PCBP1 T60A & T127A (mPCBP1_2) shows PCBP1 expression 4.02 fold higher; respectively (*p<0.01). The housekeeping gene is GAPDH.

FIG. 7B shows a breast cancer cell (MCF-7) migration assay. The cell migration assays were read on day 1 and day 5, and were observed under the fluorescent microscope (green filter). (GFP: Green Fluorescent Protein). w PCBP1_0-GFP vector, mPCBP1_1 (one site mutation (c668t))-GFP vector; mPCBP1_2 (two site mutations (a178g & a379g))-GFP vector.

FIGS. 8A-E show a Breast cancer (MCF-7) dead cell assay after PCBP1 (wild type/mutants) or GFP (control) transfection. Dead cells were measured by removing the supernatant and applying a commercial live/dead cell assay kit. A: breast cancer cell density after GFP transfection and observation by bright field microscopy. B: breast cancer cell density after wild type PCBP1 transfection and observation by bright field microscopy. C: breast cancer cell density after mPCBP1_1 (one site mutation) transfection and observation by bright field microscopy. D: breast cancer cell density after mPCBP1_2 (two site mutations) transfection and observation by bright field microscopy. E: dead cell counts of breast cancer cells by fluorescent intensity measurement using a Microplate reader after transfection by PCBP1 (wild type/ mutants) and/or GFP vectors. (GFP: cell transfected by Green Fluorescent Protein. wP: cell transfected by wild type PCBP1. P1: cell transfected by mPCBP1 (one site mutation). P2: cell transfected by mPCBP1_2 (two site mutations).

FIGS. 20A-D show the staining of live and dead U87 glioblastoma cells after transfection by AAV-GFP (Panel A), AAV-PCBP1 (Panel B (wP)), AAV-PCBP1_1 (Panel C (Mu1)), or AAV-PCBP1_2 (Panel D (Mu2)).

FIGS. 23A-D show the staining of live and dead LN229 glioblastoma cells after transfection by AAV-GFP (Panel A), AAV-PCBP1 (Panel B (wP)), AAV-PCBP1_1 (Panel C (Mu1)), or AAV-PCBP1_2 (Panel D (Mu2)).

FIGS. 26A-B show live/dead analysis of the glioblastoma M059K cell line after transfection by AAV-GFP and AAV-PCBP1 and mutants. wP=wild type PCBP1; P1=mPCBP1_1; P2=mPCBP1_2. *$p<0.05$ compared with GFP.

FIGS. 30A-B show the measurement of pSTAT3 (Y705) protein levels by Western Blot in PCBP1-transfected LN299 glioblastoma cells. Cells were transfected with AAV-GFP (lane 1), AAV-PCBP1 (lane 2), AAV-mPCBP1_1 (lane 3), or AAV-mPCBP1_2 (lane 4). Treatment by all forms of PCBP1 down-regulated STAT3 levels in the glioblastoma cells, with mPCBP1_2 showing the most significant effect. (Panel A).

Panel B shows a repeat Western Blot measurement for lanes 1 and 2 in Panel A. Beta actin served as the internal control.

Figure 31A:
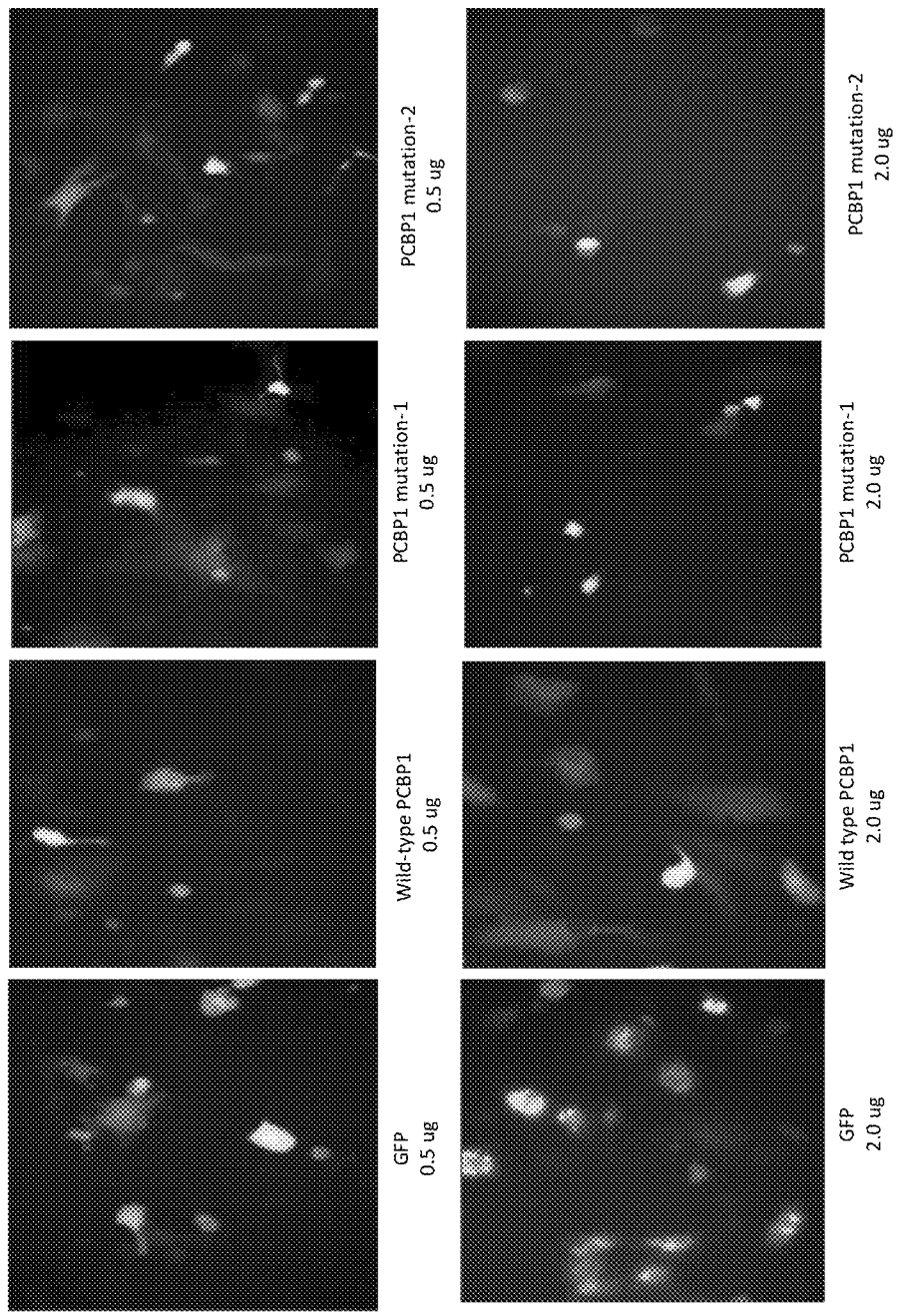
Figure 31B:
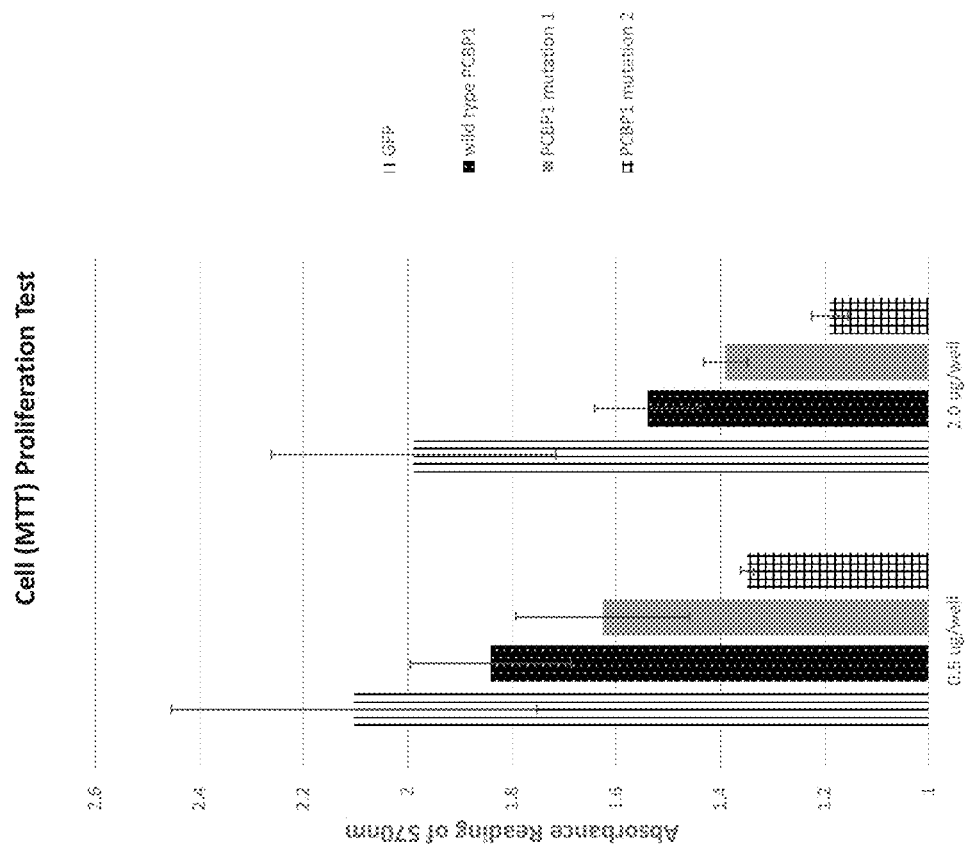

FIGS. 31A-B show the cell proliferation and counts of ovarian SKOV3 cells after transfection with PCBP1 or mutants. GFP=control vector; wild type PCBP=PCBP1; PCBP1 mutation-1=mPCBP1_1; PCBP1-mutation-2=mPCBP1_2. Panel A shows microscopic observation of the cells transfected with either 0.5 μg or 2.0 μg vector per well. Panel B shows the cell numbers as counted by a microplate reader.

Figure 32:
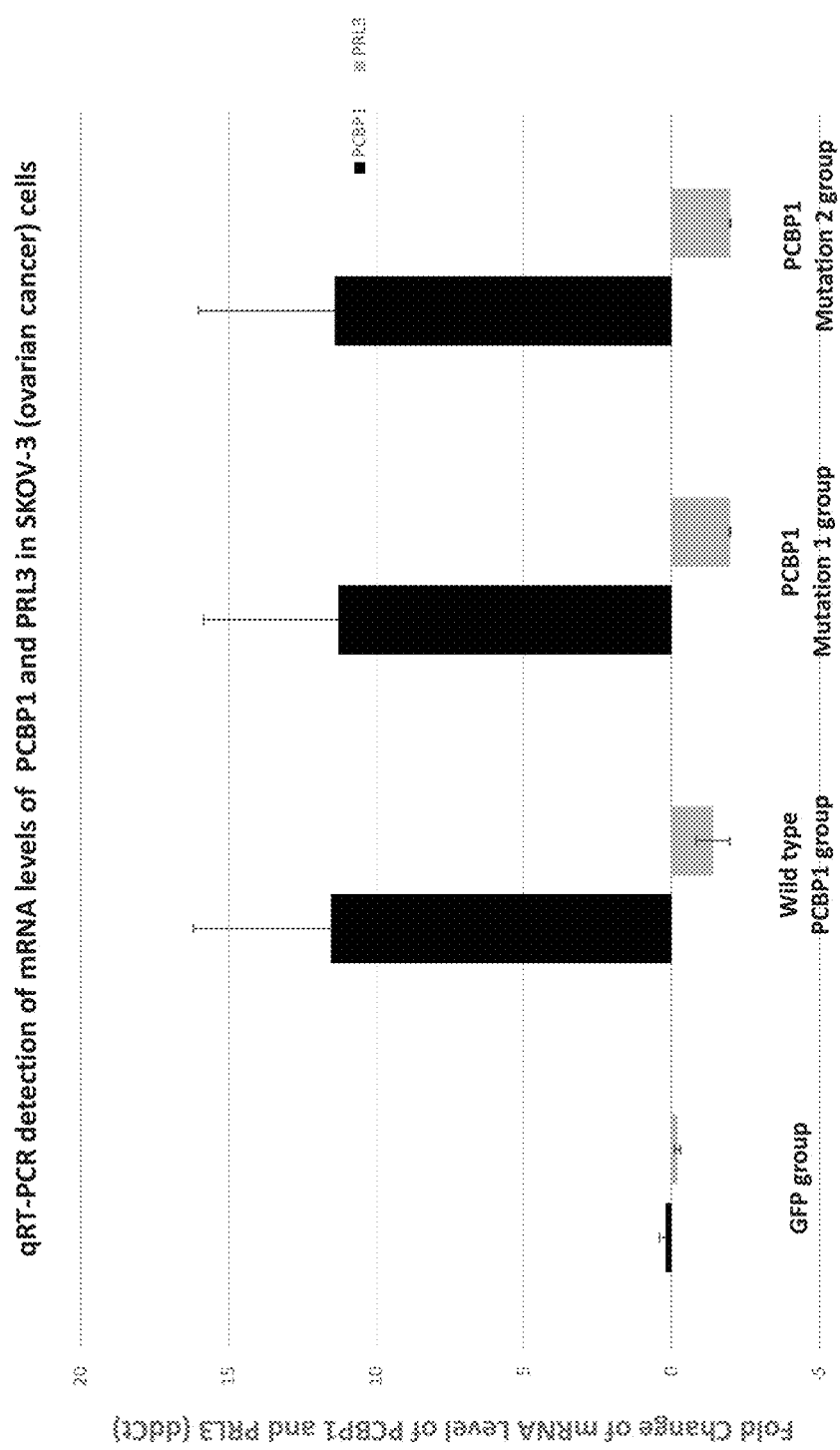

FIG. 32 shows the detection of mRNA expression levels of PCBP1 and PRL3 by qRT-PCR in SKOV3 ovarian cells after treatment. The graph shows comparisons of fold changes of mRNA levels (determined by qRT-PCR) among the treatment groups and control. PCBP1 mRNA expression levels show significant increases in all PCBP1 treatment groups, including wild type (11.5 fold increase), mPCBP1_1 (11.3 fold increase), and mPCBP1_2 (11.4 fold increase). In contrast, PRL3 mRNA levels decreased: wild type (1.403 fold decrease), mPCBP1_1 (1.978 fold decrease), and mPCBP1_2 (1.988 fold decrease). GFP=control vector; wild type PCBP1=PCBP1; PCBP1 mutation-1=mPCBP1_1; PCBP1-mutation-2=mPCBP1_2.

Figure 33:
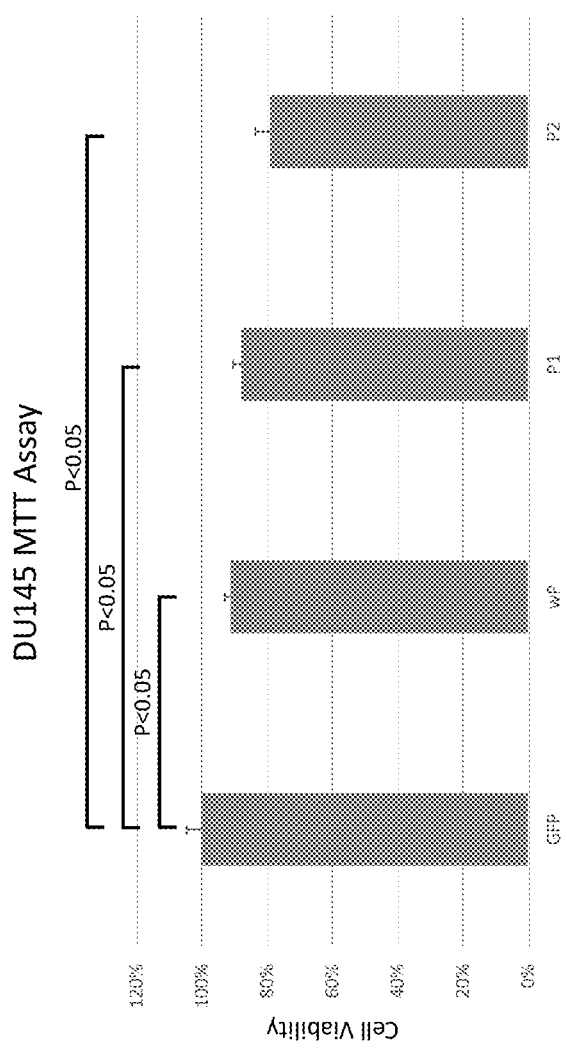

FIG. 33 shows the effect of wild type and mutant PCBP1 overexpression on the DU145 prostate cancer cell line proliferation. GFP=no PCBP1 treatment group; wP=wild type PCBP1; P1=mPCBP1_1; P2=mPCBP1_2. Overexpression of PCBP1 or the mutant forms significantly inhibited the proliferation of the prostate cancer cells compared to the control.

Figure 34:
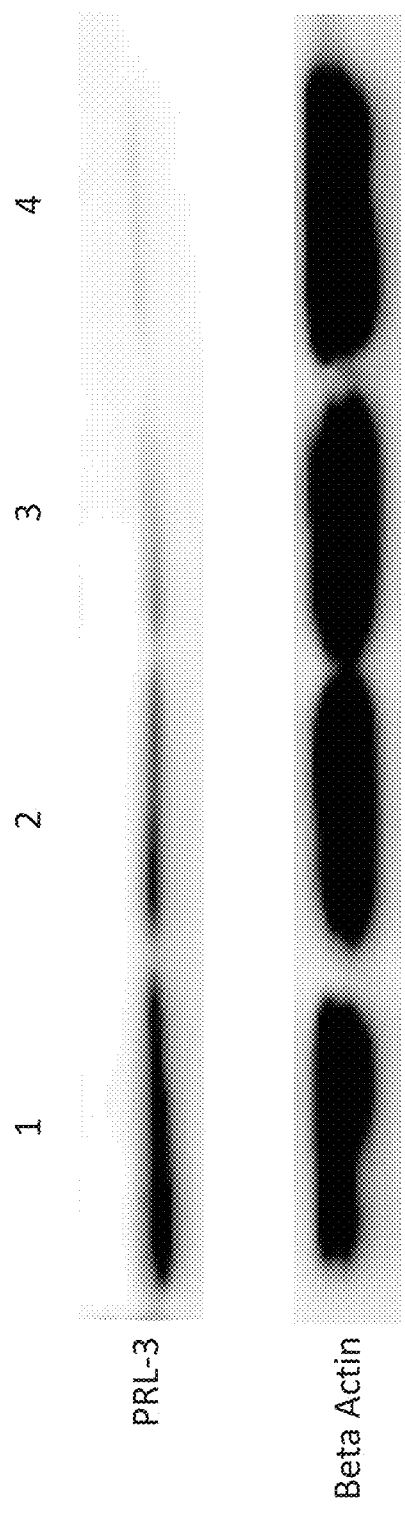

FIG. 34 shows the measurement of PRL3 protein levels by Western Blot in PCBP1-transfected DU145 prostate cancer cells. Cells were transfected with AAV-GFP (lane 1), AAV-PCBP1 (lane 2), AAV-mPCBP11 (lane 3), or AAV-mPCBP1_2 (lane 4). Treatment by all forms of PCBP1 down-regulated PRL3 levels in the prostate cancer cells, with mPCBP1_2 showing the most significant effect. Beta actin served as the internal control.

Figure 35:
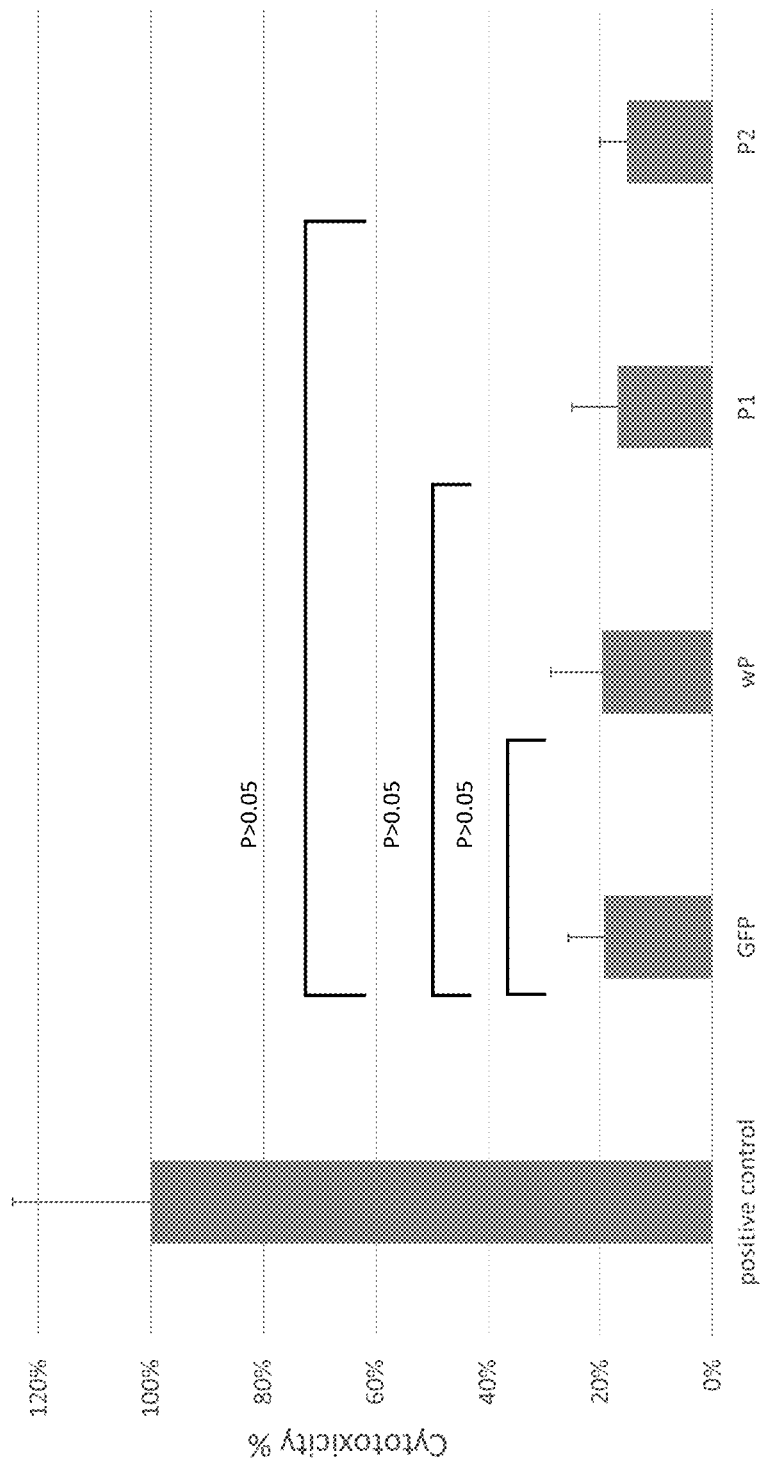

FIG. 35 shows a cytotoxicity (LDH) assay on a normal brain cell line, HCN-2. The HCN-2 cells were transfected with AAV-GFP, AAV-PCBP1 (wP), AAV-mPCBP1_1 (P1), or AAV-mPCBP1_2 (P2). There was no significant difference among the lactate dehydrogenase (LDH) in the treatment groups compared with the GFP control group ($p>0.05$), although a downward trend was observed. The cells in the positive control were treated by lysis buffer to elicit a maximum LDH release (left column). The experiments were performed in triplicate.

Figure 36B:
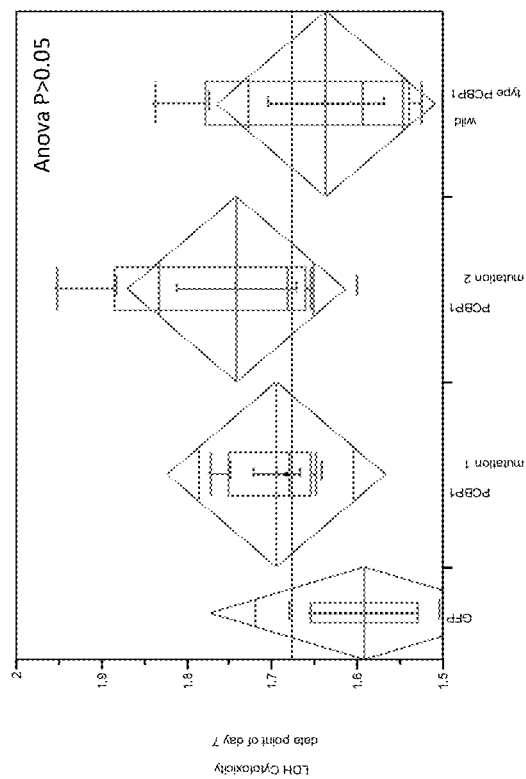
Figure 36A:
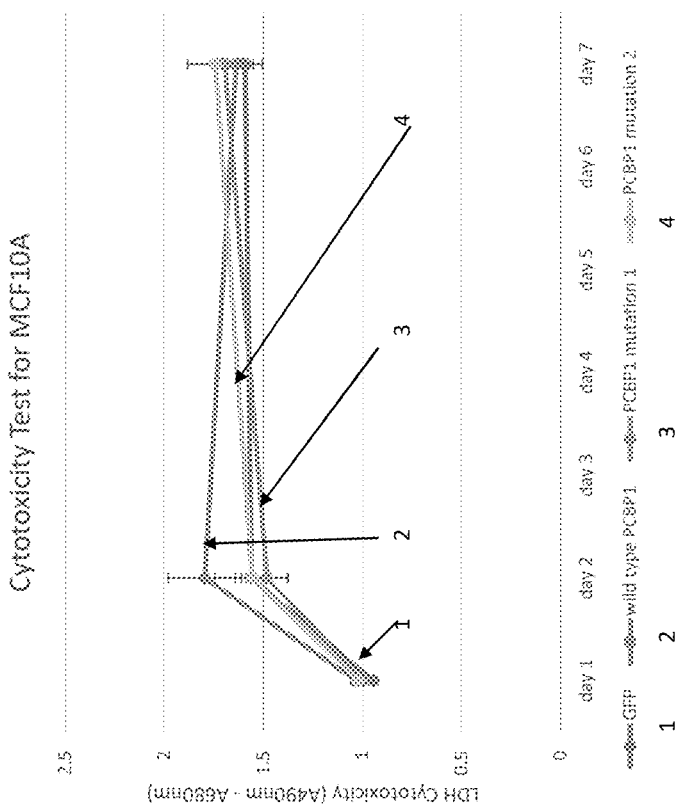

FIGS. 36A-B show a cytotoxicity (LDH) assay on a normal breast cell line, MCF10A. The MCF10A cells were transfected with AAV-GFP, AAV-PCBP1 (wP), AAV-mPCBP1_1 (P1), or AAV-mPCBP1_2 (P2). There was no significant difference among the lactate dehydrogenase (LDH) in the treatment groups compared with the GFP control group ($p>0.05$). (Panel A). No significant differences were observed among these four groups as tested by ANOVA ($p>0.05$). (Panel B). The treatment with wild type PCBP1, mPCBP1_1, or mPCBP1_2 is not cytotoxic to this normal breast cell line.

DETAILED DESCRIPTION

PRL-3 expression has been found to be elevated in metastatic cancers, including ovarian cancer, prostate, and gastric cancer, and overexpression of PRL-3 correlates with poorer liver cancer prognosis (Bardelli et al. 2003; Polato et al., 2005; Peng et al. 2004). Overexpression of PCBP1 has previously been shown to decrease PRL-3 expression (Wang et al., 2010). The present disclosure provides novel PCBP1 mutations and/or overexpressed PCBP1 which decrease PRL-3 expression to a greater degree than the wild type PCBP1 polypeptide or expression level, and thus decreases cell tumorigenicity and migration.

Thus, the compositions and methods disclosed herein include cells genetically modified (e.g. through transfection or transduction) with a mutant PCBP1 or an overexpressed PCBP1 to reduce or prevent cell migration and/or metastasis. A mutant PCBP1 sequence is incorporated into a vector system for gene therapy to directly prevent, inhibit, decrease, or delay cell migration for the treatment of disease.

Poly(rC)-Binding Protein 1 (PCBP1)

In some aspects, the present disclosure provides a vector containing the transcription factor Poly(rC)-binding protein 1 (PCBP1, also known as hnRNP-E1 and αCP1) which can inhibit or delay tumorigenesis and/or prevent cell growth or metastasis. In some embodiments, the PCBP1 is a mammalian PCBP1. In some embodiments, the PCBP1 is human PCBP1, mutant, fragment, or variant thereof. In some embodiments, the PCBP1 mutant, fragment, or variant thereof prevent or decrease phosphorylation of the expressed protein. In some embodiments, the PCBP1 is the mutant PCBP1_1 or PCBP1_2 as disclosed herein.

In some embodiments, the PCBP1 decreases cell proliferation or migration. In some embodiments, the PCBP1 decreases cell viability. In some embodiments, the PCBP1 increases cell death. In some embodiments, the PCBP1 affects growth and/or proliferation of immune cells. In some embodiments, the PCBP1 treats inflammation. In some embodiments, the inflammation is associated with cancer.

In some embodiments, the PCBP1 treats cancer. In some embodiments, the PCBP1 treats cancer by changing the expression and/or translation of a cancer biomarker associated with tumorigenesis or metastasis. In some embodiments, the PCBP1 decreases the expression and/or translation of a cancer biomarker associated with tumorigenesis or metastasis. In some embodiments, the cancer biomarker includes, but is not limited to, PRL-3, CD44 variant, E-cadherin, STAT-3, and vimentin. In some embodiments, the cancer biomarker associated with metastasis is PRL-3. In some embodiments the PCBP1 is an overexpressed wild type PCBP1 or a mutated PCBP1, that inhibits mRNA expression of PRL-3. In some embodiments, the PCBP1 is an overexpressed wild type PCBP1 or a mutated PCBP1, that inhibits protein expression of PRL-3.

In some embodiments, the PCBP1 decreases cell migration in genetically modified (e.g. transfected or transduced) cells. In some embodiments, the cell migration is metastasis.

In some embodiments, the mutant PCBP1 has no or decreased phosphorylation. In some embodiments, the mutant PCBP1 has no or decreased PAK phosphorylation. In some embodiments, the mutant PCBP1 inhibits or prevents phosphorylated PCBP1 production.

In some embodiments, the PCBP1 is an overexpressed wild type PCBP1. In some embodiments, the cell is transduced with one or more copy of wild type PCBP1. In some embodiments, the PCBP1 is a mutant. In some embodiments, the mutant PCBP1 is a single mutant. In some embodiments, the mutant PCBP1 is a double mutant. In some embodiments, the mutant PCBP1 is a triple mutant. In some embodiments, the mutant PCBP1 polypeptide comprises a S223L, T60A, and/or T127A mutation or a combination thereof. In some embodiments, the single PCBP1 mutant polypeptide is a S223L mutant (referred to herein as mPCBP1_1). In some embodiments, the double PCBP1 mutant polypeptide is a T60A & T127A mutant (referred to herein as mPCBP1_2).

In some embodiments, the PCBP1 is a nucleic acid. In some embodiments, the nucleic acid is DNA. In some embodiments, the nucleic acid is RNA. In some embodiments, the nucleic acid is mRNA. In some embodiments, the nucleic acid is cDNA. In some embodiments, the PCBP1 contains the nucleic acid sequence of SEQ ID NO: 1 or a mutant thereof. In some embodiments, the PCBP1 is the full-length nucleic acid sequence of SEQ ID NO: 1 or a mutant thereof. In some embodiments, the PCBP1 is a fragment of the nucleic acid sequence of SEQ ID NO: 1 or a mutant thereof. In some embodiments, the PCBP1 is a variant of the nucleic acid sequence of SEQ ID NO: 1 or a mutant thereof. In some embodiments, the mutant PCBP1 nucleic acid comprises a c668t, a178g and/or a379g mutation or a combination thereof. In some embodiments, the single PCBP1 mutant nucleic acid is a c668g mutant (referred to herein as mPCBP11). In some embodiments, the double PCBP1 mutant nucleic acid is a a178g & a379g mutant (referred to herein as mPCBP1_2).

Without being bound by theory, each of the KH domains within PCBP1 has been shown to bind to mRNAs of different proteins, and use of one or more KH domain may selectively inhibit the translation of a given protein. In some embodiments, the PCBP1 nucleic acid encodes all three K-homologous (KH) domains. In some embodiments, the PCPB1 nucleic acid encodes two KH domains. In some embodiments, the PCPB1 nucleic acid encodes one KH domain.

Further, mutations in a nuclear localization signal may alter the ability of PCBP1 to translocate into the nucleus, and thus affect later gene expression. In some embodiments, the PCBP1 contains a mutation in one or both nuclear localization signals. In some embodiments, the change in one or both nuclear localization signals inhibits the ability of PCBP1 to translocate into the nucleus.

Phosphorylation also plays a role in the activity of PCBP1 (e.g. nonphosphorylated PCBP1 may lack activity or demonstrate greater activity). In some embodiments, the PCBP1 nucleotide sequence contains a mutation(s) that affects the ability of the PCBP1 polypeptide to be phosphorylated. In some embodiments, the PCBP1 nucleotide sequence mutation(s) prevents PCBP1 polypeptide phosphorylation. In some embodiments, the nonphosphorylated PCBP1 or not fully-phosphorylated PCBP1 polypeptide is not active at wild type levels.

In some embodiments, the PCBP1 polypeptide is expressed from a polycistronic mRNA transcript. In some embodiments, the PCBP1 polypeptide is expressed from a dicistronic mRNA transcript. In some embodiments, the PCBP1 polypeptide is expressed as a fusion protein.

In some embodiments, the PCBP1 nucleotide sequence contains a point mutation(s) relative to wild type PCBP1 (SEQ ID NO: 1). In some embodiments, the PCPB1 nucleotide sequence contains a point mutation(s) that affects phosphorylation. In some embodiments, the PCBP1 point mutation increases phosphorylation. In some embodiments, the PCBP1 point mutation decreases phosphorylation. In some embodiments, the PCBP1 nucleotide sequence contains a mutation(s) that may affect nuclear membrane translocation. In some embodiments, the PCBP1 nucleotide sequence contains a point mutation(s) disclosed in Table 1.

In some embodiments, the point mutation is selected from the group including, but not limited to, G13A, G128C, A178G, T299C, T299A, G326A, A379G, G527A, C652T, C688T, G676A, G700A, G781T, T808G, G814T, A871G, C947T, G1033C, C1034T, G1048C, and/or A127G, or a combination thereof. In some embodiments, the point mutation that increases phosphorylation is selected from the group including, but not limited to, G13A, A178G, T299C, T299A, G326A, A379G, G527A, C652T, G781T, G814T, C947T, G1033C, C1034T, G1048C, and/or G1067T or a combination thereof. In some embodiments, the point mutation that decreases phosphorylation is selected from the group including, but not limited to, C688T, A127G, or G128C, A178G, and/or A379G or a combination thereof. In some embodiments, the point mutation is C668T, A178G, and/or A379G or a combination thereof.

TABLE 1

| Genome_Position | Position_N | Ref_N | Van_N | Position_A | Ref_A | Var_A | Cancer_Type | fraction |
| --- | --- | --- | --- | --- | --- | --- | --- | --- |
| chr2: 70314888-70314888 | 13 | G | A | 5 | V | M | DOID: 11054/ Urinary bladder cancer [UBC] | Gain\|Phosphorylation |
| chr2: 70314888-70314888 | 13 | G | A | 5 | V | M | DOID: 11054/ Urinary bladder cancer [UBC] | Gain\|Phosphorylation |
| chr2: 70314888-70314888 | 13 | G | A | 5 | V | M | DOID: 11054/ Urinary bladder cancer [UBC] | Gain\|Phosphorylation |
| chr2: 70314888-70314888 | 13 | G | A | 5 | V | M | DOID: 11054/ Urinary bladder cancer [UBC] | Gain\|Phosphorylation |
| chr2: 70315174-70315174 | 299 | T | C | 100 | L | P | DOID: 219/ Colon cancer [Colca] | Gain\|Phosphorylation |
| chr2: 70315174-70315174 | 299 | T | A | 100 | L | Q | DOID: 1521/ Cecum cancer [Cecca] | Gain\|Phosphorylation |
| chr2: 70315174-70315174 | 299 | T | A | 100 | L | Q | DOID: 219/ Colon cancer [Colca] | Gain\|Phosphorylation |
| chr2: 70315174-70315174 | 299 | T | A | 100 | L | Q | DOID: 1993/ Rectum cancer [Recca] | Gain\|Phosphorylation |
| chr2: 70315174-70315174 | 299 | T | A | 100 | L | Q | DOID: 1993/ Rectum cancer [Recca] | Gain\|Phosphorylation |

TABLE 1-continued

| Genome_Position | Position_N | Ref_N | Van_N | Position_A | Ref_A | Var_A | Cancer_Type | fraction |
|---|---|---|---|---|---|---|---|---|
| chr2: 70315174-70315174 | 299 | T | A | 100 | L | Q | DOID: 3571/ Liver cancer [Livca] | Gain\|Phosphorylation |
| chr2: 70315174-70315174 | 299 | T | A | 100 | L | Q | DOID: 219/ Colon cancer [Colca] | Gain\|Phosphorylation |
| chr2: 70315174-70315174 | 299 | T | A | 100 | L | Q | DOID: 219/ Colon cancer [Colca] | Gain\|Phosphorylation |
| chr2: 70315174-70315174 | 299 | T | C | 100 | L | P | DOID: 219/ Colon cancer [Colca] | Gain\|Phosphorylation |
| chr2: 70315174-70315174 | 299 | T | A | 100 | L | Q | DOID: 1993/ Rectum cancer [Recca] | Gain\|Phosphorylation |
| chr2: 70315174-70315174 | 299 | T | A | 100 | L | Q | DOID: 219/ Colon cancer [Colca] | Gain\|Phosphorylation |
| chr2: 70315201-70315201 | 326 | G | A | 109 | C | Y | DOID: 5041/ Esophageal cancer [EC] | Gain\|Phosphorylation |
| chr2: 70315402-70315402 | 527 | G | A | 176 | G | E | DOID: 4159/ Skin cancer [Skica] | Gain\|Phosphorylation |
| chr2: 70315527-70315527 | 652 | C | T | 218 | P | S | DOID: 11054/ Urinary bladder cancer [UBC] | Gain\|Phosphorylation |
| chr2: 70315527-70315527 | 652 | C | T | 218 | P | S | DOID: 11054/ Urinary bladder cancer [UBC] | Gain\|Phosphorylation |
| chr2: 70315543-70315543 | 668 | C | T | 223 | S | L | DOID: 11054/ Urinary bladder cancer [UBC] | Loss\|Phosphorylation |
| chr2: 70315543-70315543 | 668 | C | T | 223 | S | L | DOID: 11054/ Urinary bladder cancer [UBC] | Loss\|Phosphorylation |
| chr2: 70315543-70315543 | 668 | C | T | 223 | S | L | DOID: 11054/ Urinary bladder cancer [UBC] | Loss\|Phosphorylation |
| chr2: 70315656-70315656 | 781 | G | T | 261 | D | Y | DOID: 1793/ Pancreatic cancer [PACA] | Gain\|Phosphorylation |
| chr2: 70315689-70315689 | 814 | G | T | 272 | A | S | DOID: 1993/ Rectum cancer [Recca] | Gain\|Phosphorylation |
| chr2: 70315689-70315689 | 814 | G | T | 272 | A | S | DOID: 1993/ Rectum cancer [Recca] | Gain\|Phosphorylation |
| chr2: 70315689-70315689 | 814 | G | T | 272 | A | S | DOID: 1993/ Rectum cancer [Recca] | Gain\|Phosphorylation |
| chr2: 70315822-70315822 | 947 | C | T | 316 | A | V | DOID: 10534/ Stomach cancer [Stoca] | Gain\|Phosphorylation |
| chr2: 70315822-70315822 | 947 | C | T | 316 | A | V | DOID: 10534/ Stomach cancer [Stoca] | Gain\|Phosphorylation |
| chr2: 70315908-70315908 | 1033 | G | C | 345 | A | P | DOID: 1319/ Brain cancer [Braca] | Gain\|Phosphorylation |
| chr2: 70315908-70315908 | 1033 | G | C | 345 | A | P | DOID: 1319/ Brain cancer [Braca] | Gain\|Phosphorylation |
| chr2: 70315909-70315909 | 1034 | C | T | 345 | A | V | DOID: 363/ Uterine cancer [Uteca] | Gain\|Phosphorylation |
| chr2: 70315909-70315909 | 1034 | C | T | 345 | A | V | DOID: 363/ Uterine cancer [Uteca] | Gain\|Phosphorylation |
| chr2: 70315909-70315909 | 1034 | C | T | 345 | A | V | DOID: 363/ Uterine cancer [Uteca] | Gain\|Phosphorylation |
| chr2: 70315923-70315923 | 1048 | G | C | 350 | E | Q | DOID: 1324/ Lung cancer [Lunca] | Gain\|Phosphorylation |

TABLE 1-continued

| Genome_Position | Position_N | Ref_N | Van_N | Position_A | Ref_A | Var_A | Cancer_Type | fraction |
|---|---|---|---|---|---|---|---|---|
| chr2: 70315909 | 127/128 | A/G | G/C | 43 | S | A | Breast cancer[a] | Loss\|Phosphorylation |
| chr2: 70315909 | 178 | A | G | 60 | T | A | Breast cancer[b] | Loss\|Phosphorylation |
| chr2: 70315909 | 379 | A | G | 127 | T | A | Breast cancer[b] | Loss\|Phosphorylation |

[a]Brown, A (2016);
[b]Qingchang Meng, et al.

In some embodiments, the disclosure provides mimetics, analogs, derivatives, variants, or mutants of PCBP1 (SEQ ID NO: 1). In some embodiments, the mimetic, analog, derivative, variant, or mutant contains one or more nucleic acid substitutions compared to the nucleic acid sequence of the native PCBP1. In some embodiments, one to 20 nucleic acids are substituted. In some embodiments, the mimetic, analog, derivative, variant, or mutant contains about 1, about 2, about 3, about 4, about 5, about 6, about 7, about 8, about 9, or about 10 nucleic acid substitutions compared to the nucleic acid sequence of the native PCBP1 (e.g. SEQ ID NO: 1). In some embodiments, the mimetic, analog, derivative, variant, or mutant contains one or more nucleic acid deletions compared to the nucleic acid sequence of the native PCBP1 (e.g. SEQ ID NO: 1). In some embodiments, the mimetic, analog, derivative, variant, or mutant comprises SEQ ID NO: 3 (mPCBP1_1 (c668t)). In some embodiments, the mimetic, analog, derivative, variant, or mutant comprises SEQ ID NO: 5 (mPCBP1_2 (a178g & a379g).

In some embodiments, one to 20 nucleic acid residues are deleted compared to the nucleic acid sequence of the native PCBP1 (e.g. SEQ ID NO: 1). In some embodiments, the mimetic, analog, derivative, variant, or mutant has about 1, about 2, about 3, about 4, about 5, about 6, about 7, about 8, about 9, or about 10 nucleic acid residue deletions compared to the nucleic acid sequence of the native PCBP1 (e.g. SEQ ID NO: 1). In some embodiments, one to ten nucleic acid residues are deleted at either terminus compared to the nucleic acid sequence of the native PCBP1 (e.g. SEQ ID NO: 1). In some embodiments, one to ten nucleic acid residues are deleted from both termini compared to the nucleic acid sequence of the native PCBP1. In some embodiments, the nucleic acid sequence of the mimetic, analog, derivative, variant, or mutant is at least about 70% identical to the nucleic acid sequence of the native PCBP1. In some embodiments, the nucleic acid sequence of the mimetic, analog, derivative, variant, or mutant is about 70%, about 80%, about 85%, about 90%, about 95%, about 96%, about 97%, about 98%, or about 99% identical to the nucleic acid sequence of the native PCBP1 (e.g. SEQ ID NO: 1). Percentage identity can be calculated using the alignment program EMBOSS Needle.

In some embodiments, the PCBP1 is a polypeptide. In some embodiments, the PCBP1 contains the amino acid sequence of SEQ ID NO: 2. In some embodiments, the PCBP1 is the full-length amino acid sequence of SEQ ID NO: 2. In some embodiments, the PCBP1 is a fragment of the amino acid sequence of SEQ ID NO: 2. In some embodiments, the PCB1 is a variant of the amino acid sequence of SEQ ID NO: 2. In some embodiments, the PCBP1 variant includes the amino acid sequence of SEQ ID NO: 4 (mPCBP11 (S223L)). In some embodiments, the PCBP1 variant includes the amino acid sequence of SEQ ID NO: 6 (mPCBP1_2T60A & T127A). In some embodiments, the PCBP1 is a functional fragment or variant of the amino acid sequence of SEQ ID NO: 2. In some embodiments, the PCBP1 polypeptide contains all three K-homologous (KH) domains. In some embodiments, the PCPB1 polypeptide contains two KH domains. In some embodiments, the PCPB1 polypeptide contains one KH domain.

In some embodiments, the PCBP1 polypeptide contains one mutated K-homologous (KH) domain. In some embodiments, the PCBP1 polypeptide contains two mutated K-homologous (KH) domains. In some embodiments, the PCBP1 polypeptide contains three mutated K-homologous (KH) domains. In some embodiments, the mutation in the one or more KH domains effects RNA binding.

In some embodiments, the PCBP1 polypeptide sequence contains an amino acid mutation relative to wild type PCBP1 (SEQ ID NO: 2). In some embodiments, the PCPB1 polypeptide sequence contains an amino acid mutation that affects phosphorylation. In some embodiments, the amino acid mutation is selected from the group including, but not limited to, V5M, S43A, T60A, L100P, L100Q, C109Y, A127G, G128C, T237A, G176E, P218S, G226R, D234N, D261Y, Y270D, A272S, I291V, A316V, A345P, A345V, E350Q, S356I, or a combination thereof. In some embodiments, the mutation that increases phosphorylation is selected from the group including, but not limited to, V5M, L100P, L100Q, C109Y, G176E, D261Y, A272S, A316V, A345P, A345V, and/or E350Q or a combination thereof. In some embodiments, the mutation that decreases phosphorylation is selected from the group including, but not limited to, S43A, T60A, T127A, and/or S223L, or a combination thereof. In some embodiments, the amino acid mutation is T60A, S223L, S43A, and/or T127A.

In some embodiments, the disclosure provides mimetics, analogs, derivatives, variants, or mutants of PCBP1 (SEQ ID NO:2). In some embodiments, the mimetic, analog, derivative, variant, or mutant contains one or more amino acid substitutions compared to the amino acid sequence of the native PCBP1. In some embodiments, more than 20 amino acids are substituted. In some embodiments, one to 20 amino acids are substituted. In some embodiments, the mimetic, analog, derivative, variant, or mutant contains about 1, about 2, about 3, about 4, about 5, about 6, about 7, about 8, about 9, or about 10 amino acid substitutions or more compared to the amino acid sequence of the native PCBP1 (SEQ ID NO:2). In some embodiments, the mimetic, analog, derivative, variant, or mutant comprises SEQ ID NO: 4. In some embodiments, the mimetic, analog, derivative, variant, or mutant comprises SEQ ID NO: 6.

In some embodiments, the mimetic, analog, derivative, variant, or mutant contains one or more amino acid deletions compared to the amino acid sequence of the native therapeutic peptide agent. In some embodiments, more than 20 amino acids are deleted. In some embodiments, one to 20 amino acids are deleted compared to the amino acid sequence of the native protein agent. In some embodiments, the mimetic, analog, derivative, variant, or mutant has about 1, about 2, about 3, about 4, about 5, about 6, about 7, about 8, about 9, or about 10 amino acid deletions or more compared to the amino acid sequence of the native PCBP1 (SEQ ID NO:2). In some embodiments, one to ten amino acids are deleted at either terminus compared to the amino acid sequence of the native PCBP1 (SEQ ID NO:2). In some embodiments, one to ten amino acids are deleted from both termini compared to the amino acid sequence of the native PCBP1 (SEQ ID NO:2). In some embodiments, the amino acid sequence of the mimetic, analog, derivative, variant, or mutant is at least about 70% identical to the amino acid sequence of the native PCBP1 (SEQ ID NO:2). In some embodiments, the amino acid sequence of the mimetic, analog, derivative, variant, or mutant is about 70%, about 80%, about 85%, about 90%, about 95%, about 96%, about 97%, about 98%, or about 99% identical to the amino acid sequence of the native PCBP1 (SEQ ID NO:2). In some embodiments, the amino acid sequence of the mimetic, analog, derivative, variant, or mutant is about 70%, about 80%, about 85%, about 90%, about 95%, about 96%, about 97%, about 98%, or about 99% identical to the amino acid sequence of the native PCBP1 (SEQ ID NO:2) and retains all or most of the biological activity of the native PCBP1. In some embodiments, the amino acid sequence of the mimetic, analog, derivative, variant, or mutant is about 70%, about 80%, about 85%, about 90%, about 95%, about 96%, about 97%, about 98%, or about 99% identical to the amino acid sequence of the native PCBP1 (SEQ ID NO:2) and has reduced or altered activity compared with the native PCBP1.

In some embodiments, the amino acid sequence of the mimetic, analog, derivative, variant, or mutant is about 70%, about 80%, about 85%, about 90%, about 95%, about 96%, about 97%, about 98%, or about 99% identical to the amino acid sequence of one or more domains of the native PCBP1 (SEQ ID NO:2). In some embodiments, the amino acid sequence of the mimetic, analog, derivative, variant, or mutant is about 70%, about 80%, about 85%, about 90%, about 95%, about 96%, about 97%, about 98%, or about 99% identical to the amino acid sequence of one or more domains of the native PCBP1 (SEQ ID NO:2) and retains all or most of the biological activity of the native PCBP1. In some embodiments, the amino acid sequence of the mimetic, analog, derivative, variant, or mutant is about 70%, about 80%, about 85%, about 90%, about 95%, about 96%, about 97%, about 98%, or about 99% identical to the amino acid sequence of one or more domains of the native PCBP1 (SEQ ID NO:2) and has reduced or altered activity compared with the native PCBP1. Percentage identity can be calculated using the alignment program EMBOSS Needle. The following default parameters may be used for Pairwise alignment: Protein Weight Matrix=BLOSUM62; Gap Open=10; Gap Extension=0.1.

Vectors and Plasmids

Efficient delivery of the therapeutic gene to the target tissue or cell is the most significant hurdle for successful gene therapy. Since naked DNA is rapidly cleared or degraded in vivo by phagocytic immune cells or extracellular nucleases, a means of protecting the transgene may be desired. Furthermore, a vehicle for effecting tissue or cell entry is also required, due to the poor efficiency of spontaneous DNA uptake. Thus, DNA is normally combined with a gene delivery vehicle of some type, commonly known as a vector, to protect and mediate effective tissue or cell entry of the gene of interest.

Gene delivery systems can be grouped into non-biological (e.g. chemical and physical approaches of introducing plasmid DNA to mammalian cells) or biological (e.g. viruses and bacteria). Non-viral gene delivery systems normally involve the transfer genes carried on plasmid DNA. Plasmids employed do not generally replicate in mammalian cells.

Most commonly, recombinant viruses or naked DNA or DNA complexes are used. For example, viruses can be modified in the laboratory to provide vectors that carry corrected, therapeutic DNA into cells, where it can be integrated into the genome to alter abnormal gene expression and correct genetic disease. Alternatively, the vector may remain extrachromosomal and be expressed transiently.

In some aspects, the present disclosure provides methods of gene therapy using viral vectors. Viruses that may be used in gene therapy include, but are not limited to, lentiviruses, retroviruses, adenoviruses, adeno-associated viruses, replication-competent vectors, vaccinia virus, and the herpes simplex virus. Viral vectors that may be used in gene therapy include, but are not limited to, lentiviral, retroviral, adenoviruses, adeno-associated viruses vectors (AAV), replication-competent vectors, vaccinia virus vectors, and the herpes simplex virus vectors.

In some aspects, the present disclosure provides methods of gene therapy using non-viral vectors. In some aspects, the present disclosure provides methods of gene therapy using bacterial vectors. In some embodiments, the gene therapy method involves injection of naked nucleic acids (e.g. DNA or RNA). This may be performed using any appropriate means known in the art. In some aspects, the present disclosure provides methods of gene therapy using bacterial delivery systems. In some embodiments, the bacterial cells are live, attenuated, or killed. In some embodiments, the bacterial delivery system exploits a cell's ability to adhere to a mammalian cell or a secretion system to deliver the nucleic acid and/or proteins to the target mammalian cell. In some embodiments, the bacterial delivery system is selected from, but not limited to, *Salmonella typhi*, *Bifidobacterium* spp., *Salmonella choleraesuis*, *Vibrio cholera*, *Listeria monocytogenes*, *Escherichia coli*, *Streptococcus pyogenes*, and *Serratia marcescens*.

In some aspects, the present disclosure provides methods of gene therapy using non-viral and non-bacterial vectors. In some embodiments, the non-viral and non-bacterial vector is a eukaryotic vector. In some embodiments, the eukaryotic vector includes a transposon system, a CRISPR system, a Zinc-finger nuclease system, or a TALEN (transcription-activator-like effector nuclease). In some embodiments, the transposon system is selected from, but not limited to, the Sleeping Beauty or piggyBac or transposon system. In some embodiments, other methods for nucleic acid delivery may be used such as arginine-rich peptides or sonoporation.

In some aspects, the present disclosure provides methods of gene therapy using nanoparticles. In some embodiments, the nanoparticle is a lipid-based nanoparticle. In some embodiments, the lipid-based nanoparticle is a solid lipid-nanoparticle (SLN). In some embodiments, the lipid-based nanoparticle is a non-structured lipid carrier (NLC). In some embodiments, the nanoparticle is a polymer-based nanoparticle. In some embodiments, the polymer-based nanoparticle is a nanosphere or a nanocapsule.

Plasmid DNA-based vectors are commonly used in gene therapy and can accommodate large segments of DNA and allows the manipulation of a variety of regulatory elements that impact gene transfer and expression. At its most basic, an expression plasmid contains an expression cassette and backbone. The expression cassette is a transcriptional unit containing the gene or genes of interest and any regulatory sequences required for expression in the target cells. The backbone may contain a selectable marker (e.g. an antibiotic resistance gene or an auxotrophic selection gene) and an origin of replication required for the production of the plasmid in bacteria.

Any appropriate plasmid may be used in the methods disclosed herein. In some embodiments, the plasmid is a lentiviral vector. In some embodiments, the plasmid is an adeno-associated virus (AAV) plasmid. In some embodiments, representative plasmids are disclosed in FIGS. 1A-B. Any appropriate promoter may be used to drive expression of the genes in the expression cassette.

In some embodiments, the plasmid contains a retroviral promoter. In some embodiments, the plasmid contains a viral promoter. In some embodiments, the plasmid contains a mammalian promoter. In some embodiments, the mammalian promoter is a human promoter. In some embodiments, the promoter is tissue or cell specific. In some embodiments, the tissue specific promoter is selected from human transducing alpha-subunit promoter, GANT2, VMD2, human IRBP, K14, IRS2, and glial fibrillary acidic protein (GFAP) promoters. The promoter selected may be used as a chimeric promoter (e.g. with the interphotoreceptor retinoid binding protein (IRBP) promoter). In some embodiments, the tissue- or cell-specific promoter is specific for pancreatic cells, pancreatic beta cells, skin cells, keratinocytes, photoreceptor cells, epithelial cells, endothelial cells, and/or cancer cells (e.g. breast cancer cells, prostate cancer cells, leukemia cells, lymphoma cells, neural cancer cells, glioblastoma, etc.). In some embodiments, the promoter is specific for retinal or eye tissue or cells. In some embodiments, the promoter is specific for hematopoietic cells. In some embodiments, the promoter is specific for liver tissue or cells. In some embodiments, the promoter is specific for lung tissue or cells. In some embodiments, the promoter is specific for muscle tissue or cells. In some embodiments, the promoter is specific for HIV-infected cells.

In some embodiments, the promoter is an inducible promoter. In some embodiments, the promoter is induced by any appropriate composition or stimulus, including, but not limited to, doxycycline, tetracycline, IPTG, ecdysone, or rapamycin. In some embodiments, the inducible promoter is selected from any known to those skilled in the art, including but not limited to, a TRE3G, tetracycline, Lac, ecdysone, and rapamycin promoter. In some embodiments, the promoter is constitutive. In some embodiments, the promoter is a synthetic promoter or contains enhancer elements. In some embodiments, the promoter is a hybrid promoter. In some embodiments, the hybrid promoter contains regulatory regions of a gene.

In some embodiments, the promoter is selected from the group including, but not limited to, Ef1a, CAG, sv40, CMV, RSV, Oct4, Rex1, Nanog, GANT2, VMD2, hIRBP, TET promoter, CAAT Box, GC Box, GT-1 motif, I-box, AT-rich sequence, RBCS1, TRE3G, GAL1, Lap267, Rapamycin, CD11a, CD11b, CD18, Beta-globin promoter/LCR, Immunoglobulin promoter, PEPCK promoter, Albumin promoter, hAAT, SPC, SP-A, MCK, VLC1, HIV-LTR, Tat/Rev-responsive elements, Tat-inducible element, and FMR1.

In some embodiments, the plasmid contains all of the genes to be introduced via gene therapy. In some embodiments, the plasmid contains a PCBP1. In some embodiments, the PCBP1 is a mutant PCBP1. In some embodiments, the mimetic, analog, derivative, variant, or mutant comprises SEQ ID NO: 3. In some embodiments, the mimetic, analog, derivative, variant, or mutant comprises SEQ ID NO: 5. In some embodiments, the PCBP1 mimetic, analog, derivative, variant, or mutant encodes a polypeptide comprising the amino acid sequence of SEQ ID NO: 4 or SEQ ID NO: 6.

In some embodiments, introduction of the vectors of the disclosure increase gene copy number in the cell. In some embodiments, introduction of the vectors of the disclosure increase gene expression in the cell. In some embodiments, introduction of the vectors of the disclosure increase polypeptide expression in the cell. In some embodiments, the gene is PCBP1 or a mutant thereof.

Diseases and Disorders

The compositions and methods disclosed herein may be employed on any appropriate cell or tissue type. In some embodiments, the methods disclosed herein are performed in vitro. In some embodiments, the methods disclosed herein are performed ex vivo. In some embodiments, the methods disclosed herein are performed on isolated cells. In some embodiments, the methods disclosed herein are performed on cell culture. In some embodiments, the isolated cells or cell culture cells are taken from the subject and then implanted after transfection or transduction. In some embodiments, the cells are cancer cells.

In some embodiments, the compositions and methods disclosed herein are employed in vivo. In some embodiments, the methods disclosed herein are employed in situ. In some embodiments, the methods disclosed herein are used to decrease cell migration in any appropriate part of the body, including, but not limited to, the eye, retina, heart, blood, white blood cell, red blood cell, platelet, vitreous humor, sclera, retina, iris, cornea, skeletal muscle, cardiac muscle, smooth muscle, cartilage, tendon, bone, epidermis, organ, liver, heart, kidney, lung, stomach, gastrointestinal tract, colon, bladder, ovary, testes, pancreas, bone marrow, brain, neuron, and/or gland.

The compositions and methods disclosed herein may be used to treat, prevent, ameliorate, or delay any appropriate disease. For example, diseases that may be treated, prevented, ameliorated, or delayed are characterized by cell migration.

In some embodiments, the compositions and methods disclosed herein may be used to treat cancer or uncontrolled cell growth. In some embodiments, the compositions and methods disclosed herein are used to prevent, inhibit, ameliorate, or decrease metastasis, or uncontrolled cell migration. In some embodiments, the cancer is a solid cancer. In some embodiments, the cancer is a non-solid cancer. In some embodiments, the disclosure relates to cancers including, but not limited to, acute lymphoblastic leukemia (ALL), acute myeloid leukemia (AML), adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. glioblastoma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous t-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g. acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g. non-small cell, small cell), lymphoma (e.g. AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sézary syndrome, skin cancer (e.g. nonmelanoma, melanoma, Merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenström macroglobulinemia, and Wilms tumor. In some embodiments, the cells transfected or transduced with the compositions of the disclosure are obtained from one or more of these types of cancer.

Administration

The compositions of the present disclosure may be administered via any appropriate means. In some embodiments, the nucleic acid route of administration is transdermal, injection, intramuscular, subcutaneous, oral, nasal, intravaginal, rectal, transmucosal, enteric, parenteral, topical, epidural, intracerebral, Intracerebroventricular, intra-arterial, antra-articular, intradermal, intra-lesion, intraocular, intraosseous, intraperitoneal, intrathecal, intrauterine, intravenous, intra-vesical infusion, or intravitreal.

In some embodiments, the compositions or cells transfected or transduced with the compositions using the methods disclosed herein are administered to a patient. In some embodiments, the compositions or cells transfected or transduced with the compositions created using the methods disclosed herein are administered to a patient to treat, prevent, ameliorate, or delay the onset of a disease or disorder. In some embodiments, administration of the compositions disclosed herein prevent, decrease, ameliorate, or delay cell migration in the subject. In some embodiments, administration of the compositions disclosed herein prevent, decrease, ameliorate, or delay cell migration in the subject and treat, prevent, ameliorate, or delay the onset of a disease or disorder. In some embodiments, the disease or disorder is a cancer or metastatic cancer. In some embodiments, administration of the compositions disclosed herein decrease tumor mass/burden in a subject.

In some embodiments, the vectors, nucleic acids, or cells disclosed herein are administered once to a patient. In some embodiments, the vectors, nucleic acids, or cells disclosed herein are administered about 2 times, about 3 time, about 4 times, about 5 times, about 6 times, about 7 times, about 8 times, about 9 times, about 10 times, about 20 times, about 40 times, or more to a patient. Vectors, nucleic acids, or cells disclosed herein are administered until disease or disorder symptoms improve.

In some embodiments, administration of the vectors or nucleic acids disclosed herein prevent, ameliorate, decrease, or delay cell migration or proliferation in a treated patient compared to an untreated patient or the same patient before treatment. In some embodiments, cell migration or proliferation is prevented, ameliorated, decreased, or delayed in the treated patient between day 1 and year 10. In some embodiments, administration of the plasmids or vectors disclosed herein prevent, ameliorate, decrease, or delay cell migration or proliferation at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with cell migration or proliferation in an untreated patient or the same patient before treatment. In some embodiments, administration of the nucleic acids or vectors disclosed herein prevents, ameliorates, decreases, or delays cell migration or proliferation for about 1 day, about 1 week, about 1 month, about 2 months, about 3 months, about 4 months, about 5 months, about 6 months, about 1 year, about 2 years, about 5 years, or about 10 years, or more compared with cell migration or proliferation in an untreated patient or the same patient before treatment.

In some embodiments, cell migration or proliferation is decreased by about 1%, about 5%, about 10%, about 20%, about 30%, about 40%, about 50%, about 60%, about 70%, about 80%, about 90%, or about 100% compared with controls or patients or in vitro cells treated with other cell migration or proliferation inhibition methods. In some embodiments, administration of the nucleic acids, vectors, or cells disclosed herein reduces cell migration or proliferation by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients or in vitro cells treated with other cell migration or proliferation prevention/inhibition methods. In some embodiments, administration of the nucleic acids, vectors, or cells disclosed herein reduces cell migration or proliferation by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients or in vitro cells treated with other cell migration or proliferation prevention/inhibition methods.

In some embodiments, administration of the vectors or nucleic acids disclosed herein reduce tumor mass or burden in a treated patient compared to an untreated patient or the same patient before treatment. In some embodiments, tumor mass/burden is decreased in the treated patient between day 1 and year 10. In some embodiments, administration of the plasmids or vectors disclosed herein reduces tumor mass or burden at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with tumor mass or burden in an untreated patient or the same patient before treatment. In some embodiments, administration of the nucleic acids or vectors disclosed herein reduces tumor mass/burden for about 1 day, about 1 week, about 1 month, about 2 months, about 3 months, about 4 months, about 5 months, about 6 months, about 1 year, about 2 years, about 5 years, or about 10 years, or more compared with tumor mass or burden in an untreated patient or the same patient before treatment.

In some embodiments, tumor mass or burden is decreased by about 1%, about 5%, about 10%, about 20%, about 30%, about 40%, about 50%, about 60%, about 70%, about 80%, about 90%, or about 100% compared with controls or patients or in vitro cells treated with other tumor mass or burden reduction methods. In some embodiments, administration of the nucleic acids, vectors, or cells disclosed herein reduces tumor mass or burden by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients or in vitro cells treated with other tumor mass or burden reduction methods. In some embodiments, administration of the nucleic acids, vectors, or cells disclosed herein reduces tumor mass or burden by about 1%, about 5%, about 10%, about 20%, about 30%, about 40%, about 50%, about 60%, about 70%, about 80%, about 90, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients or in vitro cells treated with other tumor mass or burden reduction methods.

In some embodiments, the vectors, nucleic acids, or cells disclosed herein reduce cancer biomarker expression in treated cells in vitro. In some embodiments, administration of the vectors, nucleic acids, or cells disclosed herein reduces cancer biomarker expression in a treated patient. In some embodiments, administration of the vectors, nucleic acids, or cells disclosed herein reduce cancer biomarker expression in a treated patient or in vitro cells between day 1 and year 10. In some embodiments, administration of the nucleic acids, vectors, or cells disclosed herein reduces cancer biomarker expression at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients or in vitro cells treated with other cancer biomarker expression inhibition methods. In some embodiments, administration of the plasmids, vectors, or cells disclosed herein reduces cancer biomarker expression for about 1 day, 2 days, 3 days, 4 days, 5 days, 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years, or more compared with controls or patients or in vitro cells treated with other cancer biomarker expression inhibition methods.

In some embodiments, cancer biomarker expression is decreased by about 1%, about 5%, about 10%, about 20%, about 30a, about 40%, about 50%, about 60%, about 70%, about 80%, about 90%, or about 100% compared with controls or patients or in vitro cells treated with other cancer biomarker expression inhibition methods. In some embodiments, administration of the nucleic acids, vectors, or cells disclosed herein reduces cancer biomarker expression by about 1%, about 5%, about 10%, about 20%, about 30%, about 40%, about 50%, about 60%, about 70%, about 80%, about 90%, or about 100V at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients or in vitro cells treated with other cancer biomarker expression inhibition methods. In some embodiments, administration of the nucleic acids, vectors, or cells disclosed herein reduces cancer biomarker expression by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients or in vitro cells treated with other cancer biomarker expression inhibition methods.

In some embodiments, administration of the vectors, nucleic acids, or cells disclosed herein reduces metastasis in an in vitro or ex vivo organ or tissue. In some embodiments, administration of the vectors, nucleic acids, or cells disclosed herein reduces metastasis in a tissue, organ, or a treated patient. In some embodiments, administration of the vectors, nucleic acids, or cells disclosed herein reduces metastasis in a treated patient or in vitro or ex vivo organ or tissue between day 1 and year 10. In some embodiments, administration of the nucleic acids, vectors, or cells disclosed herein reduces metastasis at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients, or in vitro or ex vivo organ or tissue treated with other metastasis inhibition methods. In some embodiments, administration of the nucleic acids, vectors, or cells disclosed herein reduces metastasis or tumorigenesis for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years, or more compared with controls or patients, or in vitro or ex vivo organ or tissue treated with other metastasis inhibition methods.

In some embodiments, metastasis is decreased by about 1%, about 5%, about 10%, about 20%, about 30%, about 40%, about 50%, about 60%, about 70%, about 80%, about 90%, or about 100% compared with controls or patients treated with other metastasis inhibition methods. In some embodiments, administration of the nucleic acids, vectors, or cells disclosed herein reduces metastasis by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients or in vitro or ex vivo organ or tissue treated with other metastasis inhibition methods. In some embodiments, administration of the nucleic acids, vectors, or cells disclosed herein reduces metastasis by about 1%, about 5%, about 10%, about 20%, about 30%, about 40%, about 50%, about 60%, about 70%, about 80%, about 90%, or about 100% for about 1 day, about 2 days, about 3 days, about 4 days, about 5 days, about 6 days, about day 1, about day 2, about day 3, about day 4, about day 5, about day 6, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared controls or patients or in vitro or ex vivo organ or tissue treated with other metastasis inhibition methods.

In some embodiments, administration of the vectors, nucleic acids, or cells disclosed herein increases cell death in a tissue, organ, or a treated patient. In some embodiments, administration of the vectors, nucleic acids, or cells disclosed herein increases cell death in a treated patient or in vitro or ex vivo organ or tissue between day 1 and year 10. In some embodiments, administration of the nucleic acids, vectors, or cells disclosed herein reduces metastasis at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients, or in vitro or ex vivo organ or tissue treated with other cell-killing methods. In some embodiments, administration of the nucleic acids, vectors, or cells disclosed herein increases cell death for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years, or more compared with controls or patients, or in vitro or ex vivo organ or tissue treated with other cell-killing methods.

In some embodiments, cell death increases by about 1%, about 5%, about 10%, about 20%, about 30%, about 40%, about 50%, about 60%, about 70%, about 80%, about 90%, or about 100% compared with controls or patients treated with other cell-killing methods. In some embodiments, administration of the nucleic acids, vectors, or cells disclosed herein increases cell death by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients or in vitro or ex vivo organ or tissue treated with other cell-killing methods. In some embodiments, administration of the nucleic acids, vectors, or cells disclosed herein increases cell death by about 1%, about 5%, about 10%, about 20%, about 30%, about 40%, about 50%, about 60%, about 70%, about 80%, about 90%, or about 100% for about 1 day, about 2 days, about 3 days, about 4 days, about 5 days, about 6 days, about day 1, about day 2, about day 3, about day 4, about day 5, about day 6, about week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared controls or patients or in vitro or ex vivo organ or tissue treated with other cell-killing methods.

In some embodiments, administration of the nucleic acids, vectors, or cells disclosed herein reduce disease or disorder symptoms in a treated patient compared to an untreated patient or the same patient before treatment. In some embodiments, the disease or disorder symptoms are measured in a treated patient between day 1 and year 10. In some embodiments, administration of the nucleic acids, vectors, or cells disclosed herein reduces a disease or disorder symptom at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the disease or disorder symptom in an untreated patient or the same patient before treatment. In some embodiments, administration of the nucleic acids, vectors, or cells disclosed herein reduces a disease or disorder symptom for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years, or more compared with the disease or disorder symptom in an untreated patient or the same patient before treatment.

In some embodiments, the disease or disorder symptom is reduced by about 1%, about 5%, about 10%, about 20%, about 30%, about 40%, about 50%, about 60%, about 70%, about 80%, about 90%, or about 100% compared with the disease or disorder symptom in an untreated patient or the same patient before treatment. In some embodiments, administration of the nucleic acids, vectors, or cells disclosed herein reduces the disease or disorder symptom by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the disease or disorder symptom in an untreated patient or the same patient before treatment. In some embodiments, administration of the nucleic acids, vectors, or cells disclosed herein reduces the disease or disorder symptom by about 1%, about 5%, about 10%, about 20%, about 30%, about 40%, about 50%, about 60%, about 70%, about 80%, about 90%, or about 100% for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with the disease or disorder symptom in an untreated patient or the same patient before treatment.

In some embodiments, administration of the vectors or nucleic acids disclosed herein reduce cancer symptoms in a treated patient compared to an untreated patient or the same patient before treatment. In some embodiments, the cancer symptoms are measured in a treated patient between day 1 and year 10. In some embodiments, administration of the nucleic acids, vectors, or cells disclosed herein reduces a cancer symptom at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the cancer symptom in an untreated patient or the same patient before treatment. In some embodiments, administration of the nucleic acids, vectors, or cells disclosed herein reduces an cancer symptom for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years, or more compared with the cancer symptom in an untreated patient or the same patient before treatment.

In some embodiments, the cancer symptom is reduced by about 1%, about 5%, about 10%, about 20%, about 30%, about 40%, about 50%, about 60%, about 70%, about 80%, about 90%, or about 100% compared with the cancer symptom in an untreated patient or the same patient before treatment. In some embodiments, administration of the nucleic acids, vectors, or cells disclosed herein reduces the cancer symptom by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the cancer symptom in an untreated patient or the same patient before treatment. In some embodiments, administration of the nucleic acids, vectors, or cells disclosed herein reduces the cancer symptom by about 1%, about 5%, about 10%, about 20%, about 30%, about 40%, about 50%, about 60%, about 70%, about 80%, about 90%, or about 100% for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with the cancer symptom in an untreated patient or the same patient before treatment.

In some embodiments, the present disclosure provides methods to precisely track the cells transfected with the compositions of the disclosure. In some embodiments, these cells are traced to determine the behavior of the cells. In some embodiments, these cells are traced to determine their migration. In some embodiments, these cells are traced to determine their metastasis (or lack thereof). In some embodiments, these cells are traced to determine their response to any drugs administered either in vitro or in vivo. In some embodiments, the cells are also exposed to a therapeutic agent. In some embodiments, the therapeutic agent is a chemotherapeutic agent. In some embodiments the cells are exposed to the therapeutic agent in vitro. In some embodiments, the cells are exposed to the therapeutic agent in vivo.

Co-Administration

In some embodiments, the patient is subjected to additional therapies. In some embodiments, the patient is treated with a composition of the present disclosure as part of an anti-cancer therapy. In some embodiments, the anti-cancer therapy is selected from, but not limited to, radiation therapy, chemotherapy, immunotherapy, hormone therapy, stem cell transplant, and CAR-T therapy. The anti-cancer therapy may be administered before, at the same time, or after administration of the compositions of the disclosure.

Kits

The disclosure also provides kits for decreasing, preventing, ameliorating, or delaying cell migration or metastasis. In some embodiments, the kits include a vector or nucleic acid of the present disclosure. The kit can further include a label or printed instructions instructing the use of described reagents. The kit can further include a treatment to be tested. The kits are applied for in vitro and in vivo cell migration or metastasis prevention, decrease, amelioration, or delay.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein.

"Anti-oncogene" as used herein refers to any gene that prevents, delays, inhibits, or otherwise alters expression or activity of oncogenes. In some embodiments, the anti-oncogene is a tumor suppressing gene. In some embodiments, the anti-oncogene decreases expression of a cancer biomarker associated with metastasis.

It should be understood that singular forms such as "a," "an," and "the" are used throughout this application for convenience, however, except where context or an explicit statement indicates otherwise, the singular forms are intended to include the plural. All numerical ranges should be understood to include each and every numerical point within the numerical range, and should be interpreted as reciting each and every numerical point individually. The endpoints of all ranges directed to the same component or property are inclusive, and intended to be independently combinable.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

The term "about", as used herein to refer to a numerical quantity, includes "exactly" plus or minus up to 10% of that referenced numeric indication. When the term "about" is used in reference to a range of values, the term "about" refers to both the minimum and maximum value of the range (e.g., "about 1-50 µm" means "about 1 µm to about 50 µm").

The term "intimately associated", as used herein to describe the spatial relationship between two or more components of a composition refers to components that are intimately mixed, such as, for example, in mixtures, coatings and matrices.

The terms "transduction" and "transfection" are used interchangeably herein and refer to the introduction of genetic material into a cell. Any appropriate means of genetic modification is envisaged by the present disclosure.

This disclosure is further illustrated by the following non-limiting examples.

EXAMPLES

Example 1—Construction of Vectors Expressing PCBP1 Mutant Polypeptides

Studies have shown that mRNA expression of PRL-3 is elevated in metastatic cancers, including ovarian cancer, gastric cancer, and overexpression of PRL-3 negatively correlates with liver cancer prognosis (Bardelli et al. 2003; Polato et al., 2005; Peng et al. 2004). PCBP1 is known to regulate PRL-3 expression, with an inverse relationship between PCBP1 expression and PRL-3 expression which suggests PCBP1 may repress PRL-3 mRNA translation. The downregulation of PRL-3 is accompanied by the downregulation of the phosphorylated active form of Akt (pSer473) (Wang et al. 2010). For example, cancer cells that show an increase of Akt-2 (pSer474) phosphorylation also show a significant reduction in PCBP1 expression (Brown et al., 2016).

As shown in FIGS. 1A and 1B, a lentiviral gene therapy vector (LVV), or/and AAV systems containing a PCBP1 gene respectively were generated. This vector system contains the human elongation factor-1 alpha (EF1a) promoter and an IRES element which provides for internal initiation of protein translation from an mRNA molecule. A dicistronic mRNA is thus made where the IRES motif can initiate the independent and separate translation of a second gene from the single PCBPC-IRES-GFP mRNA. Several PCBP1 mutants were constructed that were designed to decrease phosphorylation of the protein by PAK1 based on the strategy below in Table 2. The PCBP1 mutant nucleotide sequences were cloned into the vector shown in FIG. 1A-B to create Vector A (mPCBP1_1, S223L) and Vector B (mPCBP1_2, T60A & T127A). The mutations in each PCBP1 mutant prevent PCBP1 phosphorylation by PAK1. Turn-on of the different genes is driven by the appropriate promoter(s). As PAK1 phosphorylates PCBP1 at both amino acids 60 and 127, mutation at these sites prevent PCBP1 phosphorylation by PAK1.

TABLE 2

Design of Mutant PCBP1

| Mutation Site | Position | Wild Type | Mutate to | DNA sequence (mutation region) | AA sequence (mutation region) | Vector |
|---|---|---|---|---|---|---|
| 1 | AA 223 (Nt. #668) | TCG (Ser) | TTG (Leu) | gcctac tTg attcaa (SEQ ID NO: 8) | AY L IQ (SEQ ID NO: 11) | Vector 1A/1B |
| 2 | AA60 (Nt. #178) | ACT (Thr) | GCT(Ala) | atcatc Gct ctg (SEQ ID NO: 9) | II A LT (SEQ ID NO: 12) | Vector 1A/1B |
| 3 | AA127 (Nt. #379) | ACG (Thr) | GCG (Ala) | gagagt Gcg ggggcg (SEQ ID NO: 10) | ES A GA (SEQ ID NO: 13) | Vector 1A/1B |

Figure 2B:
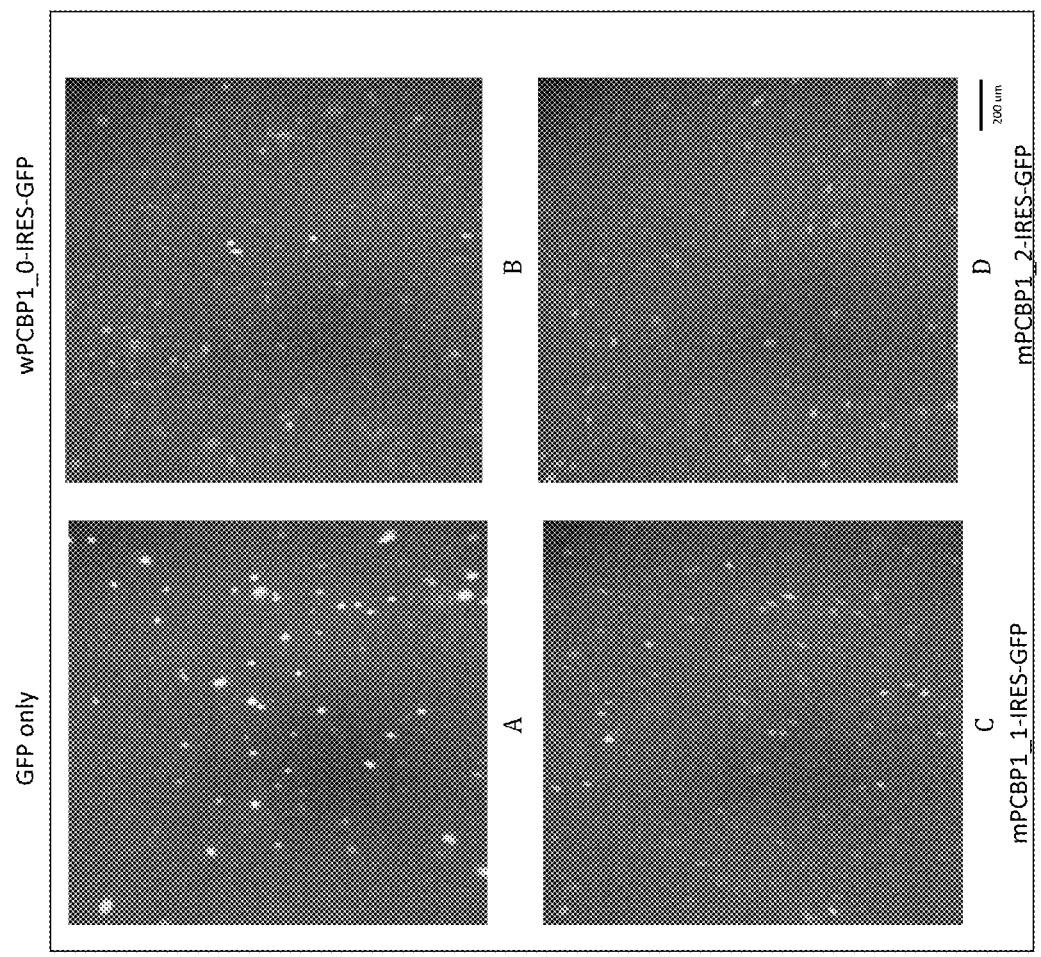
FIG. 2B shows GFP expression in melanoma cells after in vitro transfection of the therapeutic gene vectors of this disclosure. (A): GFP only; (B) wPCBP1_0-IRES-GFP; (C) mPCBP1_1-1RES-GFP; (D): mPCBP1_2-IRES-GFP. (Scale bar: 200 μm).

Example 2—the PCBP1 Mutants are Expressed at Levels Higher than Endogenous Wild Type To test whether the PCBP1 S223L and PCBP1 T60A & T127A mutations affected transcription levels, PCBP1 expression in melanoma cells was determined by qRT-PCR. FIG. 2 shows the analysis of fold change between groups (ddct). Comparison of GFP expression with wild type PCBP1 expression (wPCBP1_0) shows PCBP1 expression levels were greater by 4.012 fold. Comparison of GFP expression with expression of PCBP1 S223L (mPCBP1_1) shows PCBP1 S223L expression levels were greater by 3.97 fold. Comparison of GFP expression with expression of PCBP1 S223L mutant shows PCBP1 T60A & T127A (mPCBP1_2) expression levels were greater by 4.02 fold. The wild type PCBP1 and two mutant forms display similar mRNA expression. The housekeeping gene used in this assay is GAPDH.

Example 3—Expression of PCBP1 in Melanoma Cells

Melanoma cells were split into four groups and each group was transfected in vitro with vectors containing A) GFP only; B) wild type PCBP1 (wPCBP1_0-IRES-GFP) and GFP; 3) PCBP1 S223L and GFP (mPCBP1_1-IRES-GFP); or D) PCBP1 T60A & T127A (mPCBP1_2-IRES-GFP). 24-48 hours after transfection of lentiviral vectors containing either wild-type PCBP1 or mutant PCBP1 using the lipofectamine kit (Invitrogen Inc.), expression of GFP was observed (FIG. 2). Transfection rates were each around 90% (data not shown). Variation in GFP expression levels may be due to the different vectors. Without being bound by theory, in the vectors, PCBP1 is upstream of the GFP. When PCBP1 efficiency is 100%, the downstream gene (GFP) will show a lower expression efficiency (e.g. around 60%-80%). As the control vector contains only GFP and no PCBP1 sequence, the GFP expression efficiency is higher. There is no evidence indicating that PCBP1 and GFP interact with each other.

Figure 6:
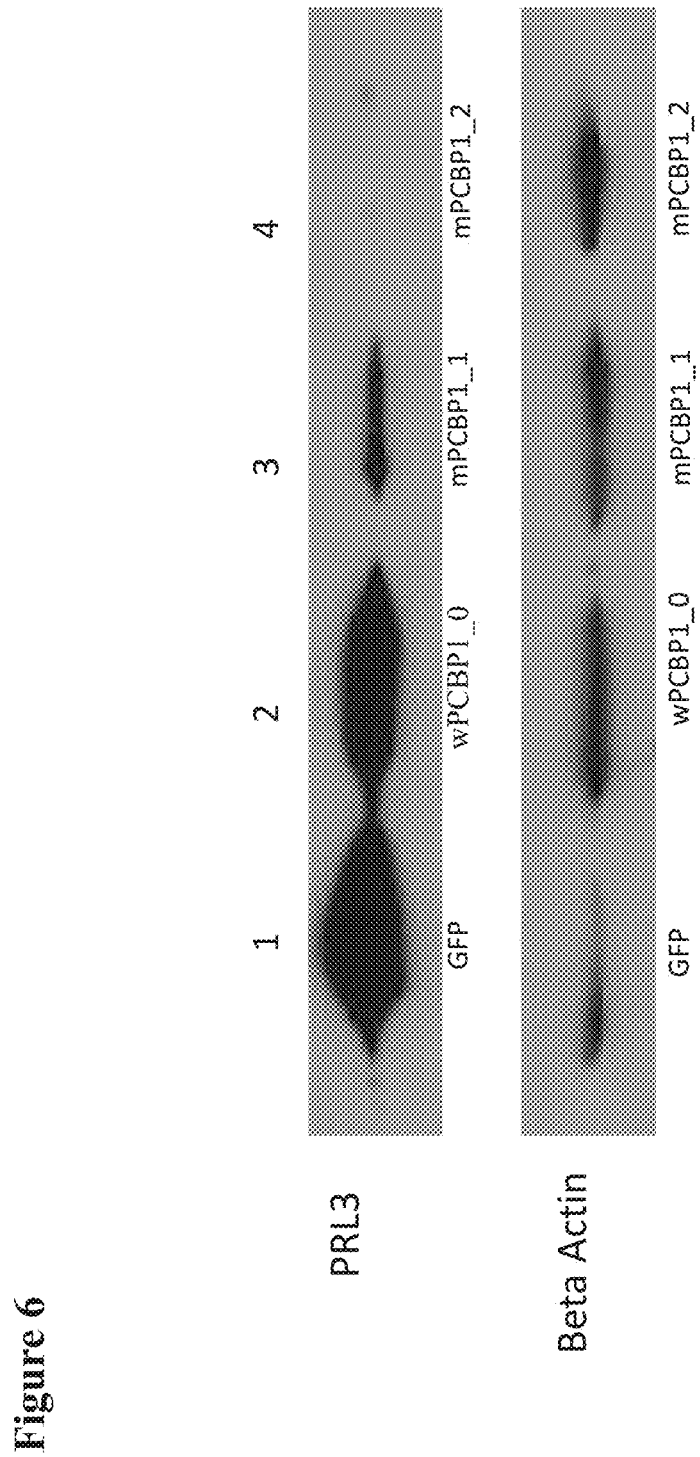
FIG. 6 shows a Western Blot analysis of PRL3 protein levels in transformed breast cancer (MCF-7) cells after treatment with vectors encoding GFP only (lane 1); wPCBP1_0 (lane 2); mPCBP1_1; (lane 3); and mPCBP1_2 (lane 4).

For the Western Blot, briefly after PCPB1 treatment, the cell culture dishes were placed on ice and the cells were washed with ice-cold PBS three times. Ice-cold lysis buffer (containing a protease inhibitor) was then added to the cells. Adherent cells were scraped off the dishes and the cell suspension was transferred into a pre-cooled microcentrifuge tube, which was constantly agitated for 30 minutes at 4° C. and then centrifuged. After centrifugation, the tubes were placed on ice, the supernatant aspirated to a fresh tube, and the pellet was discarded. After protein quantification, the protein concentration of each cell lysate was determined by adding an equal volume of 2× Laemmli sample buffer. The sample was boiled in this sample buffer at 100° C. for 5 minutes. Equal amounts of protein from the treatment and control groups were loaded into each well of an SDS-PAGE gel, along with a molecular weight marker. The protein concentrations tested ranged from about 20-30 μg from the cell lysate or tissue homogenate, or about 10-100 ng of purified protein. The gel was electrophoresed for 1-2 hours at 100V. The proteins on the gel were then transferred to an active nitrocellulose membrane using transfer buffer and the Bio-Rad Semi-Transfer system (Bio-Rad, CA). The membrane was blocked by using the blocking buffer for 1 hour at room temperature or overnight at 4° C., and then washed 3 times (5 min/per each washing) with TBST buffer before starting antibody staining. The membrane was then incubated with the chemiluminescence substrate for about 5 min to visualize the protein signal following the kit manufacturer's recommendation (See FIG. 3 and FIG. 6).

Figure 3:
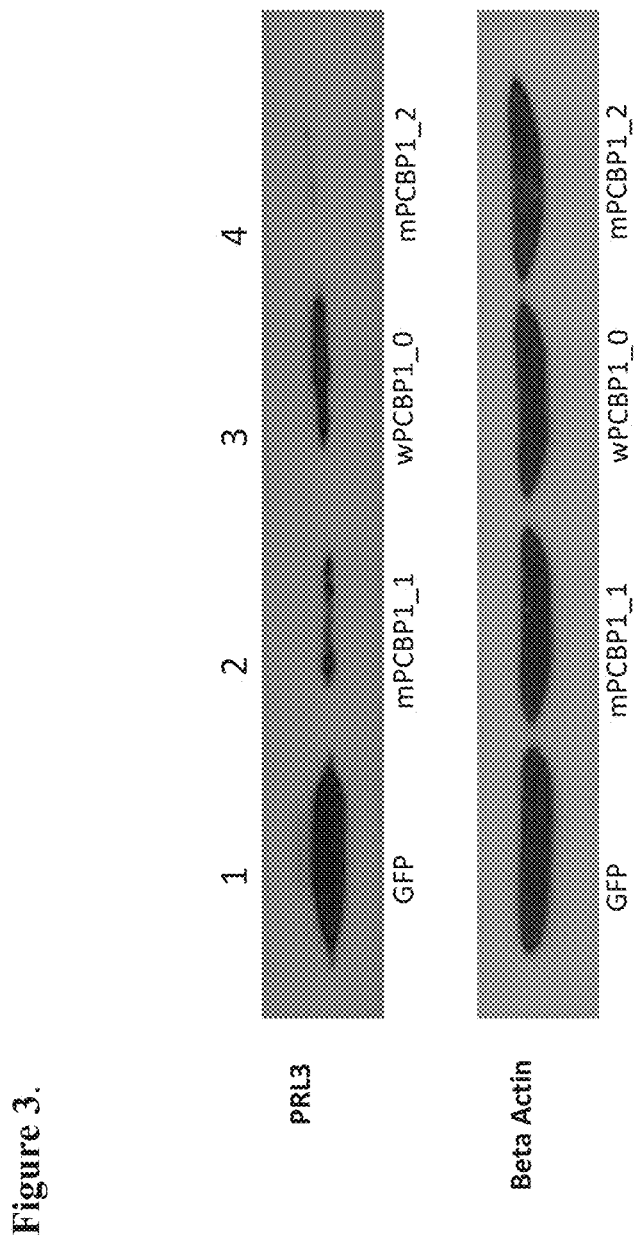
FIG. 3 shows PRL-3 protein expression by Western Blot analysis after treatment by gene therapy vectors encoding different forms of the PCBP1 (wild-type and mutants) genes in melanoma cells. Lane 1: GFP only; Lane 2: mPCBP1_1+ GFP; Lane 3: wPCBP1_0+GFP; Lane 4: PCBP1_2+GFP. Beta-actin is the control.

FIG. 3 shows the PRL-3 protein expression in the cells transfected with the gene therapy vectors encoding different forms of PCBP1. As shown in FIG. 3, transfection of the melanoma cell with vector containing wild type PCBP1 decreases PRL-3 expression compared with the GFP-only vector. Transfection of the cells with a vector containing either of the PCBP1 mutants decreases PRL-3 expression even further, with the double PCBP1 T60A & T127A mutant decreasing PRL-3 expression to an even greater degree than transfection with the single PCBP1 S223L mutant.

Example 4—Transfection with Mutant PCBP1 Decreases Melanoma Cell Migration

The effect of the mutant, de-phosphorylated PCBP1 mutants on cell migration was tested using a cell migration assay. Briefly, melanoma cells transfected with GFP only, wild type PCBP1 (wPCBP1_0-IRES-GFP) and GFP, or PCBP1 T60A & T127A (mPCBP1_2-IRES-GFP) were observed for five days post-transfection.

The same number of cells from each treatment group or/and control was seeded onto 24 (or 6) well-plates for transfection by the vector encoding a marker protein (i.e. GFP) using the lipofectamine kit (Invitrogen Inc). The cells transfected with GFP were then suspended by medium containing trypsin (0.1%), and washed by culture medium. The same amount of the cell numbers (e.g. about 80,000 cells from each individual group) was then re-placed and evenly distributed onto the Oris migration assay plate (Oris Cell Migration Assay kit) with a loading volume of 100 μl containing the same amount of cell numbers into each well of the 96 well-plate. Each well of the dish containing the Oris™ Cell Seeding Stoppers (OCS) was then incubated in a humidified chamber (37° C., 5% CO2) for 5 to 10 hours (cell line dependent) to permit cell attachment. Before counting the cells, the OCS was removed by using an Oris™ Stopper tool to create the areas termed "Circle Detection Zone (CDZ)" for detecting any new cells that migrated to inside this CDZ as new migration cells. Those cells expressing the GFP in the CDZ were then counted at each timepoint using the microplate reader (Molecular Devices, LLC) or/and under a fluorescent microscope (BD Biosciences).

Cells were visualized and analyzed by fluorescence microscopy of the GFP expression. The GFP reflects the expression of the genes in each transfected cell, although the intensity of the GFP may decrease the level of intensity along with the time, although as shown in the results, not much fluorescence intensity was lost over 5 days. The total cells displaying intensity for each well was measured at the same time (day) point (e.g. Day 0 or Day 5). As the cells with GFP were transduced by the vector encoding the genes including GFP, and not by immunostaining with a fluorescent dye, the fluorescent signal is not detached from the substrate. Those cells not displaying a fluorescent signal are not transfected with the vectors of the disclosure and are therefore not counted and limited out in this analysis.

Figure 4A:
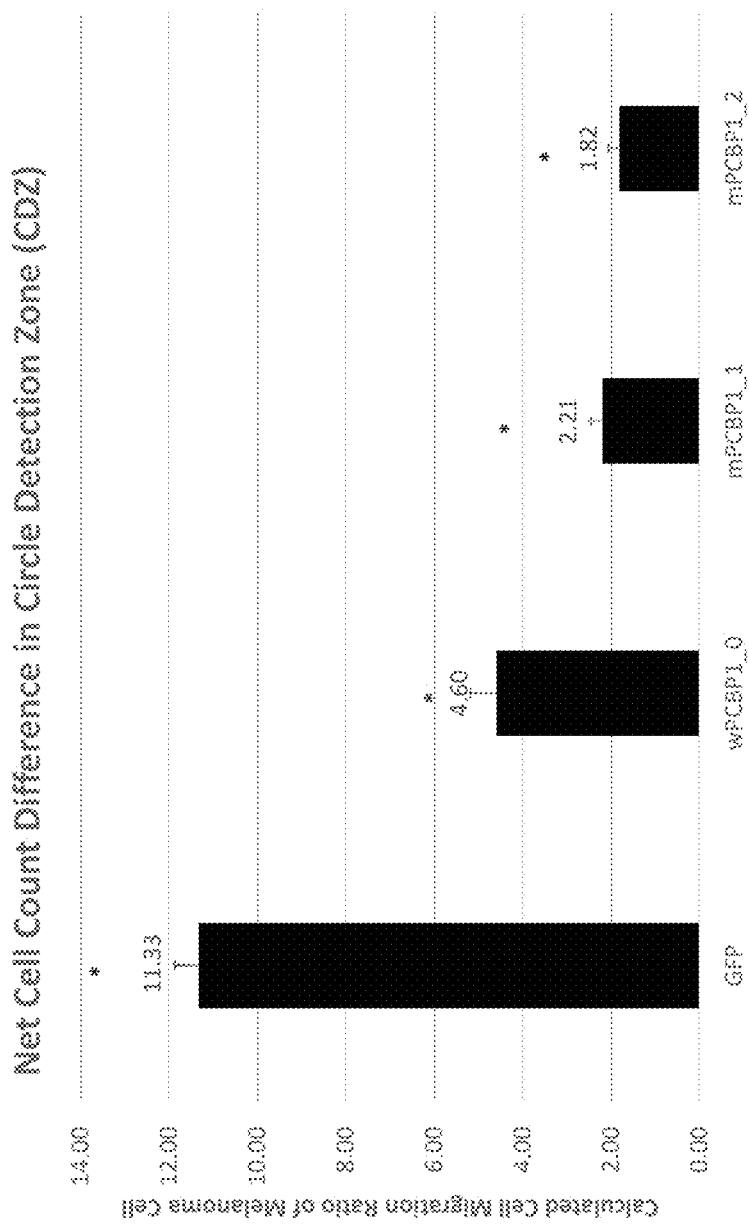
FIG. 4A shows the comparison of the net cell count difference in Circle Detection Zone (CDZ) as a percentage of migrated cells compared to all cells in the well to demonstrate the migration of transfected melanoma cells. The percentage of migrated cells (per well) in GFP group (11.33) was significantly higher than wPCBP1_0 (wild type PCBP1, also referred to herein as "PCBP1"), mPCBP1_1, and mPCBP1_2. Among these three groups, mPCBP1_2 has lowest percentage of migrated cells in per well (1.82). (* P<0.05).
Figure 4B:
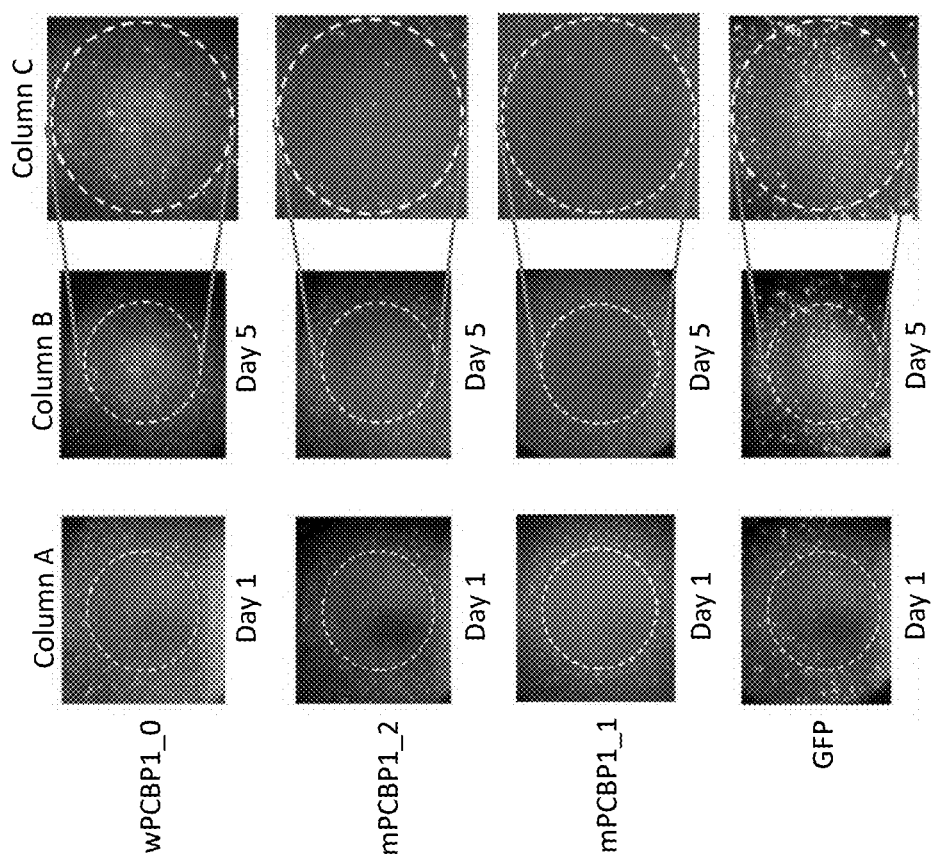
FIG. 4B shows a cell migration assay. The cell migration assays were read on day 1 and days 5 and were observed under the fluorescent microscope (green filter). The top row shows cell migration of wPCBP1_0 from day 1 and days 5; the middle rows show mPCBP1_2 and mPCBP1_1, and the bottom row shows the GFP group. Column A is cell migration well (white dotted line circle is Circle Detection Zone, or called CDZ) on day 1; column B is cell migration well on day 5 (with CDZ in white dotted line); column C is enlarged CDZ in column B.
Figure 4C:
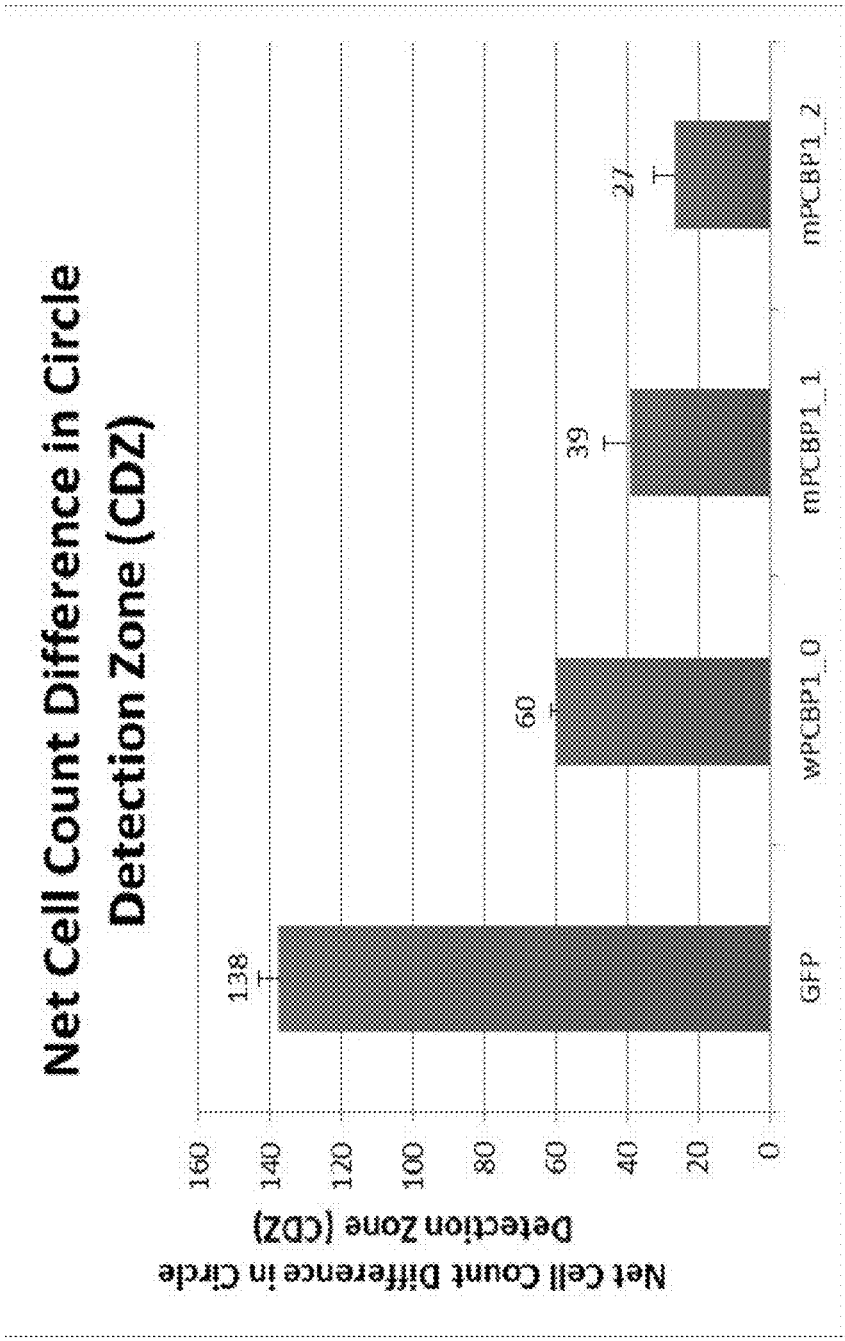
FIG. 4C shows the net cell count difference in the Circle Detection Zone (CDZ) Migration Assay as a comparison of the difference among the net cell counts in the CDZ from day 1 to day 5. The melanoma cells were transfected by GFP, wPCBP1_0, mPCBP1_1, or mPCBP1_2.
Figure 5:
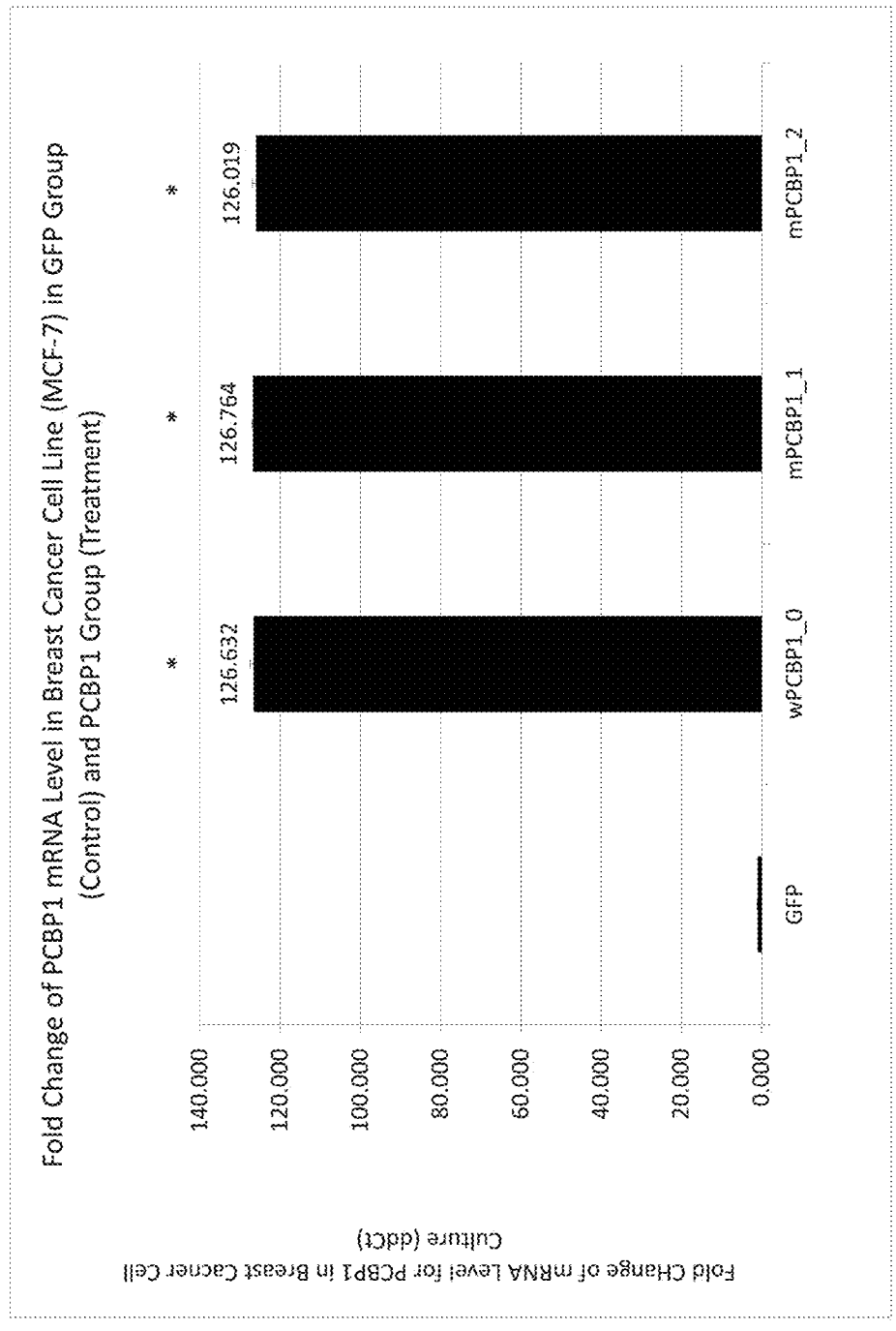
FIG. 5 shows the fold change of PCBP1 mRNA levels in a breast cancer (BC) Cell line (MCF-7). The graph shows qRT-PCR results of PCBP1 mRNA fold change in PCBP1 (WT/mutants) or GFP-only vector transfected into MCF-7. Compared with the GFP-only group, all PCBP1+GFP groups (WT and mutants) show a significant increase of PCBP1 mRNA expression levels in the breast cancer cell (fold change indicated in figure, *P<0.01). (GFP: Green Fluorescent Protein vector. w PCBP1_0-GFP vector, mPCBP1 (one site mutation (c668t));mPCBP1_2 (two site mutations (a178g & a379g)).

The results of this cell migration assay are demonstrated in FIG. 4A-C. In FIG. 4B, the white dotted line circle is the Circle Detection Zone (CDZ). Column A is Day 1; Column B is cell migration well in day 5 (with the CDZ in a white dotted line); Column C is the enlarged CDZ from Column B. Table 3 shows the quantified data from the cell migration assay which demonstrates the double T60A&T127A mutant exhibited a decreased net cell migration in the CDZ compared with both wild type PCBP1 and the GFP-only cells.

TABLE 3

Calculation of Net Cell Migration of melanoma cells into CDZ

| Vector | Net Cell Migration in CDZ | Std |
|---|---|---|
| GFP | 138 | 7.071 |
| wPCBP1_0 | 60 | 7.778 |

TABLE 3-continued

Calculation of Net Cell
Migration of melanoma cells into CDZ

| Vector | Net Cell Migration in CDZ | Std |
|---|---|---|
| mPCBP1_1 (S223L) | 39 | 2.828 |
| mPCBP1_2 (T60A & T127A) | 27 | 6.364 |

FIGS. 4A-4C show the cell migration adjusted to percentage of cells per well. The percentage of migrated cells (per well) in the GFP group (11.076) was significantly higher than that of wild type PCBP1 (wPCBP1_0) and PCBP1 T60A & T127A (mPCBP1_2). Among these three groups, mPCBP1_2 displayed the lowest percentage of migrated cells per well (2.082). These values were calculated as follows:

In each time point, the total cells were detected by microplate reader (as a base denominator). Cells were also counted in the region of circle detection zone (CDZ) as migrated cells per time point (as the numerator). The adjusted net cell difference in the CDZ was calculated according to the formula shown as below:

$$\text{Percentage of migrated cells per well (\%)} = \frac{\text{Day 5 of cells counted in the } CDZ}{\text{Day5 of total cells signals by microplate Reader per well}} - \frac{\text{Day 0 of cells counted in the } CDZ}{\text{Day 0 of total cells signals by microplate Reader per well}}$$

Figure 7A:
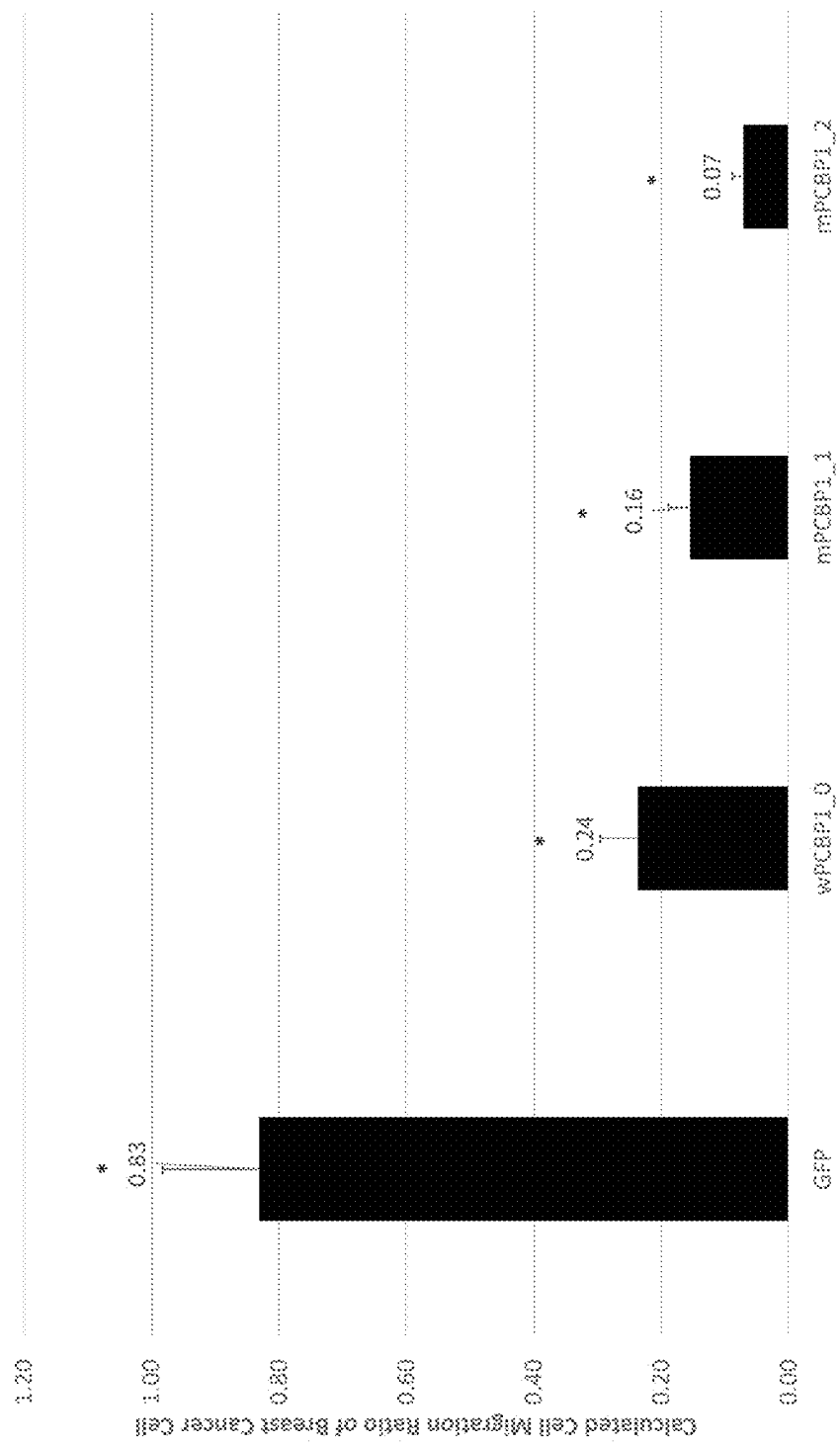
FIG. 7A shows a comparison ratio of the differences for net cells counted in Circle Detection Zone (CDZ) and the fluorescence intensity of the total cells per well.
Figure 7C:
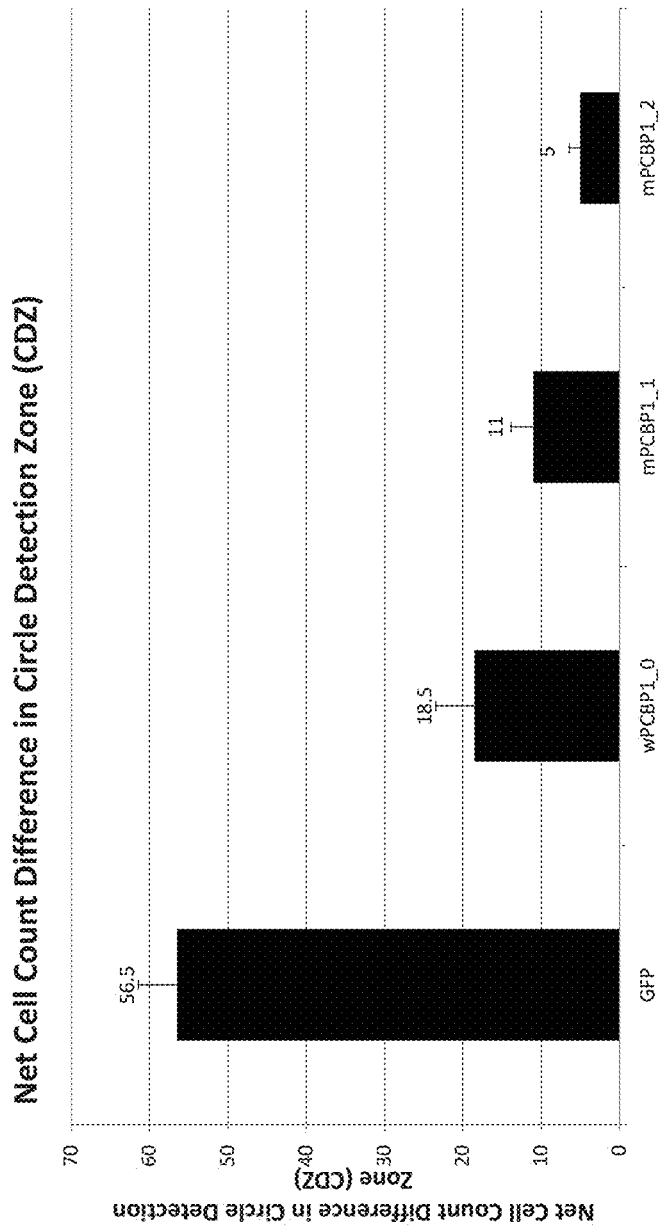
FIG. 7C shows Cell Migration Assay on breast cancer cell (MCF-7) transfected by GFP, wPCBP1_0, mPCBP1, or mPCBP1_2.
Figure 8E:
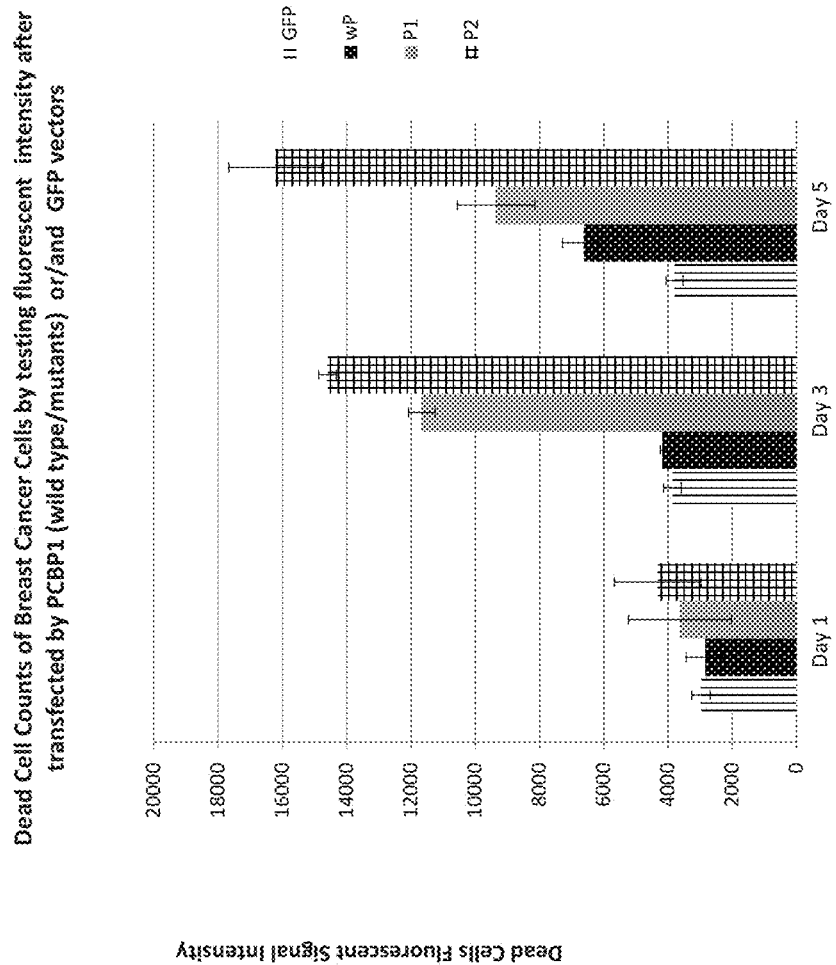
Figure 9B:
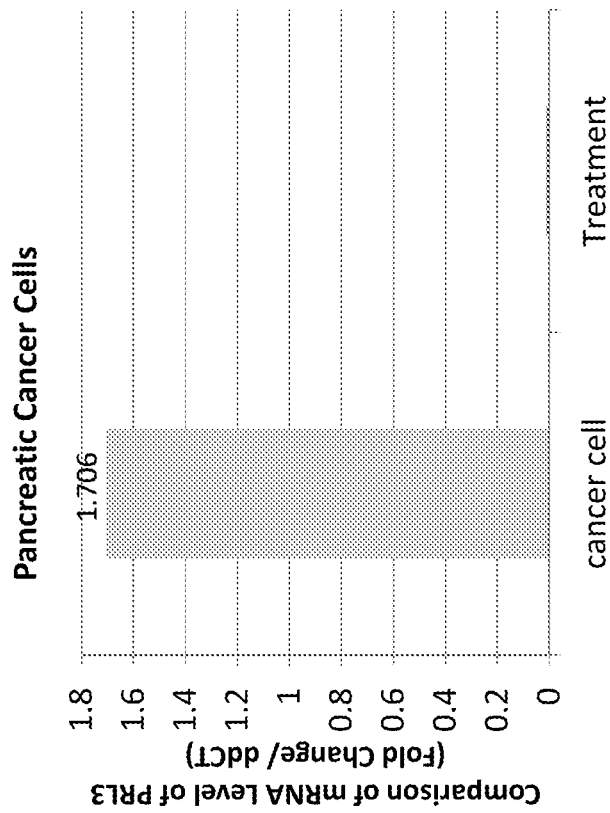
FIGS. 9A-B show PCBP1 expression in pancreatic cancer cells after transfection with one of the compositions of the present disclosure. The graphs show qRT-PCR results of PCBP1 mRNA fold change after a vector containing a wild type PCBP1 (treatment) or GFP (cancer cell) is transfected into pancreatic cancer cell. Compared with GFP group, the PCBP1 group shows significant increase of PCBP1 mRNA level in pancreatic cancer cells (fold change indicated in FIG. 9A). The GFP group also showed a high PRL3 mRNA expression compared to the PCBP1 group (fold change indicated in FIG. 9B).
Figure 9A:
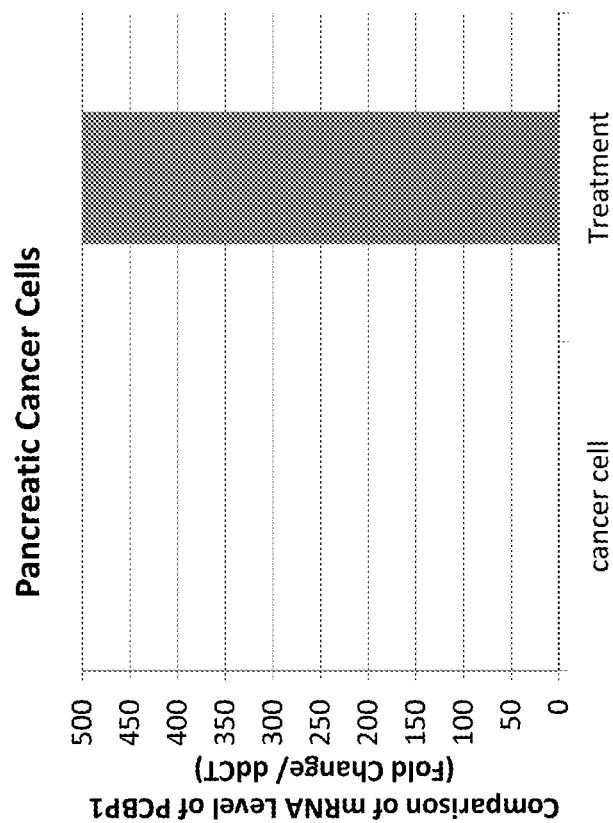
Figure 10:
FIG. 10 shows the fold change of PCBP1 mRNA expression levels in treatment groups with wild-type and mutants of PCBP1 in prostate cancer cell line (DU-145) when compared with GFP group (control). The graph shows the qRT-PCR results demonstrating the PCBP1 mRNA fold expression change in cancer cells (DU-145)transfected with vectors containing either PCBP1 (WT/mutants)+GFP or GFP-only. Compared with the GFP group, all the PCBP1 groups (WT and mutants) demonstrated a significant increase of PCBP1 mRNA levels in the prostate cancer cells (fold change indicated in figure, *P<0.01). (GFP: Green Fluorescent Protein vector. wPCBP1_0-GFP vector, mPCBP1_1 (one site mutation).; mPCBP1_2 (two site mutations).

Example 5—Transfection with Mutant PCBP1 Decreases Breast Cancer Cell Migration The breast cancer cells from the MCF-7 cell line were transfected with vectors containing GFP only, wild type PCBP1 (wPCBP1_0-IRES-GFP) and GFP, or PCBP1 T60A & T127A (mPCBP1_2-IRES-GFP) and were observed for five days post-transfection. The migration of these cells was observed as detailed above. Table 4 shows the net cell migration in CDZ of the different transfected cells. FIGS. 7A-C show the cell migration adjusted to percentage of cells per well. The percentage of migrated cells (per well) in the GFP group was significantly higher than that of wild type PCBP1 (wPCBP1_0) and PCBP1 T60A & T127A (mPCBP1_2). Among these three groups, mPCBP1_2 displayed the lowest percentage of migrated cells per well.

TABLE 4

Calculation of Net Cell Migration of
melanoma cells into CDZ

| Vector | Net Cell Migration in CDZ | Std |
|---|---|---|
| GFP | 56.5 | 4.950 |
| wPCBP1_0 | 18.5 | 4.950 |
| mPCBP1_1 (S223L) | 11 | 2.828 |
| mPCBP1_2 (T60A & T127A) | 5 | 1.414 |

Example 6—Use of PCBP1 Mutants to Inhibit Tumor Metastasis

Design of the Animal Model to Study Cancer Gene Therapy:

Experimental Dean: A cancer cell line (i.e., MCF-7, ATCC for breast cancer model-BC) is tumorigenic in mice and can be used to study breast cancer (BC) tumor growth in immune deficient animals (i.e., Nude mice strain: BALB/c from Charles River Lab, NC). These cells will be used to develop an in vivo precision method for testing therapeutic efficacy. Initially, it will be prepared for injectable cancer cell lines that are stably transduced by the vector with a marked gene, i.e., encoding red fluorescent protein (RFP). This will allow monitoring growth and migration of the cancer cells, illustrated or monitored by the fluorescent bio-imaging system or fluorescent microscope. After the cancer cells are prepared, they will be injected subcutaneously into mice to generate breast cancer tumors after a week. By using this new method, cancer cells will be precisely traced and studied during their metastasis, following treatment of gene therapeutic vector such as AAV-PCBP1m.

Procedures will be performed as follows with an example of a BC study:

(1) The RFP will be delivered into a BC cell line (MCF-7, ATCC), such as by using a lentiviral-backbone for integration of the RFP gene into the cell genome for stable and long-term expression of the RFP reporter gene. After confirming successful RFP transduction into the cells (by using a fluorescent microscope or FACS), BC cells will be selected and injected.

(2) Mice will be divided into four groups (n=6). RFP-BC cells will be injected into the flank of mice at same conditions (same cell count, injection time) in all groups. BC tumor sizes will be assessed and recorded daily or twice every week. Experimental design and expected outcome will be as described in the following Table 5:

TABLE 5

Example of the In vivo Experiment
Designed with Implantation of BC in Mice.

| | Grouping | | | |
|---|---|---|---|---|
| | Group A (GA) | | Group B (GB) | |
| | Transduced BC cells with RFT | | | |
| | RFP-BC | | RFP-BC | |
| | Sub-group | | | |
| | GA-1 | GA-2 | GB-1 | GB-2 |
| | Injection of therapeutic vectors (Day 7) | | | |
| Treatment | PCBP1 (WT)-GFP | PCBP1 (2 site mutation)-GFP | Control (empty vector) | Control (no vector) |
| Expectation of tumor growth | Tumor suppressed | Tumor strongly suppressed | Tumor grow fast | Tumor grow fast |

The vector containing therapeutic genes will be injected into the tumors directly. Mice will be sacrificed 3 weeks after treatment, for histology studies. Tumor tissues will be extracted for immunohistochemistry (IHC) assay for RFP, GFP, PRL-3, PCBP1 and SOX2 (a BC cell marker). RFP and GFP will be detected on these tissues to confirm BC cell growth and vector delivery, as described in Table above. Additional tissues (including lung, liver, brain and pancreas)

will be extracted for tumorigenicity and metastasis studies. RFP and GFP will be detected in these tissues to monitor if BC migrated into these tissues. qRT-PCR, WB and IHC will be also performed. Proteomics studies will be done by two-dimensional gel electrophoresis combined with mass spectrometry techniques to compare protein expression in mice with control vs. PCBP1 mutant transduction. The difference among experimental groups will be compared using student's t test. Statistical significance will be determined as $P<0.05$.

(3) The analysis of the outcome for the results after treatment may be expected as following Table 6:

TABLE 6

In vitro experimental designed and expected results

| Groups (i.e., breast cancer cells) | Transfected by AAV-GFP vector | Transfected by AAV-PCBP1w-GFP (wild-type) vector | Transfected by AAV-PCBP1m (different new mutations)-GFP |
|---|---|---|---|
| Green Fluorescent Signal | Yes | Yes | Yes |
| The mRNA levels of PCBP1 determined by qRT-PCR | + | +++ | +++ |
| The protein levels of PCBP1 determined by WB | − | +++ | +++ |
| The mRNA levels of PRL3 determined by qRT-PCR | +++ | ++ | ++ |
| Protein levels of PRL3 determined by WB | ++++ | ++ | +/− |
| Cancer cell migration determined by migration assay | ++++ | ++ | +/− |
| Cancer cell apoptosis assay | − | ++ | ++++ |
| Cell Proliferation Assay | ++++ | ++ | +/− |

Example 7—Treatment of Glioblastoma by Expressing PCBP1 in the Tumor Cells

Figure 11:
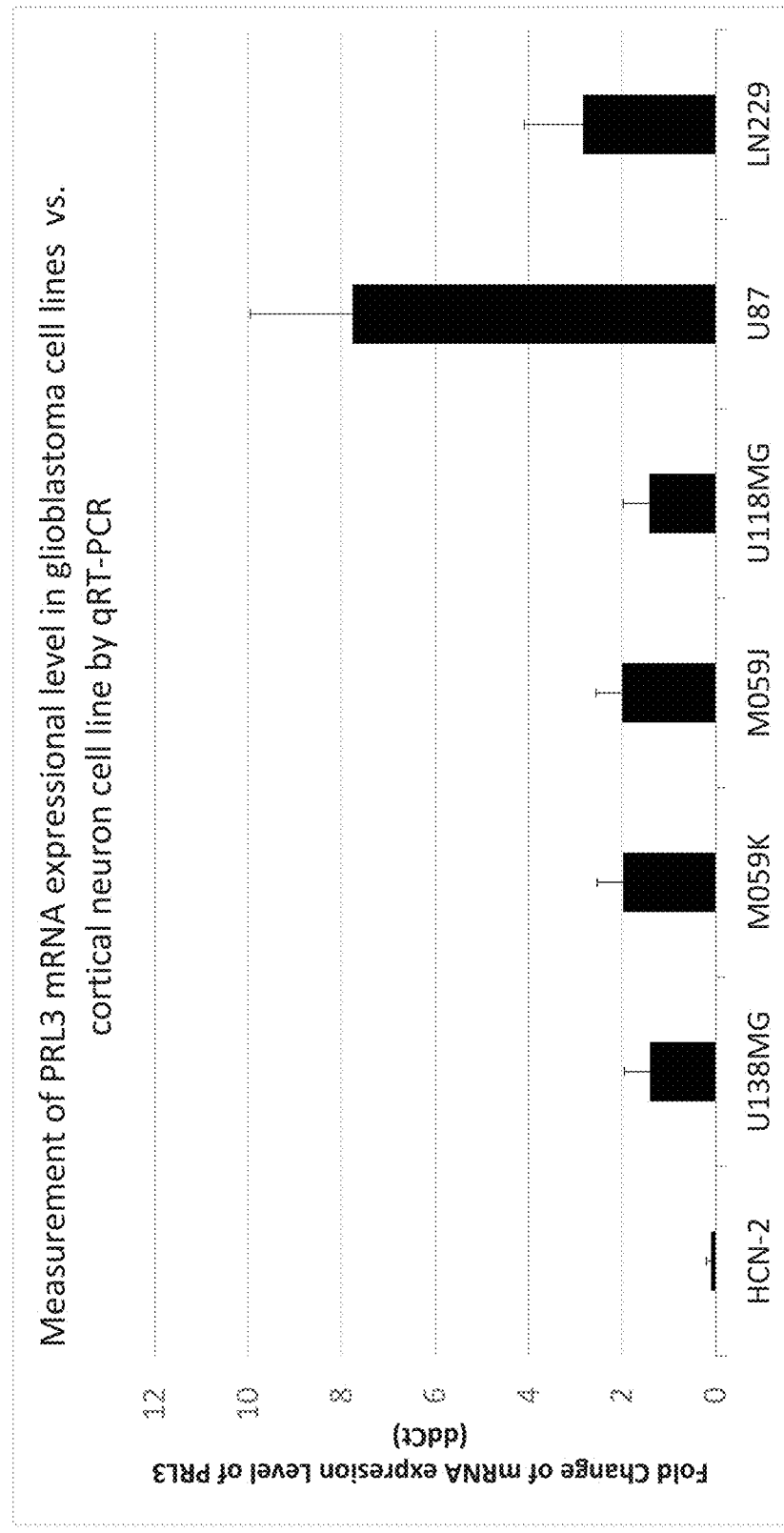
FIG. 11 shows the measurement of PRL3 mRNA expression levels in glioblastoma cell lines vs. a cortical neuron cell line (HCN-2) by qRT-PCR. Compared with a normal brain cortical cell line, PRL3 mRNA is overexpressed in all six glioblastoma cell lines tested.

Elevated levels of PRL3 mRNA are found in glioblastoma cells. As shown in FIG. 11, compared to expression in a normal brain cortical cell line, elevated PRL-3 expression was detected in six different glioblastoma cell lines (U138MG, M059K, M059J, U118MG, U87, and LN229). The cell lines U87 and LN229 show the greatest increase in PRL-3 mRNA expression and were selected for further testing.

Figure 12:
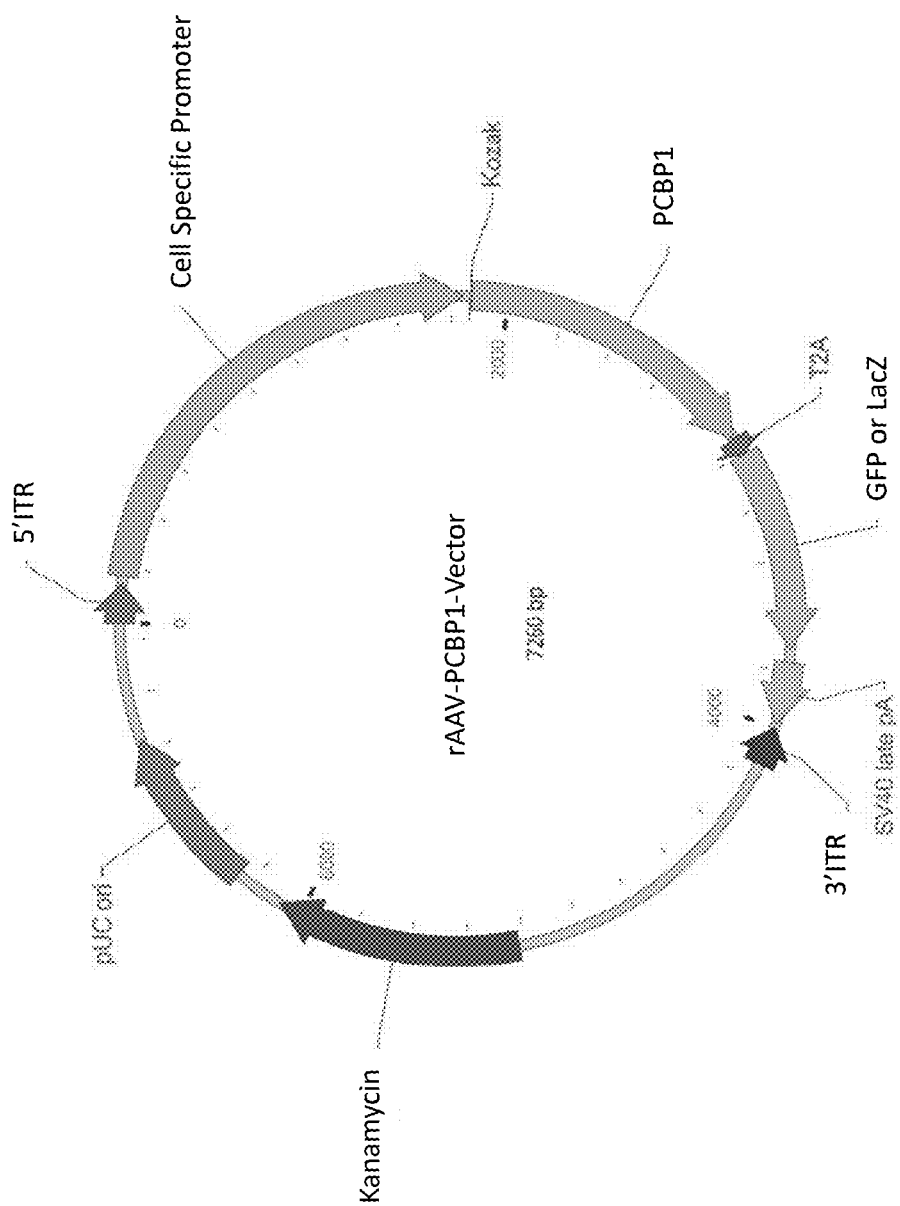
FIG. 12 shows a schematic of an AAV vector expressing PCBP1 (wild type or mutant) under the control of a cell-specific promoter. Here, expression of a PCBP1 sequence (wt, mPCBP1_1, or mPCBP1_2) is driven by a cell-specific promoter such as glial fibrillary acidic protein (GFAP) promoter, to treat glioblastoma in the brain. GFP or LacZ are reporter genes used to illustrate co-localization of the therapeutic protein (e.g. PCBP1) and marker protein expression in specific cell types.
Figure 13B:
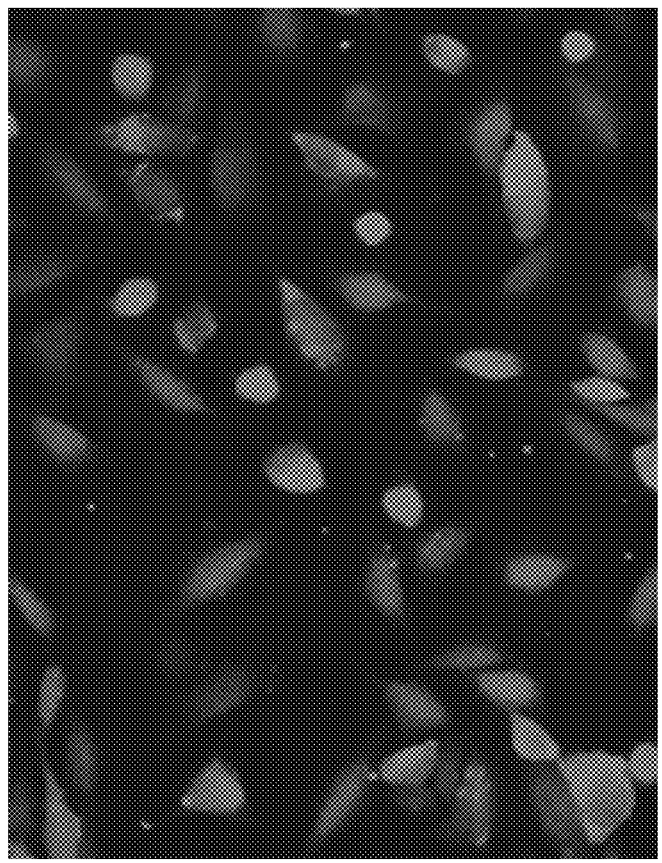
FIGS. 13A-B show in vitro detection of transgene expression driven by a specific promoter in glioblastoma (brain) cells. LN229 glioblastoma cells transfected with the phGFAP-LacZ vector were analyzed via immunohistochemistry. Cancer cells (LN299) were observed by bright field microscopy (Panel A). The expressed proteins from the LacZ gene driven by the specific promoter were detected by the anti-β-galactosidase antibody, A11132 (diluted 1:700). (Panel B). Northernnights™ 557-conjugated anti-rabbit antibody (NL004, R&D system) was used as the secondary antibody (dilution 1:200) resulting in a red fluorescent signal. Magnification is 20×.
Figure 13A:
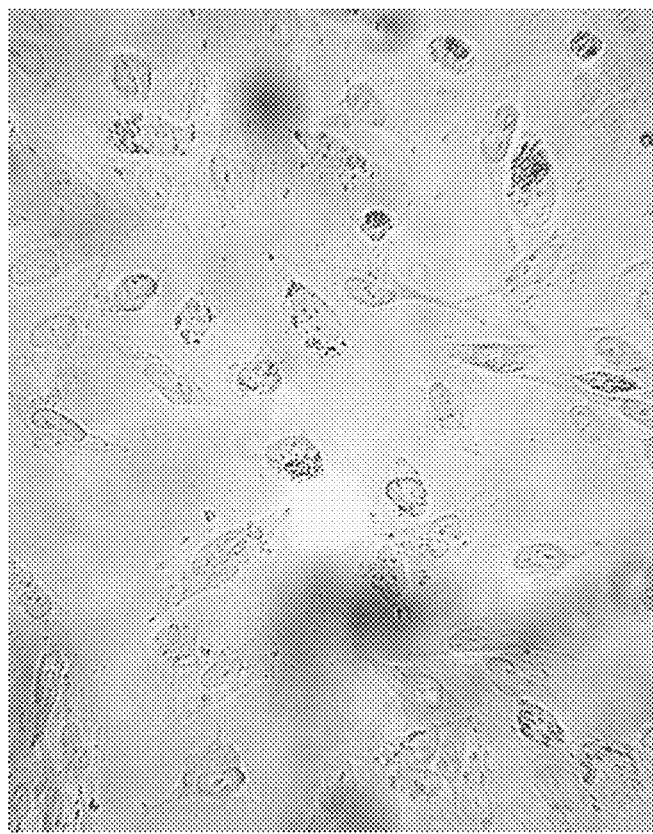
Figure 14B:
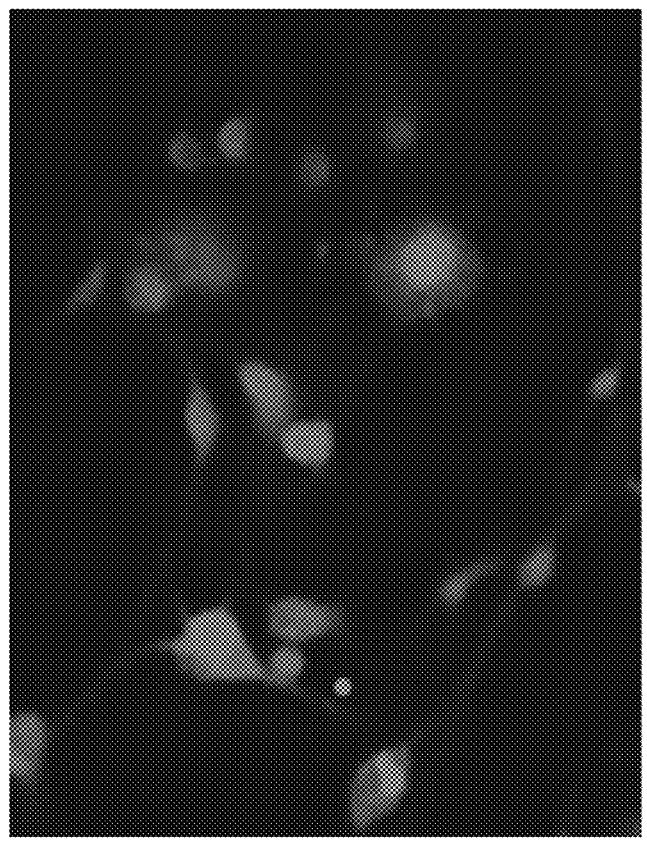
FIGS. 14A-B shows the in vitro detection of transgene expression driven by a specific promoter in glioblastoma (brain) cells. U87 glioblastoma cells transfected with the phGFAP-LacZ vector were analyzed via immunohistochemistry. Cancer cells (U87) were observed by bright field microscopy (Panel A). The expressed proteins from the LacZ gene driven by the specific promoter were detected by the anti-β-galactosidase antibody, A11132 (diluted 1:700). (Panel B). Northernnights™ 557-conjugated anti-rabbit antibody (NL004, R&D system) was used as the secondary antibody (dilution 1:200) resulting in a red fluorescent signal. Magnification is 20×.
Figure 14A:
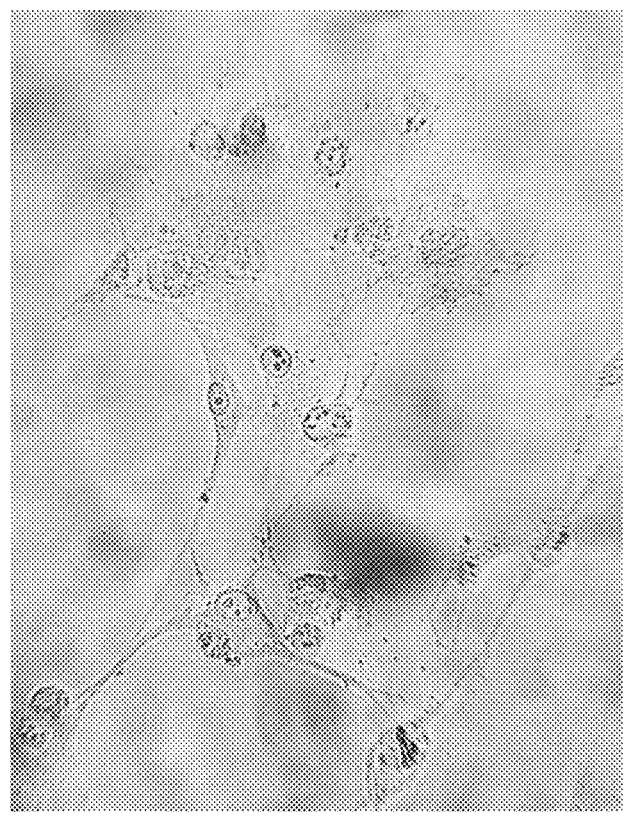
Figure 15B:
FIGS. 15A-B shows the in vitro detection of transgene expression driven by a specific promoter in kidney cells. 293FT kidney cells transfected with the phGFAP-LacZ vector were analyzed via immunohistochemistry. 293FT kidney cells were observed by bright field microscopy (Panel A). The expressed proteins from the LacZ gene driven by the specific promoter were not detected by the anti-β-galactosidase antibody, A11132 (diluted 1:700). (Panel B). Northernnights™ 557-conjugated anti-rabbit antibody (NL004, R&D system) was used as the secondary antibody (dilution 1:200) which would have resulted in a red fluorescent signal if β-galactosidase were expressed in these cells. Magnification is 20×.
Figure 15A:
Figure 16B:
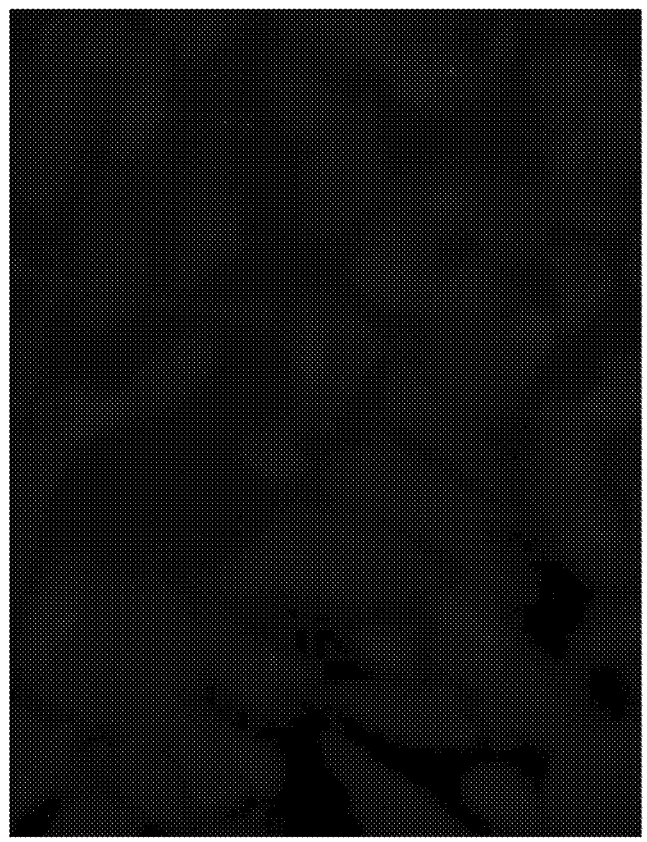
FIGS. 16A-B shows the in vitro detection of transgene expression driven by a specific promoter in eye cells. ARPE-19 eye cells transfected with the phGFAP-LacZ vector were analyzed via immunohistochemistry. ARPE-19 eye cells were observed by bright field microscopy (Panel A). The expressed proteins from the LacZ gene driven by the specific promoter were not detected by the anti-β-galactosidase antibody, A11132 (diluted 1:700). (Panel B). Northernnights™ 557-conjugated anti-rabbit antibody (NL004, R&D system) was used as the secondary antibody (dilution 1:200) which would have resulted in a red fluorescent signal if β-galactosidase were expressed in these cells. Magnification is 20×.
Figure 16A:
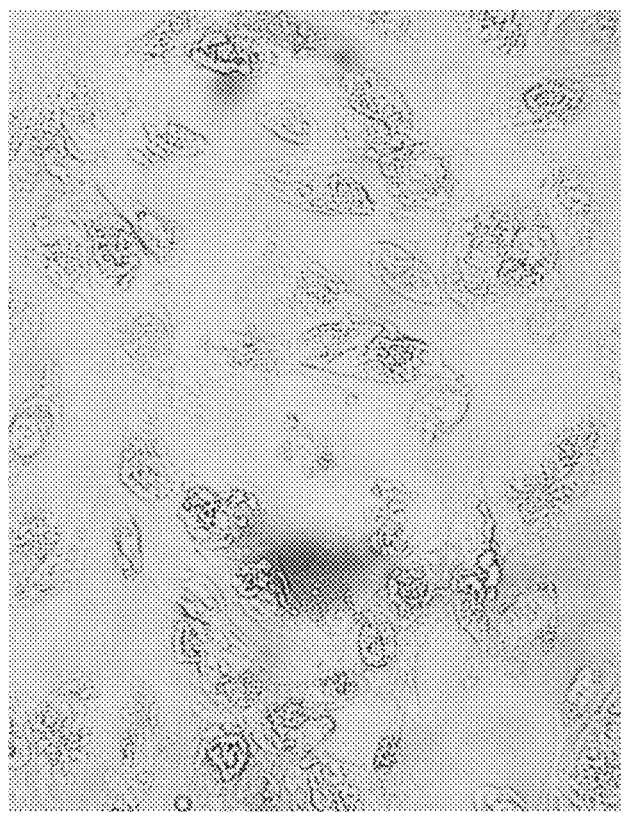
Figure 17:
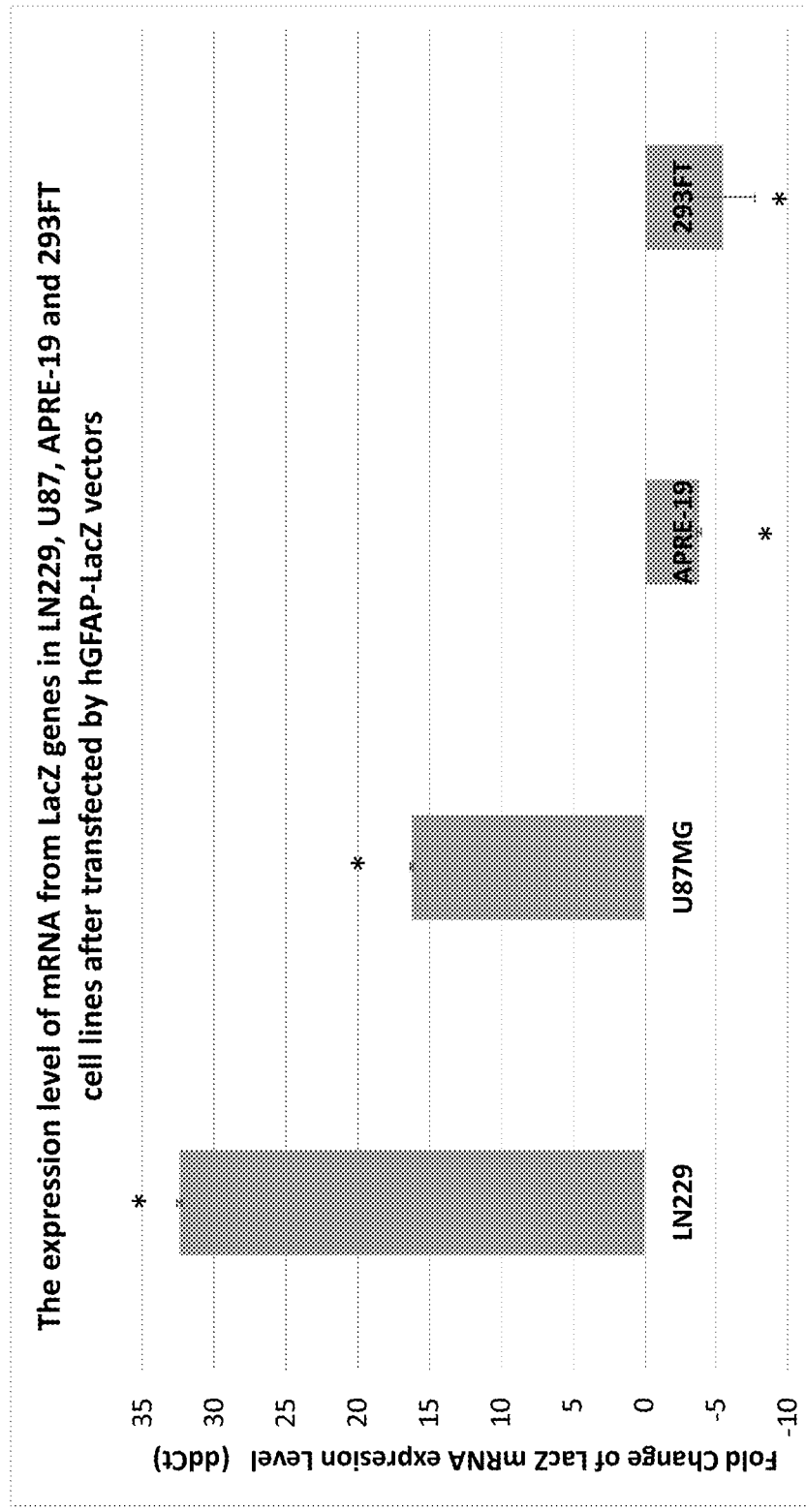
FIG. 17 shows the detection of LacZ mRNA expression driven by phGFAP promoter in different cell types by qRT-PCR. LacZ mRNA expression levels in different cells (LN229, U87, ARPE-19, and 293FT) was monitored after transfection of these cells with a vector containing LacZ under the control of hGFAP. The fold changes were compared with AAV-GFP vectors as control (*$p<0.05$). These data confirm that the LacZ proteins are expressed in the glioblastoma (brain) cells (e.g. U87 and NL229 cells) under the hGFAP promoter, but not in other cell types (e.g. ARPE-19 and 293FT cells)

Overexpression of Wild Type or Mutant PCBP1 Decreases PRL3 Expression in Glioblastoma Cells As previously demonstrated, expression of wild type or mutant PCBP1 decreased expression of a gene associated with metastasis, PRL-3, and inhibited cell migration. To test the effect of overexpression of PCBP1 sequences, six different glioblastoma cell lines were transfected with rAAV9 expression vectors containing a wild type or mutant PCBP1 sequence of the disclosure under control of a glioblastoma cell-specific promoter, glial fibrillary acidic protein (GFAP) that enables expression of AP-PCBP1 in glioblastoma cells (see FIG. 12). FIGS. 13-16 demonstrate the specificity of this vector expression in glioblastoma cells. FIG. 13 shows immunohistochemistry analysis of LN299 glioblastoma cells treated with the phGFAP-LacZ vector. FIG. 14 shows immunohistochemistry analysis of LN299 glioblastoma cells treated with the phGFAP-LacZ vector. As shown in FIGS. 13B and 14B, the LacZ gene driven by the GFAP promoter is detected by an anti-β-galactosidase specific antibody, A11132 (ThermoFisher at a dilution of 1:700) in both transfected glioblastoma cell lines. However, β-galactosidase is not detected in kidney (FIG. 15) or eye (FIG. 16) cells indicating this vector will express its cargo only in glioblastoma cells. A comparison of the LacZ mRNA expression levels is shown in FIG. 17.

Figures 18A, 18B:
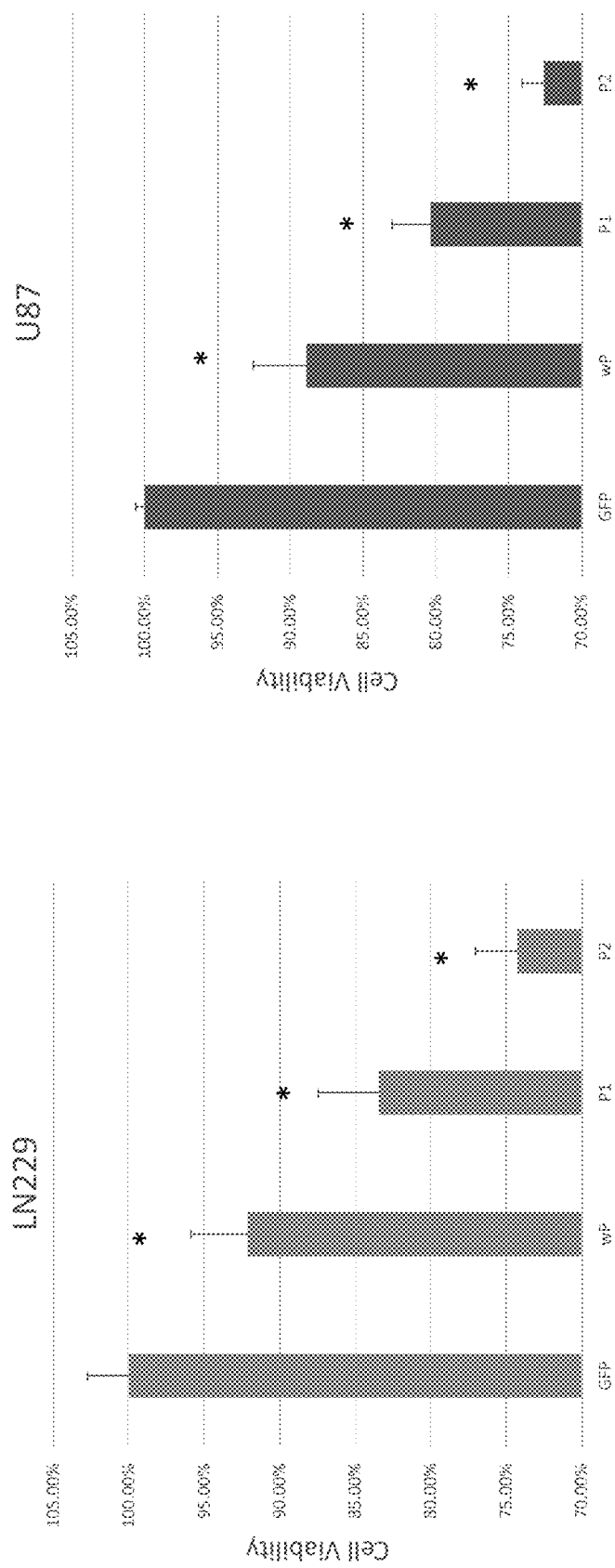
FIGS. 18A-B show the cell viability of glioblastoma cell lines LN229 and U87 cells after transfection with an AAV vector containing either GFP only, wild type PCBP1 (wP), mPCBP1_1 (P1), or mPCBP1_2 (P2). Panel A shows viability of LN229 glioblastoma cells. Panel B shows viability U87 glioblastoma cells. (*$p<0.05$ vs GFP).
Figures 19A, 19B:
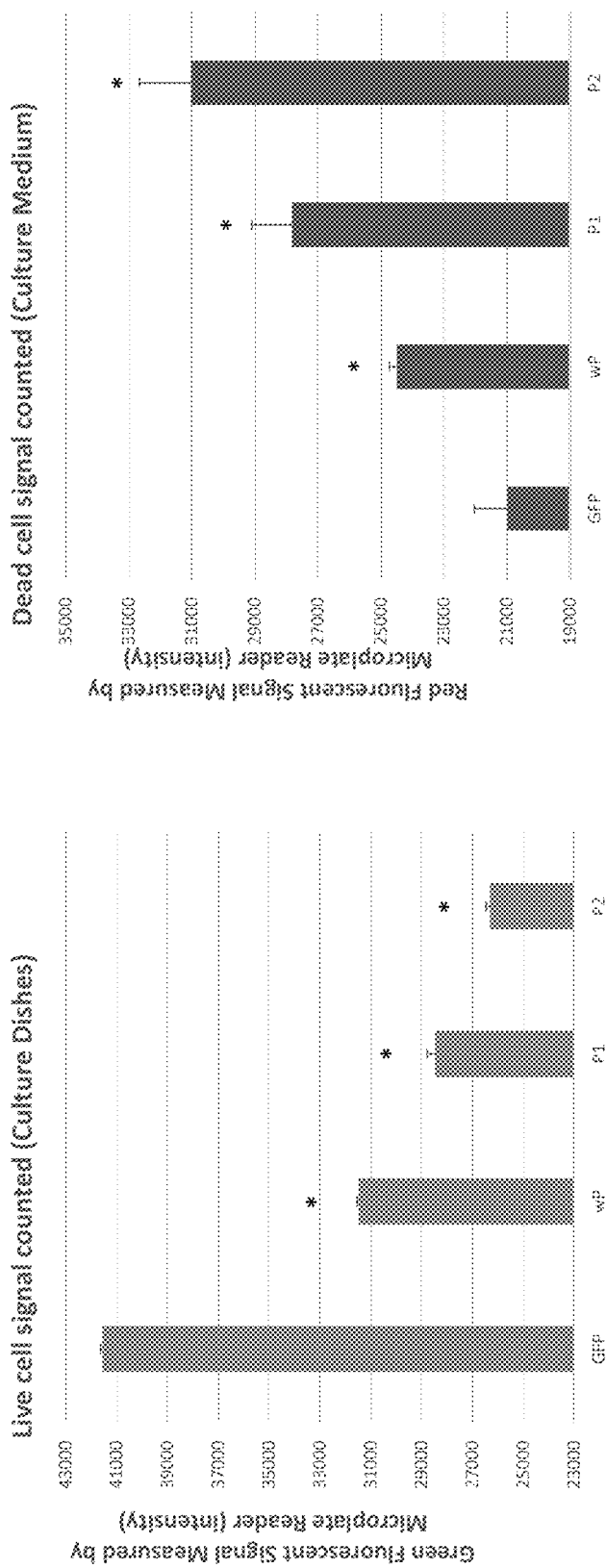
FIGS. 19A-B show the live/dead cell signal in U87 glioblastoma cells after transfection with a control or PCBP-1 containing vector. Cells were transfected with AAV-GFP, AAV-PCBP1 (wP), AAV-PCBP1_1 (P1), or AAV-PCBP1_2 (P2), and cell viability tested after four days. The live cells were stained with Calcein AM (Panel A), and the dead cells were stained with EthD-1 (Panel B). The dead cells were significantly increased after transfection with a PCBP1-containing vector compared with cells transfected with a GFP control vector. *$p<0.05$
Figure 21:
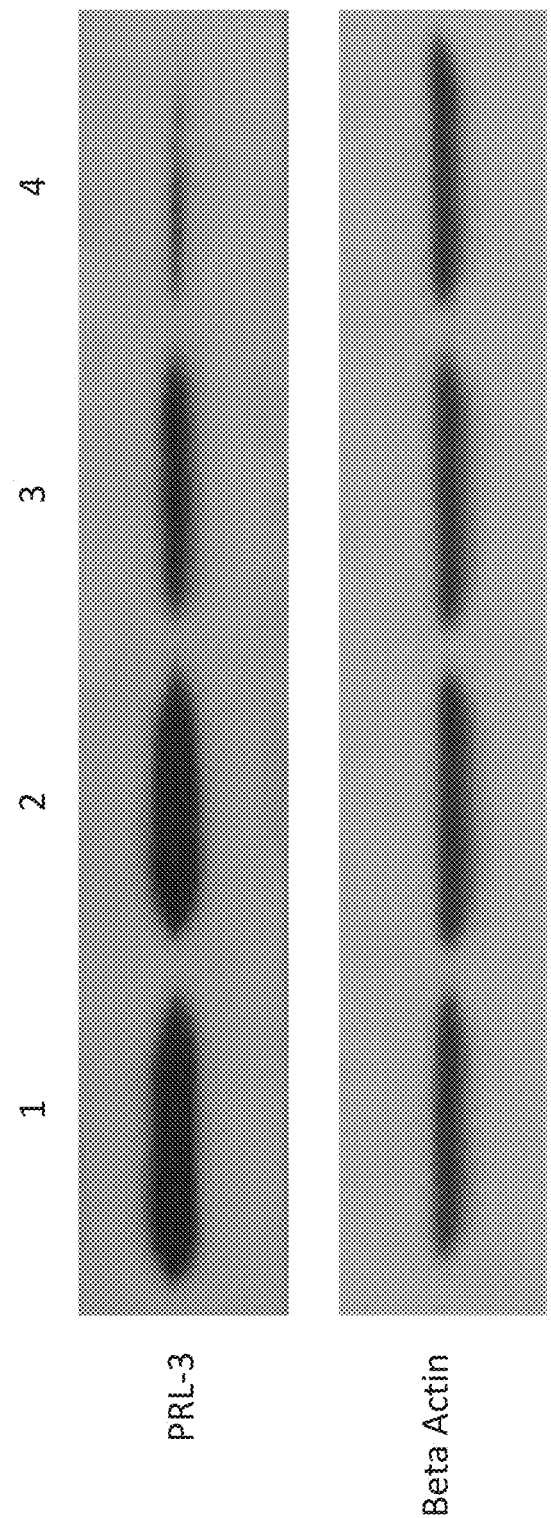
FIG. 21 shows PRL3 expression levels in U87 glioblastoma cells transfected with either AAV-GFP (lane 1), AAV-PCBP1 (lane 2), AAV-PCBP1_1 (lane 3), or AAV-PCBP1_2 (lane 4). PRL3 protein levels were tested using a Western Blot. Beta actin was used as the internal loading control.

Two micrograms of an AAV vector containing 1) GFP only; 2) wild type PCBP1; 3) mPCBP1_1; or 4) mPCBP1_2 was transfected into the LN229 and U87 glioblastoma cell lines and cell proliferation was tested by using the Vybrant MTT kit. As shown in FIGS. 18A-B, overexpression of wild type PCBP1 or either mutant significantly inhibit the proliferation of the glioblastoma cells when compared with non-treatment with the AAV-GFP vector control. Further, overexpression of a PCBP1 mRNA increases the number of dead cells in the culture, as shown in FIGS. 19 and 20. Dead and live U87 glioblastoma cells were analyzed using the LIVE/DEAD™ Viability Kit (Thermofisher, Inc.) after transfection by AAV-GFP and AAV-PCBP1 and mutants. FIG. 19A shows that the control-treated cell culture contains significantly more live cells than cells transfected with vectors containing wild type or mutant PCPB1 sequences, and FIG. 19B shows that these PCBP1 cell cultures contain significantly more dead cells than the control-treated cell culture. FIGS. 20A-D show the staining of live/dead U87 cells after transfection with either a GFP-control vector or a vector containing a PCBP1 sequence. As shown in FIG. 21, treatment by all forms of PCBP1 downregulated PRL3 protein expression in the U87 glioblastoma cell line, with the greatest decrease in PRL3 expression observed in cells treated with mPCBP1_2.

Figures 22A, 22B:
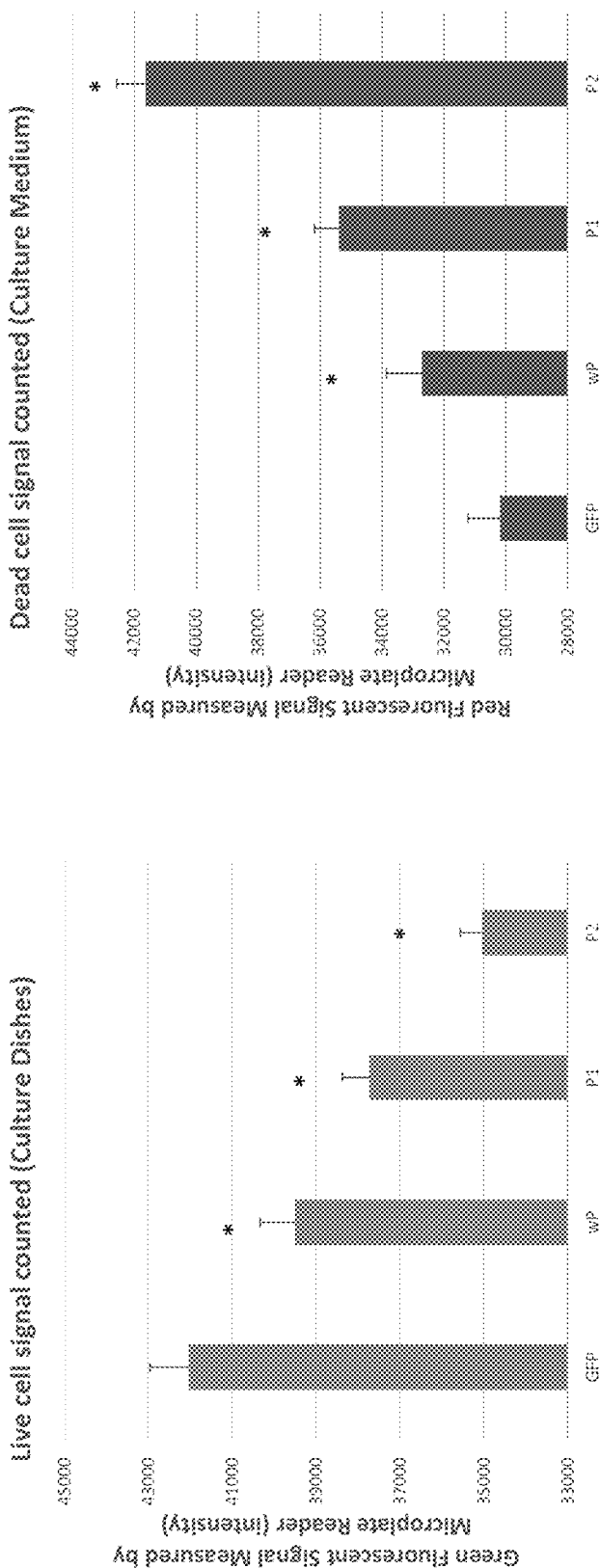
FIGS. 22A-B show the live/dead cell signal in LN229 glioblastoma cells after transfection with a control or PCBP-1 containing vector. Cells were transfected with AAV-GFP, AAV-PCBP1 (wP), AAV-PCBP1_1 (P1), or AAV-PCBP1_2 (P2) and cell viability tested after four days. The live cells were stained with Calcein AM (Panel A), and the dead cells were stained with EthD-1 (Panel B). The dead cells were significantly increased after transfection with a PCBP1-containing vector compared with cells transfected with a GFP control vector. *$p<0.05$
Figure 24:
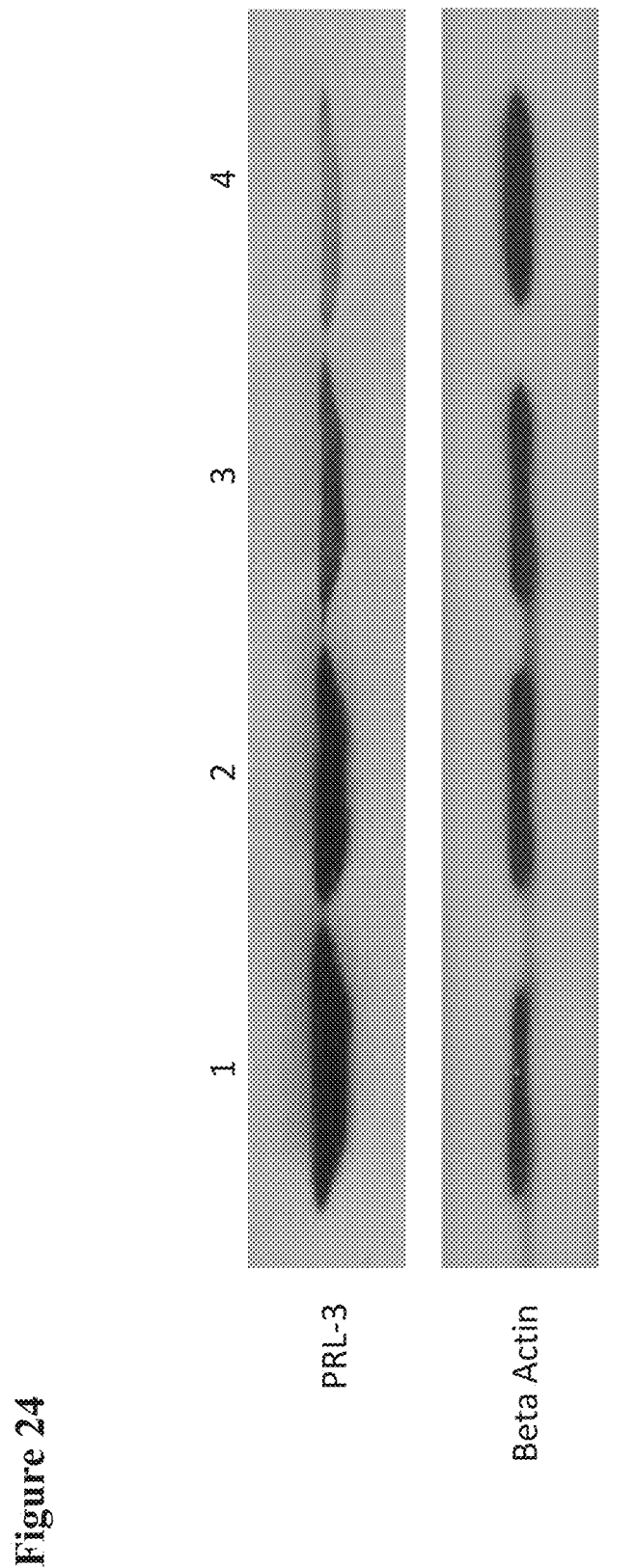
FIG. 24 shows the PRL3 protein levels in LN229 glioblastoma cells transfected with either AAV-GFP (lane 1), AAV-PCBP1 (lane 2), AAV-PCBP1_1 (lane 3), or AAV-PCBP1_2 (lane 4). PRL3 protein levels were tested using a Western Blot. Beta actin was used as the internal loading control.
Figures 25A, 25B:
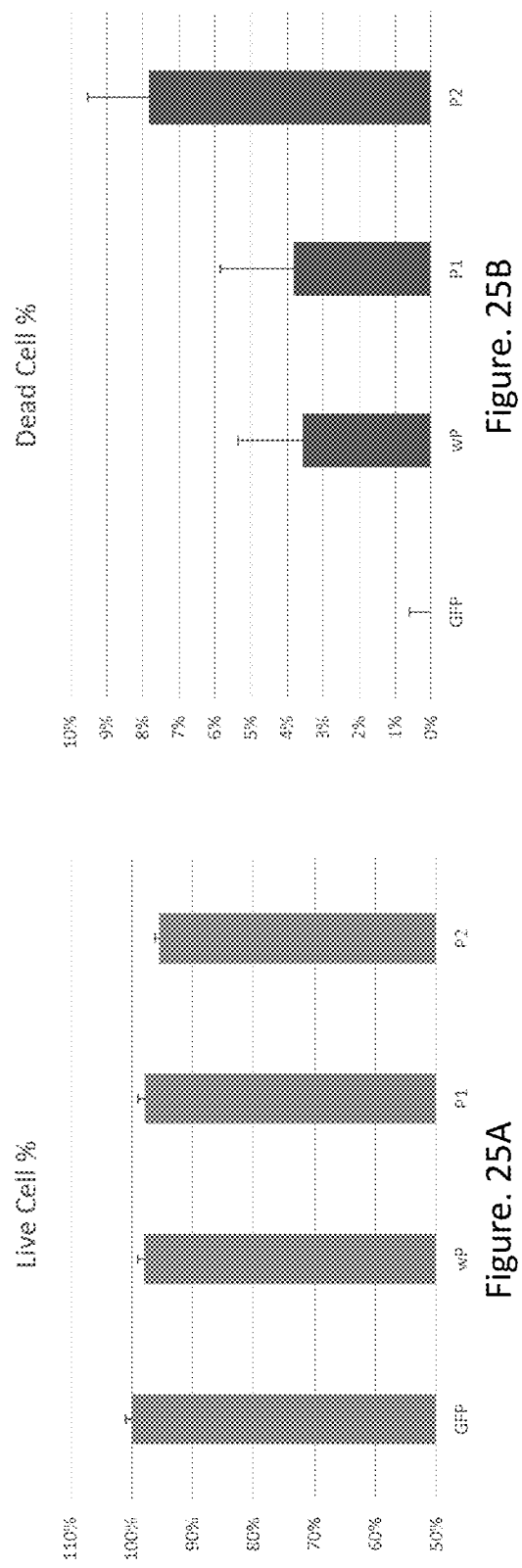
FIGS. 25A-B show live/dead analysis of the glioblastoma M059J cell line after transfection by AAV-GFP and AAV-PCBP1 and mutants. wP=wild type PCBP1; P1=mPCBP1_1; P2=mPCBP1_2. *$p<0.05$ compared with GFP.
Figures 27A, 27B:
FIGS. 27A-B show live/dead analysis of the glioblastoma U118MG cell line after transfection by AAV-GFP and AAV-PCBP1 and mutants. wP=wild type PCBP1; P1=mPCBP1_1; P2=mPCBP1_2. *$p<0.05$ compared with GFP.
Figures 28A, 28B:
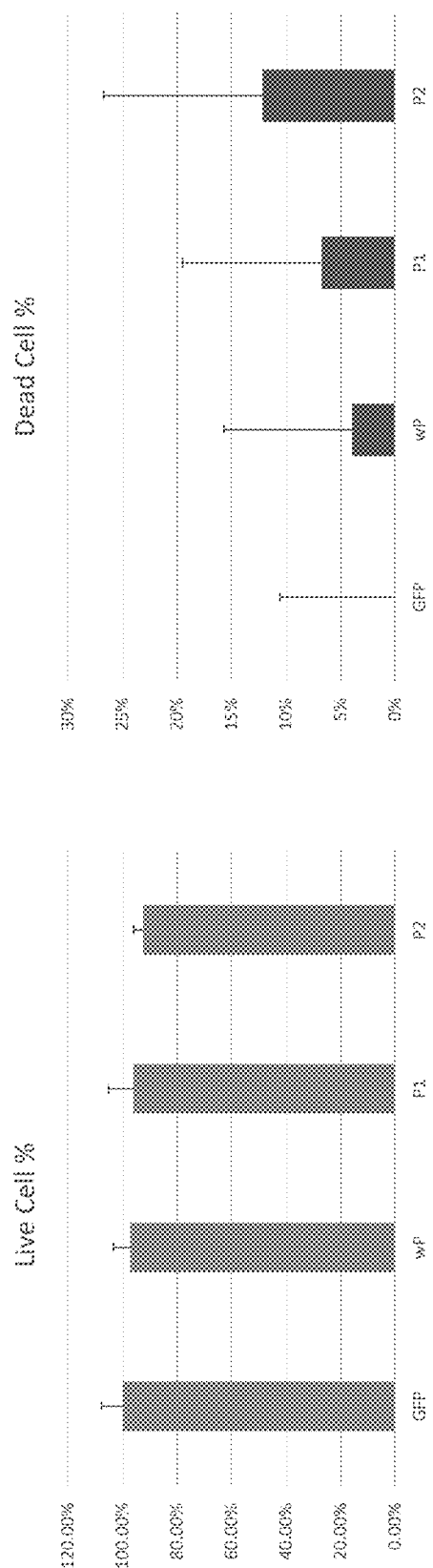
FIGS. 28A-B show live/dead analysis of the glioblastoma U138MG cell line after transfection by AAV-GFP and AAV-PCBP1 and mutants. wP=wild type PCBP1; P1=mPCBP1_1; P2=mPCBP1_2. $p<0.05$ compared with GFP.

These results were not specific to the U87 cell line, and were also demonstrated in other glioblastoma cell lines. Transfection of LN299 glioblastoma cells with wild type or mutant PCBP1 increased the number of dead cells in the cell culture (FIGS. 22 and 23), and decreased levels of PRL3 protein expression (FIG. 24). Again, treatment with mPCBP1_2 showed the greatest decrease in PRL3 protein expression (FIG. 24). The same effect on cell viability was observed in the M059J (FIG. 25), M059K (FIG. 26), U118MG (FIG. 27), and U138MG (FIG. 28) glioblastoma cell lines.

Figure 29:
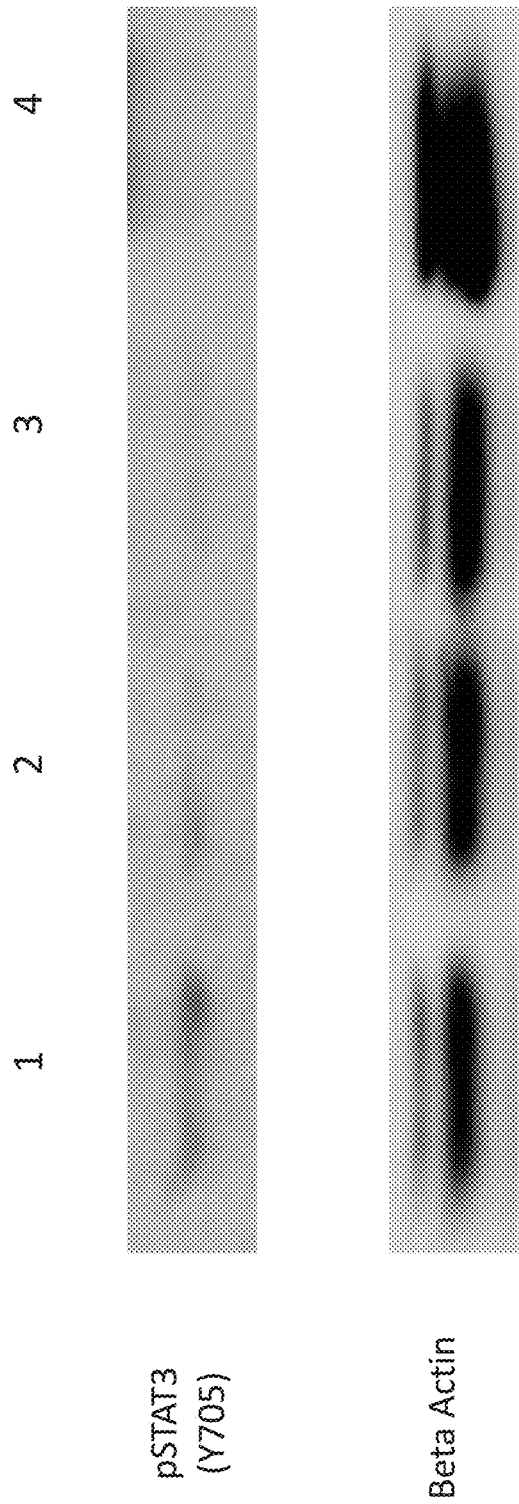
FIG. 29 shows the measurement of pSTAT3 (Y705) protein levels by Western Blot in PCBP1-transfected U87 glioblastoma cells. Cells were transfected with AAV-GFP (lane 1), AAV-PCBP1 (lane 2), AAV-mPCBP1_1 (lane 3), or AAV-mPCBP1_2 (lane 4). Treatment by all forms of PCBP1 down-regulated STAT3 levels in the glioblastoma cells, with mPCBP1_2 showing the most significant effect. Beta actin served as the internal control.

Overexpression of Wild Type or Mutant PCBP1 Decreases STAT3 Expression in Glioblastoma Cells Like PRL3, the expression of STAT3, a marker of cancer, was decreased in glioblastoma cells transfected with vectors containing wild type or mutant PCBP1 sequences. FIGS. 29 and 30 show STAT3 protein expression levels are decreased in U87 and LN299 glioblastoma cells transfected with wild type PCBP1, mPCBP11, or mPCBP1_2, with the mPCBP1_2 treated cells demonstrating the greatest decrease in STAT3 protein levels.

Example 8—Treatment of Ovarian and Prostate Cancer by Expressing PCBP1 in the Tumor Cells To demonstrate the effect of PCBP1 overexpression is not restricted to glioblastoma cells, the SKOV3 ovarian cancer cell line was transfected with vectors containing wild type or mutant PCBP1 sequences. SKOV3 cells were transfected with either 0.5 sg or 2.0 μg lentivectors containing GFP, PCBP1, mPCBP1_1, or mPCBP1_2. Cell proliferation was assayed using MTT (Thermofisher Inc.). As shown in FIG. 31, transfection of all three PCBP1-containing vectors increased inhibition of cell proliferation in a dose-dependent manner. Further, FIG. 32 demonstrates transfection with a wild type or mutant PCBP1 sequence decreases PRL3 mRNA expression.

Similar results were observed in DU145 prostate cancer cells transfected with vectors containing wild type or mutant PCBP1 sequences. FIG. 33 demonstrates cells overexpressing PCBP1 showed a significant decrease in cell proliferation when compared to control cells. FIG. 34 shows that PRL3 protein expression levels are similarly decreased, with the mPCBP1_2 mutant showing the greatest decrease.

Example 9—Overexpression of Wild Type or Mutant PCBP1 is not Toxic to Non-Cancerous Cells To demonstrate the overexpression of PCBP1 is not toxic to non-cancerous cells, two normal cell types were transfected with vectors containing wild type or mutant PCBP1 and lactate dehydrogenase (LH) assays were performed. Lactate dehydrogenase is released from damaged cells into the media, and increased levels of LH are thus a biomarker for cytotoxicity and cytolysis. Normal brain cells (HCN-2) and normal breast cells (MCF10A) were each transfected with vectors containing 1) GFP only (e.g. no PCBP1 treatment), 2) wild type PCBP1; 3) mPCBP1_1; and 4) mPCBP1_2. FIGS. 33-34 demonstrate no significant killing of normal brain and breast cells by treatment with PCBP1.

INCORPORATION BY REFERENCE

All references, applications, publications, patents, and patent publications cited are incorporated by reference herein in their entirety for all purposes.

REFERENCES

1. J. Krause William (2005, July 2001). Krause's Essential Human Histology for Medical Students. Boca Raton: Universal Publishers. ISBN 9781581124682.
2. https://hive.biochemistry.gwu.edu/cgibin/prd/biomuta/servlet.cgi?gpageid=11&searchfield11=gene_name&searchvalue1=PCBP1).
3. Ghanem, L. R. et al. The Poly(C) binding protein Pcbp2, and its retrotransposed derivative Pcbp1, are independently essential to mouse development. Mol. Cell. Biol. 36, MCB.00936-15 (2015).
4. Basak, S. et al. The metastasis-associated gene Prl-3 is a p53 target involved in cell-cycle regulation. Mol. Cell 30, 303-14 (2008).
5. Lai, Z., Han, I., Zirzow, G., Brady, R O and Reiser, J. Intercellular protein delivery by lentivirus vectors using a herpes simplex virus vp22 fusion protein Proc. Natl. Acad. Sci. USA. 2000; 97: 11297-11302.
6. Chaudhury A, Chander P, Howe P H (2010) Heterogeneous nuclear ribonucleoproteins (hnRNPs) in cellular processes: Focus on hnRNP E1's multifunctional regulatory roles. RNA 16(8):1449-1462.
7. Lai Z., 2002: Design of an HIV-1 Lentiviral-Based Gene-Trap Vector to Detect Developmentally Regulated Genes in Mammalian Cells. Proceedings of the National Academy of Sciences of the United States of America Vol. 99, No. 6 (Mar. 19, 2002), pp. 3651-3656.
8. Wang H. et al. PCBP1 suppresses the translation of metastasis-associated PRL-3 phosphatase. Cancer Cell. 2010 Jul. 13; 18(1):52-62. doi: 10.1016/j.ccr.2010.04.028.
9. Reiser, J., Lai, Z., Zhang, X. Y. & Brady, R. O. Development of multigene and regulated lentivirus vectors. J. Virol. 74, 10589-99 (2000).
10. Lai, Z. & Brady, R. O. Gene transfer into the central nervous system in vivo using a recombinanat lentivirus vector. J. Neurosci. Res. 67, 363-371 (2002).
11. Lai, Z., Han, I., Park, M. & Brady, R. O. Design of an IV-1 lentiviral-based gene-trap vector to detect developmentally regulated genes in mammalian cells. Proc. Natl. Acad. Sci. U.S.A. 99, 3651-6 (2002).
12. Bardelli, S. Saha, J. A. Sager, K. E. Romans, B. Xin, S. D. Markowitz, C. Lengauer, V. E. Velculescu, K. W. Kinzler, B. Vogelstein (2003), PRL-3 expression in metastatic cancers Clin. Cancer Res., 9 pp. 5607-5615
13. F. Polato, A. Codegoni, R. Fruscio, P. Perego, C. Mangioni, S. Saha, A. Bardelli, M. Broggini (2005), PRL-3 phosphatase is implicated in ovarian cancer growth Clin. Cancer Res., 11 pp. 6835-6839
14. L. Peng, J. Ning, L. Meng, C. Shou (2004), The association of the expression level of protein tyrosine phosphatase PRL-3 protein with liver metastasis and prognosis of patients with colorectal cancer J. Cancer Res. Clin. Oncol., 130 pp. 521-526
15. Wang, Haihe et al. (2010) PCBP1 Suppresses the Translation of Metastasis-Associated PRL-3 Phosphatase. Cancer Cell, Volume 18, Issue 1, 52-62
16. PCBP1 mutation database: https:/hive.biochemistry.gwu.edu/cgi-bin/prd/biomuta/servlet.cgi?gpageid=11&searchfield1-gene_name&searchvalue1-PCBP1.
17. Qingchang Meng, et al. Signaling-dependent and coordinated regulation of transcription, splicing, and translation resides in a single co-regulator, PCBP1. *Proceedings of the National Academy of Sciences.* 5866-5871, doi: 10.1073/pnas.0701065104
18. Brown, A (2016). Identification and characterization of an hnRNP E1 translational silencing motif. *Nucleic Acids Research.* P5892-5907.2016, Vol. 44, No. 12. doi: 10.1093/nar/gkw241.

What is claimed is:

1. A method of inhibiting, preventing, or decreasing cancer cell migration comprising introducing a vector comprising a variant or mutant PCBP1 nucleic acid sequence into a cancer cell, wherein the variant or mutant PCBP1 nucleic acid sequence encodes a variant or mutant PCBP1 polypeptide comprising one or more variations or mutations selected from the group consisting of: S223L, T60A, and T127A, relative to the wild type PCBP1 polypeptide of SEQ ID NO: 2, and wherein the one or more variations or mutations result in reduced phosphorylation of a KH domain of the PCBP1 polypeptide as compared to a WT PCBP1 polypeptide.

2. The method of claim 1, wherein the cancer cell is of a mammalian subject.

3. The method of claim 2, wherein the mammalian subject is human.

4. The method of claim 1, wherein the cancer cell is from a melanoma, prostate, ovarian, or breast cancer.

5. The method of claim 1, wherein the variant or mutant PCBP1 polypeptide comprises the amino acid sequence of SEQ ID NO: 4.

6. The method of claim 1, wherein the cancer cell is from a tumor.

7. The method of claim 1, wherein the variant or mutant PCBP1 nucleic acid has at least 75% percent identity to the wild type PCBP1 nucleic acid sequence of SEQ ID NO: 1.

8. The method of claim 1, wherein the variant or mutant PCPB1 nucleic acid comprises the nucleic acid sequence of SEQ ID NO: 3 or SEQ ID NO: 5.

9. The method of claim 1, wherein the variant or mutant PCBP1 polypeptide further comprises additional variations or mutations.

10. The method of claim 1, wherein the variant or mutant PCBP1 polypeptide has at least 75% percent identity to the wild type PCBP1 amino acid sequence of SEQ ID NO: 2.

11. The method of claim 1, wherein the variant or mutant PCPB1 polypeptide comprises the amino acid sequence of SEQ ID NO: 6.

12. The method of claim 1, wherein the cell expresses multiple copies of a PCBP1 polypeptide encoded by the variant or mutant PCBP1 nucleic acid sequence.

13. The method of claim 1, wherein the vector comprises a variant or mutant PCBP1 nucleic acid sequence that encodes at least one KH domain.

14. The method of claim 1, wherein the variation or mutation is S223L.

15. The method of claim 1, wherein the variation or mutation is T60A and T127A.

16. The method of claim 1, wherein the variant for mutant PCBP1 nucleic acid comprises C668T relative to the wild type PCBP1 nucleic acid of SEQ ID NO: 1, and wherein the variant or mutant PCBP1 polypeptide comprises S223L relative to the wild type PCBP1 polypeptide of SEQ ID NO: 2.

17. The method of claim 1, wherein the variant or mutant PCBP1 nucleic acid comprises A178G and A379G relative to the wild type PCBP1 nucleic acid of SEQ ID NO: 1, and wherein the variant or mutant PCBP1 polypeptide comprises T60A and T127A relative to the wild type PCBP1 polypeptide of SEQ ID NO: 2.

18. A method to detect cancer cell migration and/or cancer development, comprising:
introducing a vector comprising a variant or mutant PCBP1 nucleic acid sequence into a cancer cell of a subject in need, thereby generating a transformed cancer cell; and
detecting cellular migration and/or cellular development by one of cancer cell imaging, detection of an increased cancer cell marker in a sample of the subject, or both cancer cell imaging and detection of an increased cancer cell marker, wherein the variant or mutant PCBP1 nucleic acid sequence encodes a variant or mutant PCBP1 polypeptide comprising one or more variations or mutations selected from the group consisting of: S223L, T60A, and T127A, relative to the wild type PCBP1 polypeptide of SEQ ID NO: 2, and wherein the one or more variations or mutations result in reduced phosphorylation of a KH domain of the PCBP1 polypeptide as compared to a WT PCBP1 polypeptide.

19. The method of claim 18, wherein the cell migration is metastasis.

20. The method of claim 18, wherein the cell is from a tumor.

21. The method of claim 18, wherein the cell is a cancer cell that was previously exposed to a therapeutic treatment in vitro.

22. The method of claim 18, wherein the cell is a cancer cell that was previously exposed to a therapeutic treatment in vivo.

23. The method of claim 18, wherein the marker is selected from the group consisting of: PRL-3, CD44 variant, E-cadherin, STAT-3, GFP, and vimentin.

24. A method of treating cancer in a subject in need thereof, the method comprising: expressing a variant or mutant PCBP1 polypeptide in a cancer cell of a tumor, wherein the variant or mutant PCBP1 polypeptide comprises reduced phosphorylation in a KH domain as a result of a variation or mutation within the KH domain, as compared to a WT polypeptide, and wherein the expressing stabilizes or reduces metastasis of the cancer in the subject in need thereof, thereby treating the cancer.

* * * * *